United States Patent
Singer et al.

(10) Patent No.: US 11,840,721 B2
(45) Date of Patent: Dec. 12, 2023

(54) METHODS AND DEVICES FOR IDENTIFYING MICROBIAL INFECTIONS

(71) Applicant: HelixBind, Inc., Marlborough, MA (US)

(72) Inventors: Alon Singer, Concord, MA (US); Ranjit Prakash, Northborough, MA (US); Jork Nolling, Hopedale, MA (US)

(73) Assignee: HelixBind, Inc., Boxborough, MA (US)

( * ) Notice: Subject to any disclaimer, the term of this patent is extended or adjusted under 35 U.S.C. 154(b) by 55 days.

(21) Appl. No.: 16/499,515

(22) PCT Filed: Apr. 2, 2018

(86) PCT No.: PCT/US2018/025681
§ 371 (c)(1),
(2) Date: Sep. 30, 2019

(87) PCT Pub. No.: WO2018/187206
PCT Pub. Date: Oct. 11, 2018

(65) Prior Publication Data
US 2021/0017581 A1 Jan. 21, 2021

Related U.S. Application Data

(60) Provisional application No. 62/480,953, filed on Apr. 3, 2017.

(51) Int. Cl.
*C12Q 1/68* (2018.01)
*C12Q 1/689* (2018.01)
*C12Q 1/6895* (2018.01)

(52) U.S. Cl.
CPC ........... *C12Q 1/689* (2013.01); *C12Q 1/6895* (2013.01)

(58) Field of Classification Search
None
See application file for complete search history.

(56) References Cited

U.S. PATENT DOCUMENTS

| | | | |
|---|---|---|---|
| 7,960,360 B2 | 6/2011 | Grandis et al. | |
| 9,132,426 B2 | 9/2015 | Prakash | |
| 9,663,830 B2 | 5/2017 | Singer | |
| 2003/0082535 A1 | 5/2003 | Leushner et al. | |
| 2004/0010129 A1* | 1/2004 | Hsu .................. | C12Q 1/689 536/23.1 |
| 2005/0079490 A1* | 4/2005 | Stuber .................. | C12Q 1/6813 435/6.14 |
| 2006/0046246 A1* | 3/2006 | Zeng .................. | G16B 30/10 435/5 |
| 2006/0160121 A1* | 7/2006 | Mounts .................. | C12Q 1/6837 435/6.13 |
| 2007/0031850 A1 | 2/2007 | Mounts et al. | |
| 2007/0042422 A1* | 2/2007 | Stuber .................. | C12Q 1/6888 435/6.12 |
| 2009/0208933 A1 | 8/2009 | Pachot et al. | |
| 2009/0286249 A1 | 11/2009 | Becker et al. | |
| 2010/0021910 A1 | 1/2010 | Cao et al. | |
| 2011/0177960 A1 | 7/2011 | Murphy et al. | |
| 2012/0276530 A1 | 11/2012 | Meller et al. | |
| 2012/0329050 A1 | 12/2012 | Nadeau et al. | |
| 2013/0203610 A1 | 8/2013 | Meller et al. | |
| 2013/0256118 A1 | 10/2013 | Meller et al. | |
| 2013/0267429 A1 | 10/2013 | Gardner et al. | |
| 2015/0099657 A1 | 4/2015 | Singer | |
| 2015/0284764 A1 | 10/2015 | Tets et al. | |
| 2017/0218434 A1* | 8/2017 | Singer .................. | C12Q 1/6883 |
| 2017/0259257 A1* | 9/2017 | Singer .................. | C12Q 1/686 |
| 2017/0292146 A1* | 10/2017 | Singer .................. | C12Q 1/6806 |
| 2020/0331938 A1 | 10/2020 | Singer et al. | |
| 2022/0002786 A1 | 1/2022 | Singer | |

FOREIGN PATENT DOCUMENTS

| | | | | |
|---|---|---|---|---|
| CN | 105063759 A | 11/2015 | | |
| WO | WO 2004/033720 A2 | 4/2004 | | |
| WO | WO 2004/061085 A2 | 7/2004 | | |
| WO | WO 2007/056463 A2 | 5/2007 | | |
| WO | WO 2007/106407 A2 | 9/2007 | | |
| WO | WO 2011/087789 A2 | 7/2011 | | |
| WO | WO 2012/138955 A2 | 10/2012 | | |
| WO | WO 2013/074601 A1 | 5/2013 | | |
| WO | WO 2013/176992 A2 | 11/2013 | | |
| WO | WO-2013176992 A2 * | 11/2013 | ........... | C12Q 1/6895 |
| WO | WO 2016/044621 A1 | 3/2016 | | |
| WO | WO-2016044621 A1 * | 3/2016 | ........ | B01L 3/502753 |
| WO | WO 2016/176992 A1 | 11/2016 | | |
| WO | WO-2018187206 A1 * | 10/2018 | ............... | C12Q 1/04 |

OTHER PUBLICATIONS

Ahmad et al., 2019. A high-throughput and rapid method for accurate identification of emerging multidrug-resistant Candida auris. Mycoses, 62(6), pp. 513-518. (Year: 2019).*
Al Griw, Huda, Ph.D Dissertation. 2012. Molecular detection of bloodstream pathogens in critical illness. The University of Manchester, School of Medicine (United Kingdom) pp. 1-351. (Year: 2012).*
Al-Griw et al., 2016. Comparative Assessment of SepsiTest™ Platform to BactScreen™ and in-house MGB-based All Bacteria Assay for Detection of Bacteraemia in Whole Blood Samples. Libyan J Vet and Med Sciences, vol. 2(2), 1-8. (Year: 2016).*
Gaitan et al., 2017. Nosocomial fungemia by Candida auris: first four reported cases in continental Europe. Revista iberoamericana de micologia, 34(1), pp. 23-27. (Year: 2017).*
Gebert S, Siegel D, Wellinghausen N. Rapid detection of pathogens in blood culture bottles by real-time PCR in conjunction with the pre-analytic tool MolYsis. J Infect. Oct. 2008; 57(4):307-16. Epub Aug. 29, 2008. (Year: 2008).*

(Continued)

*Primary Examiner* — Teresa E Strzelecka
*Assistant Examiner* — Olayinka A Oyeyemi
(74) *Attorney, Agent, or Firm* — Wolf, Greenfield & Sacks, P.C.

(57) ABSTRACT

The present disclosure generally relates to the field of microbial pathogen detection and identification utilizing genomic sequence recognition.

27 Claims, 10 Drawing Sheets
Specification includes a Sequence Listing.

(56) References Cited

OTHER PUBLICATIONS

Genbank Accession No. KC692045 Candida auris isolate VPCI_677/P/12 ITS1, partial sequence; 5.8S ribosomal RNA gene and ITS2, complete sequence; and 28S ribosomal RNA gene, partial sequence (submitted Feb. 26, 2013, retrieved on Sep. 7, 2021 from http://www.ncbi.nlm.nih.gov/nuccore/KC692045) (Year: 2013).*

Genbank Accession No. KX518348 Candida auris strain TA002-14 18S ribosomal RNA gene, partial sequence; internal transcribed spacer 1, 5.8S ribosomal RNA gene, and internal transcribed spacer 2, complete and 28S ribosomal RNA gene, partial sequence (submitted Jul. 7, 2016) (Year: 2016).*

Hansen et al. Evaluation of new preanalysis sample treatment tools and DNA isolation protocols to improve bacterial pathogen detection in whole blood. J Clin Microbiol. Aug. 2009; 47(8):2629-31. Epub Jun. 17, 2009. (Year: 2009).*

Hansen et al., 2013. Pre-analytical sample treatment and DNA extraction protocols for the detection of bacterial pathogens from whole blood. PCR Detection of Microbial Pathogens: Second Edition, Methods in Molecular Biology, vol. 943, pp. 81-90. Humana Press, Totowa, NJ. (Year: 2013).*

Horz HP, Scheer S, Huenger F, Vianna ME, Conrads G. Selective isolation of bacterial DNA from human clinical specimens. J Microbiol Methods. Jan. 2008; 72(1):98-102. Epub Nov. 28, 2007. (Year: 2008).*

Kathuria et al., Multidrug-resistant Candida auris misidentified as Candida haemulonii: characterization by MALDI-TOF and DNA sequencing and its antifungal susceptibility profile variability by Vitek 2, CLSI broth microdilution, and Etest method. J Clin Microbiol. 2015;53:1823-30 (Year: 2015).*

Leach, L., Zhu, Y. and Chaturvedi, S., 2018. Development and validation of a real-time PCR assay for rapid detection of Candida auris from surveillance samples. Journal of clinical microbiology, 56(2), pp. e01223-17, pp. 1-7. (Year: 2018).*

Loonen et al., 2011. Acceleration of the direct identification of Staphylococcus aureus versus coagulase-negative Staphylococci from blood culture material: a comparison of six bacterial DNA extraction methods. European journal of clinical microbiology & infectious diseases, 30(3), pp. 337-342 (Year: 2011).*

Loonen et al., 2013. Comparison of pathogen DNA isolation methods from large vols. of whole blood to improve molecular diagnosis of bloodstream infections. PloS one, 8(8), p. e72349 pp. 1-7. (Year: 2013).*

McCann CD, Jordan JA. Evaluation of MolYsis™ Complete5 DNA extraction method for detecting Staphylococcus aureus DNA from whole blood in a sepsis model using PCR/pyrosequencing. J Microbiol Methods. Apr. 2014; 99:1-7. Epub Feb. 3, 2014. (Year: 2014).*

Mizusawa et al., Jan. 2017. Can multidrug-resistant Candida auris be reliably identified in clinical microbiology laboratories? Journal of clinical microbiology, 55(2), pp. 638-640. (Year: 2017).*

Nolling, Apr. 19, 2016. Duplex DNA-invading γ-modified peptide nucleic acids enable rapid identification of bloodstream infections in whole blood. MBio, 7(2), pp. e00345-16 pp. 1-11. (Year: 2016).*

SantaLucia Jr, John. Physical principles and visual-OMP software for optimal PCR design. PCR Primer Design. Humana Press, 2007: pp. 3-33. (Year: 2007).*

Feehery et al., 2013. A method for selectively enriching microbial DNA from contaminating vertebrate host DNA. PloS one, 8(10), p. e76096 pp. 1-13. (Year: 2013).*

Ben-Ami, R., Berman, J., Novikov, A., Bash, E., Shachor-Meyouhas, Y., Zakin, S., Maor, Y., Tarabia, J., Schechner, V., Adler, A. and Finn, T., 2017. Multidrug-resistant candida haemulonii and C. Auris, tel aviv, Israel. Emerging infectious diseases, 23(2), pp. 195-203. (Year: 2017).*

International Search Report and Written Opinion for PCT/US2018/025681 dated Jul. 19, 2018.

International Preliminary Report on Patentability for PCT/US2018/025681 dated Oct. 17, 2019.

Kuhn et al., Sequence specificity at targeting double-stranded DNA with a γ-PNA oligomer modified with guanidinium G-clamp nucleobases. Artif DNA: PNA & XNA. Jul.-Sep. 2010;1(1):45-53.

Leggieri et al., Molecular diagnosis of bloodstream infections: planning to (physically) reach the bedside. Curr Opin Infect Dis. Aug. 2010;23(4):311-9. doi: 10.1097/QCO.0b013e32833bfc44.

* cited by examiner

METHODS AND DEVICES FOR IDENTIFYING MICROBIAL INFECTIONS

RELATED APPLICATIONS

This application is a national stage filing under 35 U.S.C. § 371 of international application number PCT/US2018/025681, filed Apr. 2, 2018, which claims the benefit of U.S. Provisional Patent Application Ser. No. 62/480,953, filed Apr. 3, 2017, the entire contents of each of which are incorporated herein by reference.

GOVERNMENT SUPPORT

This invention was made with government support under contract Nos. R430D016466 and No. R44AI109913 awarded by the National Institutes of Health (NIH). The government has certain rights in the invention.

REFERENCE TO A SEQUENCE LISTING SUBMITTED AS A TEXT FILE VIA EFS-WEB

This application contains a Sequence Listing which has been submitted in ASCII format via EFS-Web and is hereby incorporated by reference in its entirety. Said ASCII copy, created on Sep. 30, 2019, is named H091670001US01-SEQ-JNL and is 116,990 bytes in size.

TECHNICAL FIELD

The present invention generally relates to the field of microbial pathogen detection and identification utilizing genomic sequence recognition.

BACKGROUND

Bloodstream infections (BSIs) have risen to become the 6th leading cause of death in the U.S. and the most expensive hospital-treated condition, at over $30B annually. BSIs account for 25% of all ICU usage and roughly 50% of all hospital deaths in the U.S. BSIs are typically caused by bacteria or fungi, and effective disease management requires their early and accurate identification. BSIs are typically identified through a series of blood-cultures that take up to several days to identify potential pathogens. Blood-cultures are widely considered the barrier to a hypothesis driven first-line antimicrobial intervention.

Modern molecular approaches have the potential to revolutionize this field, however limitations including lack of sensitivity, inaccurate performance, narrow coverage, and insufficient diagnostic detail have prevented these methods from making an impact. Indeed, in contrast to numerous infectious diseases, a clear capability gap remains despite the immense clinical need. It is the combined challenges of extremely low pathogen loads (1-100 CFU/ml), the requirement for broad coverage with high levels of detail (20 pathogens are responsible for roughly 90% of cases where species level information is clinically required), a difficult specimen matrix (blood), and the need for a rapid turnaround; all of which when combined, have proven difficult to overcome.

SUMMARY

The present disclosure generally relates to the field of microorganisms, e.g., microbial pathogens, detection and identification utilizing genomic sequence recognition. In particular, the claimed methods, devices, and kits provide for identification and evaluation of microorganisms in a sample, e.g., in blood, without the need for culturing the sample, or performing other manipulations of the sample that are likely to cause over- or under-representation of any one microbial species.

In some aspects, provided herein are methods of identifying one or more specific microbial species in a sample from a subject. The methods comprise: depleting eukaryotic DNA from the sample; lysing one or more microbial cells in the sample, wherein the lysing of one or more microbial cells releases a plurality of microbial genetic materials; isolating the plurality of microbial genetic materials; amplifying the plurality of microbial genetic materials; contacting the amplified microbial genetic materials with a plurality of DNA Invading Artificial Nucleic Acids (DIANAs), wherein the plurality of DIANAs comprise one or more sequences selected from the group consisting of SEQ ID NOs: 20-571; and detecting binding of one or more of the plurality of DIANAs to the microbial genetic material of its respective single species or group of microbes, wherein the detection of binding indicates the presence of one or more specific microbial species or groups of microbes in the sample.

In other aspects, provided herein are methods of identifying one or more specific microbial species in a sample from a subject. The methods comprise: depleting eukaryotic DNA from the sample; lysing one or more microbial cells in the sample, wherein the lysing of one or more microbial cells releases a plurality of microbial genetic materials; isolating the plurality of microbial genetic materials; amplifying the plurality of microbial genetic materials; incubating the amplified microbial genetic materials with a plurality of DNA Invading Artificial Nucleic Acids (DIANAs) for less than 10 minutes, and detecting binding of one or more of the plurality of DIANAs to the microbial genetic material of its respective single species or group of microbes, wherein the detection of binding indicates the presence of one or more specific microbial species or groups of microbes in the sample.

In some embodiments, the incubating the amplified microbial genetic materials with a plurality of DNA Invading Artificial Nucleic Acids (DIANAs) is at a temperature that is between about 20° C. to about 65° C. In some embodiments, the temperature is between about 20° C. to about 64° C. In some embodiments, the temperature is between about 30° C. to about 64° C. In some embodiments, the temperature is between about 37° C. to about 64° C. In some embodiments, the temperature is between about 40° C. to about 64° C. In some embodiments, the temperature is between about 50° C. to about 64° C. In some embodiments, the temperature is between about 37° C. to about 60° C. In some embodiments, the temperature is between about 40° C. to about 60° C. In some embodiments, the temperature is between about 50° C. to about 60° C.

In some embodiments, the amplified microbial genetic materials are incubated with a plurality of DNA Invading Artificial Nucleic Acids (DIANAs) in an incubation solution comprising a monovalent salt. In some embodiments, the monovalent salt is present at a concentration above 50 mM.

In some embodiments, the amplified microbial genetic materials are incubated with a plurality of DNA Invading Artificial Nucleic Acids (DIANAs) in an incubation solution comprising a divalent salt. In some embodiments, the divalent salt is present at a concentration above 5 mM.

In some embodiments, the amplified microbial genetic materials are incubated with a plurality of DNA Invading Artificial Nucleic Acids (DIANAs) in an incubation solution comprising a trivalent salt. In some embodiments, the trivalent salt is present at a concentration above 0.1 mM.

In some embodiments, the amplified microbial genetic materials are incubated with a plurality of DNA Invading Artificial Nucleic Acids (DIANAs) in an incubation solution having a pH between about 10.2 and about 12.2.

In other aspects, provided herein are methods of monitoring pathogen load of one or more specific microbial species over time in a subject. The methods comprise: measuring the pathogen load of the one or more specific microbial species in a first sample obtained from the subject at a first time and measuring the pathogen load in a second sample obtained from the subject at a second time, wherein the second sample is obtained from the subject at a time that is at least about 1 hour after the first sample was obtained from the subject, wherein eukaryotic DNA is depleted from the first sample and the second sample, one or more microbial cells is lysed in the first sample and the second sample, wherein the lysing of the one or more microbial cells releases a plurality of microbial genetic materials, the plurality of microbial genetic materials is isolated, the plurality of microbial genetic materials is amplified, the amplified microbial genetic materials are contacted with a plurality of DNA Invading Artificial Nucleic Acids (DIANAs), and binding of one or more of the plurality of DIANAs to the microbial genetic material of its respective single species or group of microbes is detected, wherein the detection of binding indicates the presence of one or more specific microbial species or groups of microbes in the sample.

In some embodiments, the second biological sample is obtained from the subject at least about 1, 2, 3, 4, 5, 6, 7, 8, 9, 10, 11, or 12 hours after the first biological sample was obtained from the subject.

In other aspects, provided herein are methods of determining susceptibility of one or more specific microbial species in a subject to one or more antimicrobials. The methods comprise: obtaining one or more samples from the subject, optionally dividing any one or more of the one or more samples into multiple samples; measuring the pathogen load of the one or more specific microbial species in one of the one or more samples obtained from the subject or in one of the multiple samples; incubating at least one of the one or more samples obtained from the subject or incubating at least one of the multiple samples with the one or more antimicrobials for at least 1 hour to obtain a sample treated with one or more antimicrobials; and measuring the pathogen load of the one or more specific microbial species in the sample treated with the one or more antimicrobials, wherein the pathogen load of the one or more specific microbial species in the sample incubated with the one or more antimicrobials is used to determine antimicrobial susceptibility of the pathogen.

In some embodiments, the multiple samples equals 2, 3, 4, 5, or 6 or more samples. In some embodiments, the one or more antimicrobials are selected from ampicillin, amoxycillin, aureomicin, bacitracin, ceftazidime, ceftriaxone, cefotaxime, cephachlor, cephalexin, cephradine, ciprofloxacin, clavulanic acid, cloxacillin, dicloxacillan, erythromycin, flucloxacillan, gentamicin, gramicidin, methicillan, neomycin, oxacillan, penicillin, vancomycin, capsofungin, flucytosine, fluconazole, itraconazole, ketoconazole, and miconazole.

In some embodiments, the antimicrobial selected is an antibiotic. In some embodiments, the antibiotic selected may be a compound relating to the following antibiotic classes selected from penicillins, tetracyclines, cephalosporins, quinolones, lincomycins, macroslides, sulfomides, glycopeptides, aminoglycosides, and/or carapenems. In some embodiments, the antibiotic selected may be selected from an alternative class of antibiotics.

In some embodiments, the antimicrobial selected is an antifungal. In some embodiments, the antifungal selected may be a compound relating to the following antifungal classes selected from azoles, allylamines, echinocandins, nucleoside analogs, and/or polyenes. In some embodiments, the antifungal selected may be selected from an alternative class of antifungals.

In other aspects, provided herein are methods of identifying which microbial species of a group of microbial species in a sample from a subject having an infection contains genetic material which confers resistance or reduced susceptibility to antimicrobials. The methods comprise: depleting eukaryotic DNA from the sample; lysing one or more microbial cells in the sample, wherein the lysing of one or more microbial cells releases a plurality of microbial genetic materials; isolating the plurality of microbial genetic materials; amplifying the plurality of microbial genetic materials; contacting the amplified microbial genetic materials with a plurality of DNA Invading Artificial Nucleic Acids (DIANAs) that bind to a single species or group of microbes, wherein the plurality of DIANAs comprise a sequence selected from the group consisting of SEQ ID NOs: 1-4 and 20-31; contacting the amplified microbial genetic materials with a plurality of DNA Invading Artificial Nucleic Acids (DIANAs) that bind to microbial genetic material which confers resistance or reduced susceptibility to antimicrobials, wherein the plurality of DIANAs comprise a sequence selected from the group consisting of SEQ ID NOs: 141-493;

detecting and quantifying binding of one or more of the plurality of DIANAs to the microbial genetic material of its respective single species or group of microbes and detecting binding of one or more of the plurality of DIANAs to the microbial genetic material which confers resistance or reduced susceptibility to antimicrobials; and determining the stoichiometry between the signal obtained from the detected single species or group of microbes and the signal obtained from the detected genetic material which confers resistance or reduced susceptibility to antimicrobials; wherein the stoichiometry is used to determine which microbial species contains the genetic material that confers resistance or reduced susceptibility to antimicrobials.

In other aspects, provided herein are methods of identifying a single species or group of microbes which is associated with endocarditis and/or sepsis in a subject. The methods comprise: depleting eukaryotic DNA from the sample; lysing one or more microbial cells in the sample, wherein the lysing of one or more microbial cells releases a plurality of microbial genetic materials; isolating the plurality of microbial genetic materials; amplifying the plurality of microbial genetic materials; contacting the amplified microbial genetic materials with a plurality of DNA Invading Artificial Nucleic Acids (DIANAs) that bind to the single species or group of microbes associated with endocarditis and/or sepsis, wherein the plurality of DIANAs comprise one or more sequences selected from the group consisting of SEQ ID NOs: 20-131; and detecting binding of the one or more of the plurality of DIANAs to the microbial genetic material of its respective single species or group of microbes, wherein the detection of binding indicates the presence of the one or more specific microbial species or groups of microbes associated with endocarditis and/or sepsis in the sample.

In other aspects, provided herein are methods of identifying a single species or group of microbes which is associated with neonatal sepsis in a subject. The methods comprise: depleting eukaryotic DNA from the sample; lysing one or more microbial cells in the sample, wherein the lysing of one or more microbial cells releases a plurality of microbial genetic materials; isolating the plurality of microbial genetic materials; amplifying the plurality of microbial genetic materials; contacting the amplified microbial genetic materials with a plurality of DNA Invading Artificial Nucleic Acids (DIANAs) that bind to the single species or group of microbes associated with neonatal sepsis, wherein the plurality of DIANAs comprise one or more sequences selected from the group consisting of SEQ ID NOs: 132-140; and detecting binding of the one or more of the plurality of DIANAs to the microbial genetic material of its respective single species or group of microbes, wherein the detection of binding indicates the presence of the one or more specific microbial species or groups of microbes associated with neonatal sepsis in the sample.

In some embodiments, the sample has a volume of between 0.1 and 1 ml. In some embodiments, the sample has a volume of between 0.5 and 2.0 ml.

In other aspects, provided herein are methods of identifying a genetic material which confers reduced susceptibility or resistance to antimicrobials in a pathogen in a subject. The methods comprise: depleting eukaryotic DNA from the sample; lysing one or more microbial cells in the sample, wherein the lysing of one or more microbial cells releases a plurality of microbial genetic materials; isolating the plurality of microbial genetic materials; amplifying the plurality of microbial genetic materials; contacting the amplified microbial genetic materials with a plurality of DNA Invading Artificial Nucleic Acids (DIANAs) that bind to genetic material which confers reduced susceptibility or resistance to antimicrobials, wherein the plurality of DIANAs comprise one or more sequences selected from the group consisting of SEQ ID NOs: 141-493; and detecting binding of the one or more of the plurality of DIANAs to the microbial genetic material, wherein the detection of binding indicates the presence of the genetic material which confers reduced susceptibility or resistance to antimicrobials in a pathogen in the sample.

In other aspects, provided herein are methods of of identifying a fungal species or groups of fungi in a subject. The methods comprise: depleting eukaryotic DNA from the sample; lysing one or more microbial cells in the sample, wherein the lysing of one or more microbial cells releases a plurality of microbial genetic materials; isolating the plurality of microbial genetic materials; amplifying the plurality of microbial genetic materials; contacting the amplified microbial genetic materials with a plurality of DNA Invading Artificial Nucleic Acids (DIANAs), wherein the plurality of DIANAs comprise one or more sequences selected from the group consisting of SEQ ID NOs: 494-571; and detecting binding of one or more of the plurality of DIANAs to the microbial genetic material of its respective single fungal species or group of fungi, wherein the detection of binding indicates the presence of the one or more specific fungal species or groups of fungi in the sample.

In another aspect, also provided herein are compositions comprising one or more DIANAs comprising a sequence selected from the group consisting of SEQ ID NOs: 20-571.

In a further aspect, also provided herein are kits comprising one or more DIANAs, wherein the DIANAs comprise one or more sequences selected from the group consisting of SEQ ID NOs: 20-571.

In some embodiments, one or more of the plurality of DIANAs is modified to comprise one or more binding moieties. In some embodiments, the one or more binding moieties are non-covalent binding moieties. In some embodiments, the one or more binding moieties are covalent binding moieties.

In some embodiments, one or more of the plurality of DIANAs comprise a linker.

In some embodiments, one or more of the plurality of DIANAs further comprises a spacer.

In some embodiments, the sample is a blood sample. In some embodiments, the blood sample is a whole blood sample.

In other aspects, provided herein are methods for identifying one or more specific microbial species in a sample from a subject. The methods comprise: applying the sample to a fluidic device comprising: a sample inlet; a fluidic channel in fluidic communication with the sample inlet, wherein the fluidic channel has a length of at least 1 cm and a channel length-to-width ratio of at least 5:1; a first lysis region in fluidic communication with the fluidic channel; a first isolation region in fluidic communication with first lysis region; a second lysis region in fluidic communication with the first isolation region; a second isolation region in fluidic communication with the second lysis region; at least one reaction region in fluidic communication with the second isolation region; an amplification region in fluidic communication with at least one of the reaction regions; a plurality of processing chambers, each in fluidic communication with at least one of the reaction regions and/or the amplification region; and one or more detection regions, wherein the detection regions comprise one or more DNA Invading Artificial Nucleic Acids (DIANAs) comprising one or more sequences selected from the group consisting of SEQ ID NOs: 20-571.

In some embodiments, the methods comprise a detection region in fluidic communication with each processing chamber.

In some embodiments, the fluidic device has n detection regions and is capable of identifying n+x specific microbial species, and wherein x is greater than or equal to 1.

In other aspects, provided herein are methods for identifying one or more specific microbial species in a sample from a subject. The methods comprise: applying the sample to a fluidic device comprising: a fluidic reservoir; a gas chamber in fluidic communication with the fluidic reservoir; a fluidic channel in fluidic communication with the fluidic reservoir; and one or more detection regions, wherein the detection regions comprise one or more DNA Invading Artificial Nucleic Acids (DIANAs) comprising one or more sequences selected from the group consisting of SEQ ID NOs: 20-571, wherein a longitudinal axis of the fluidic reservoir is substantially perpendicular to a longitudinal axis of the fluidic channel, performing the steps of: introducing a first fluid in the fluidic reservoir, wherein the first fluid is a liquid; introducing a second fluid in the gas chamber, wherein the second fluid is a gas; and applying a pressure to the second fluid such that the second fluid flows from the gas chamber to the fluidic reservoir and pushes the first fluid from the fluidic column into the fluidic channel, wherein binding of the one or more DIANAs to the sample indicates the presence of one or more specific microbial species or groups of microbes in the sample.

In some embodiments, the methods comprise flowing a first fluid having a volume of at least 0.1 mL into the fluidic reservoir via the fluidic channel.

In some embodiments, the methods comprise introducing a stream or bubbles of a gas in the fluidic reservoir to cause the first fluid and the reagent to mix, wherein the gas is transported from the fluidic channel.

In some embodiments, the methods comprise flowing the gas from the fluidic reservoir into the gas chamber and substantially inhibiting the first fluid and/or the reagent from flowing into the gas chamber.

In some embodiments, the fluidic device has n detection regions and is capable of identifying n+x specific microbial species, and wherein x is greater than or equal to 1.

In some embodiments, the subject is a mammal, e.g., a human. In some embodiments, the subject is suspected of having an infection, e.g., a bacterial or fungal infection.

In another aspect, provided herein are fluidic devices comprising one or more processing chambers and one or more detection regions, wherein one or more DNA Invading Artificial Nucleic Acids (DIANAs) comprising one or more sequences selected from the group consisting of SEQ ID NOs: 20-571 are contained within at least one of the detection regions.

In some embodiments, each fluidic reservoir has a volume of at least 0.1 mL.

In some embodiments, each gas chamber is in fluidic communication with a fluidic reservoir.

In some embodiments, each gas chamber has a volume of at least 0.1 mL.

In some embodiments, each fluidic channel is in fluidic communication with one or more fluidic reservoirs.

In some embodiments, each fluidic channel has a volume of less than 2000 µL.

In some embodiments, a longitudinal axis of at least one fluidic reservoir is substantially perpendicular to a longitudinal axis of at least one fluidic channel having a length of at least 1 cm.

In some embodiments, the fluidic channel has a length of at least 1 cm.

In some embodiments, the fluidic channel has a channel length-to-width ratio of at least 5:1.

In some embodiments, a fluidic device described herein comprises at least 10 branching channels branching from the fluidic hub.

In some embodiments, a fluidic device described herein comprises a plurality of valves, each valve positioned between the branching channels and the fluidic hub.

In some embodiments, a fluidic device described herein comprises a plurality of fluidic reservoirs, each fluidic reservoir connected to a branching channel.

In some embodiments, one or more of the plurality of DIANAs is modified to comprise one or more binding moieties. In some embodiments, the one or more binding moieties are non-covalent binding moieties. In some embodiments, the one or more binding moieties are covalent binding moieties.

In some embodiments, one or more of the plurality of DIANAs comprise a linker.

In some embodiments, one or more of the plurality of DIANAs further comprises a spacer.

In some embodiments, the sample is a blood sample. In some embodiments, the blood sample is a whole blood sample.

In another aspect, a kit is provided comprising reagents and protocols for detecting and/or identifying and/or evaluating one or more microorganisms from a sample without prior enrichment. In some embodiments, this kit contains reagents and protocols for the following processes: (i) depleting eukaryotic DNA from the sample; (ii) lysing one or more microbial cells in the sample, wherein the lysing of one or more microbial cells releases a plurality of microbial genetic materials; (iii) isolating the plurality of microbial genetic materials; (iv) amplifying the plurality of microbial genetic materials; and (v) contacting the amplified microbial genetic materials with a plurality of DNA Invading Artificial Nucleic Acids (DIANAs) that bind to the single species or group of microbes associated with a bloodstream infection, wherein the plurality of DIANAs comprise one or more sequences selected from the group consisting of SEQ ID NOs: 20-571; and (vi) detecting binding of the one or more of the plurality of DIANAs to the microbial genetic material of its respective single species or group of microbes, wherein the detection of binding indicates the presence of the one or more specific microbial species or groups of microbes associated with bloodstream infections in the sample.

In some embodiments, a kit may be able to provide both the load (relative and/or absolute) and microbial composition of the sample (herein defined as 'microbial spectra') should more than a single microorganism be present in the sample.

Other advantages and novel features of the methods, devices, and kits described herein will become apparent from the following detailed description of various non-limiting embodiments when considered in conjunction with the accompanying figures. In cases where the present specification and a document Incorporated by reference include conflicting and/or inconsistent disclosure, the present specification shall control.

BRIEF DESCRIPTION OF THE FIGURES

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1:
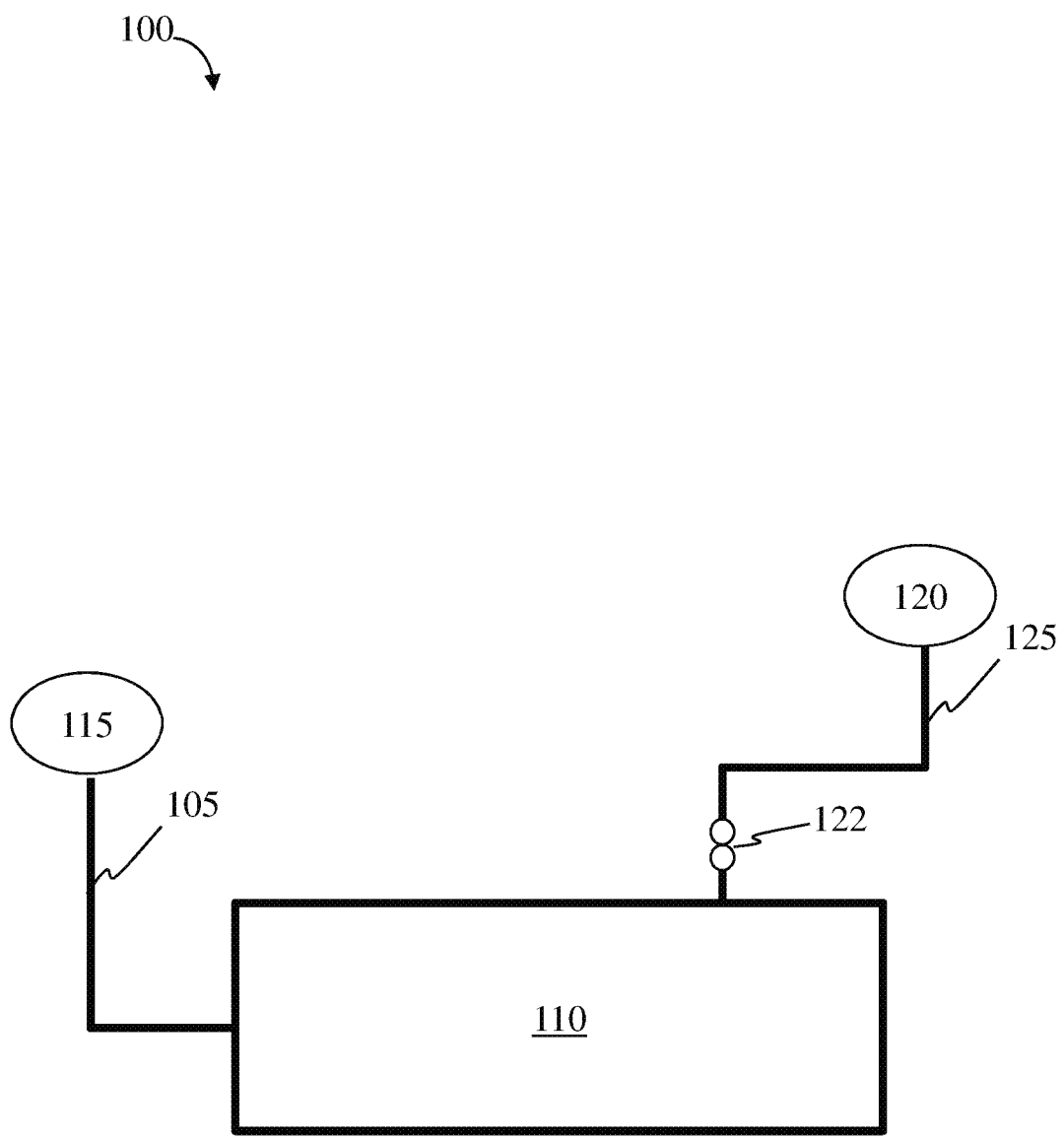
FIG. 1 is a schematic illustration of a fluidic device, according to one set of embodiments.

Described herein are methods, devices, and kits for detecting, identifying, monitoring, and evaluating microorganisms, e.g., pathogens, in a sample from a subject by detecting the genetic material of the microorganisms. These methods, devices, and kits employ DNA Invading Artificial Nucleic Acids (DIANAs) and novel DIANAs are disclosed herein. Whereas art known methods rely on hybridization to detect microbial DNA, which has difficulty discriminating among highly similar sequences with high confidence, DIANAs have specificity down to single base-pair resolution, allowing the differentiation of highly homologous sequences.

These methods, devices and kits are particularly useful in evaluating microorganisms present at low levels in a sample. Methods in the art commonly use culturing to increase microbial levels. Major drawbacks of culturing are that it takes time for the microorganisms to grow to sufficient concentrations, and that different species of microorganisms in a population may have different growth rates, such that information concerning the relative frequency of different species of microorganisms in a population may be lost. Indeed, some microorganisms are not culturable and may not be detected in techniques using culturing.

The claimed methods, devices, and kits not only allow for the identification of microorganisms present at low levels, but they also allow for the identification of microbial spectra—the types and relative amounts or loads of different microorganisms present in a sample. Moreover, this identification can be highly detailed and can include the identification of microorganisms and their resistance conferring genes from a broad range of species simultaneously. Further, the methods can provide this information quickly.

The methods, devices, and kits are particularly useful in the context of evaluating blood samples and evaluating subjects for the presence or progression of blood stream infections (BSIs), e.g., sepsis, infective endocarditis, and neonatal sepsis. Whole blood is a complex solution that contains multiple cell types such as leukocytes, erythrocytes, and thrombocytes, as well as naturally occurring organic and inorganic components. The blood components can hinder (and may even completely prevent) additional or downstream processing of DNA and/or RNA, such as, e.g., enzymatic PCR or isothermal amplification. Additionally, anticoagulants and preservatives, which are commonly used during bodily fluid sample collection, can further interfere with enzymatic or other process. Assaying blood can also require large volumes due to the low frequency (low loads) of microorganisms in BSIs. The methods, devices, and kits described herein provide for sensitive and accurate evaluation of microorganisms in blood samples. As is described herein, the methods, devices, and kits are particularly useful for identifying microorganisms associated with bloodstream infections in general, and specifically infectious endocartidis and/or neonatal sepsis and/or fungal infections in the blood.

The methods, kits, and devices described herein may be useful, for example, for clinical purposes (e.g., diagnosing a disease or aliment via the presence of specific pathogen), or for research purposes (e.g., for monitoring the changes in microbial spectra within a sample over time due to the addition and/or administration of a compound). Because the approach described herein, among other things, can be fully integrated (i.e., is sample-in/results-out), does not require culturing, and uses DIANAs, it offers significant performance advantages over the art including, for example, improved kinetics, sensitivity, specificity, dynamic range, and the ability to detect the relative amounts of different microorganisms.

The various aspects and embodiments of the present technology that are introduced above and discussed in greater detail below may be implemented in any number of ways, and as described herein, are not limited to any particular manner of implementation. Examples of specific implementations and applications are provided primarily for illustrative purposes. As used herein, the singular forms "a," "an," and "the" include plural referents unless the content clearly dictates otherwise. For example, reference to "a cell" includes a combination of two or more cells, and the like.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same DNA Invading Artificial Nucleic Acids (DIANAs)

In some embodiments, DNA Invading Artificial Nucleic Acids (DIANAs) are used to detect microbial genetic materials.

DIANA-based invasion can be fast and can require only minutes. This is in contrast to techniques using DNA or RNA hybridization probes, which can require hours to reach high stringency. DIANAs also can have unmatched specificity, down to single base pair resolution, leading to a more accurate process than DNA or RNA hybridization. Without wishing to be bound by theory, the physical rationale behind this specificity is as follows. During invasion, a localized 'bubble' within the duplex DNA is formed, allowing the DIANA oligomer to bind to a specific sequence along one of the two DNA strands. Throughout, the DNA complement to that sequence remains on the opposing strand, as the DNA is not denatured. Thus, if a single mismatch between the DNA and the DIANA probe is evident, the opposing strand can 'snap-back' and 'kick-out' the DIANA. It is this consistent and localized energetic battle between the DIANA oligomer and the DNA complement which make the invasion process immensely specific.

As used herein, the term "invasion" refers to the binding of DIANAs to microbial genomic material (e.g., RNA or DNA). Similar to that which is common in the field of molecular biology, sequence recognition is through Watson-Crick basepairing rules, while not ruling out alternative mechanisms such as, but not limited to, Hoogstein and reverse-Hoogstein base-pairing rules. In some embodiments, the DIANA binds to double stranded DNA or RNA. In some embodiments, the DIANA binds to a predominantly single-stranded DNA or RNA. It is to be understood that the process of DIANA invasion to a DNA or RNA molecule may take place despite the DNA and/or RNA being predominantly single-stranded due to the presence of secondary structures, such as, but not limited, to hairpins. It is to be understood that the process of 'invasion' is localized, and the local conditions are those which dictate whether the process is inherently hybridization or invasion based.

In some embodiments, the DIANAs take the form of a specialized type or class of Peptide Nucleic Acids (PNAs). In some embodiments, the DIANAs are not limited to a specific class of PNAs. In some embodiments, the DIANAs take the form of a specialized type or class of Locked or Bridged Nucleic Acids (LNAs and/or BNAs). In some embodiments, DIANAs that locally invades duplex DNA have the required affinity and sequence specificity to be used in the methods disclosed herein.

In some embodiments, PNA oligomer based DIANAs have a chiral stereo-center at the gamma-position of the backbone (also known as γPNA). γPNAs are oligomers, comprised of monomers which make up the sequence composition for that oligomer. By way of example by not by way of limitation, the γPNA oligomer with a sequence AGTCAG will be comprised for two 'A' monomers, two 'G' monomers, a single 'T' monomer, and a single 'C' monomer. A γPNA oligomer is a specific class of PNA oligomer wherein at least a single monomer contains a chiral stereo-center at the gamma-position of the monomer backbone (herein a 'gamma-modified monomer'). A PNA oligomer that is pre-oriented structurally into a right-handed helix is energetically favored to perform duplex DNA invasion. In some embodiments, the microbial DNA is detected using γPNA as taught in WO 2013/176992, the contents of which are incorporated by reference in its entirety. In some embodiments, use of DIANAs is advantageous for long amplicons (e.g., amplicons between about 400 to 4000 bp). It is to be understood, that DIANAs, in some embodiments, could be used in DNA/RNA hybridization processes. However, we identify improved performance when experimental conditions are those which favor invasion in-place of hybridization.

In some embodiments, the oligomer contains more than 5% gamma-modified monomers, more than 10% gamma-modified monomers, more than 25% gamma-modified monomers, more than 50% gamma-modified monomers, more than 75% gamma-modified monomers, or 100% gamma-modified monomers. Suitable modifications at the gamma-site are well known to those skilled in the art and include by way of example, but not by way of limitation, non-polar groups such as methyl groups, ethyl group, etc, or polar groups such as ethylene glycol-based groups, or semi-polar groups, such as those which are ester based.

In some embodiments, the DIANA target genetic material from a microorganism. In some embodiments, the DIANA targets genetic material from a bacteria, e.g., a Gram positive or a Gram negative bacteria. In some embodiments, the DIANA targets genetic material from a fungi. In some embodiments, the oligomer sequences for DIANAs useful in microbial identification are as shown in Table 1, Table 2, Table 3, Table 4, or Table 5, below:

Table 1 Shows DIANA Sequences for Identifying Microorganisms

TABLE 1

| Microorganism | SeqID | DIANA Sequence |
| --- | --- | --- |
| Staphylococcus aureus | SeqID-001 | AACGGACGAGAAGCT |
| Coagulase Negative Staphylococci | SeqID-002 | GTAACCATTTGGAGCT |
| | SeqID-003 | GTAACCATTTATGGAG |
| Enterococcus faecalis | SeqID-004 | GGACGTTAGTAACTGAA |

TABLE 1-continued

| Microorganism | SeqID | DIANA Sequence |
| --- | --- | --- |
| Streptococcus pneumoniae | SeqID-005 | TTAACCATAGTAGGCC |
| Streptococcus agalactiae | SeqID-006 | AAGAGTAATTAACACAT |
| Streptococcus pyogenes | SeqID-007 | ATAAGAGAGACTAACG |
| Enterococcus faecium | SeqID-008 | GGATGAGAGTAACTGTT |
| Enterobacter spp./ Klebsiella spp. | SeqID-009 | CACAGAGAGCTTGCTC |
| Pseudomonas aeruginosa | SeqID-010 | TGAGATCATAGTGGCGC |
| | SeqID-011 | TGAGATCTTAGTGGCGC |
| Acinetobacter baumannii | SeqID-012 | TACCTAGAGATAGTGG |
| Serratia marcescens | SeqID-013 | AAGGTGGTGAACTTAA |
| | SeqID-014 | AAGGTGGTGAGCTTAA |
| Candida albicans | SeqID-015 | GGGTAGCCATTTATG |
| Candida parapsilosis | SeqID-016 | ACGCATCAAAAAAGAT |
| Candida krusei | SeqID-017 | CCGTGGAAAATCTAG |
| Candida glabrata | SeqID-018 | CGTGTACTGGAATGCA |
| Candida tropicalis | SeqID-019 | CAATGTCTTCGGACT |

Table 2 Shows DIANA Sequences for Identifying Microorganisms Commonly Associated with Infective Endocarditis

TABLE 2

| Microorganism | Seq ID | DIANA Sequence |
| --- | --- | --- |
| Coagulase Negative Staphylococci | SeqID-020 | AGCGAACAGACGAGGAGCTT |
| | SeqID-021 | CGAGGAGCTTGCTCCTCTGA |
| | SeqID-022 | GCTCCTCTGACGTTAGCGGC |
| | SeqID-023 | AGCGAACAGATAAGGAGCTT |
| | SeqID-024 | TAAGGAGCTTGCTCCTTTGA |
| | SeqID-025 | GCTCCTTTGACGTTAGCGGC |
| | SeqID-026 | AATACCGGATAATATATTGA |
| | SeqID-027 | GGATAATATATTGAACCGCA |
| | SeqID-028 | TATATTGAACCGCATGGTTC |
| | SeqID-029 | AATACCGGATAATATGTTGA |
| | SeqID-030 | GGATAATATGTTGAACCGCA |
| | SeqID-031 | TATGTTGAACCGCATGGTTC |
| Eikenella corrodens | SeqID-032 | GGTAGTGCTTGCACTACTGT |
| | SeqID-033 | GCTTGCACTACTGTCCGGCG |
| | SeqID-034 | ACTACTGTCCGGCGAGTGGC |
| | SeqID-035 | TGTAAAGTACTTTTGTTAGG |
| | SeqID-036 | GGAAGAAAAGGGAAGTGCTA |
| | SeqID-037 | AAAGGGAAGTGCTAATACCA |
| | SeqID-038 | AAGTGCTAATACCACTTTTT |
| Kingella kingae | SeqID-039 | GTTATTCGAGCGGCCAATAA |
| | SeqID-040 | CGAGCGGCCAATAACTGATT |
| | SeqID-041 | GCCAATAACTGATTAGCTAG |
| | SeqID-042 | TTTGTTAGGGAAGAAAAGGT |
| | SeqID-043 | AGGGAAGAAAAGGTTGATGC |
| | SeqID-044 | GAAAAGGTTGATGCTAATAT |
| | SeqID-045 | CAGACGGTTAGTTAAGCAAG |
| Aggregatibacter actinomycetemcomitans | SeqID-046 | TAGCAGGTAAGTACTTGTAC |
| | SeqID-047 | TTCGGTGATGAGGAAGGTTG |
| | SeqID-048 | TTTAGCCCTGGTGCCCGAAG |
| | SeqID-049 | CTTGACATCCGAAGAAGAAC |
| | SeqID-050 | AGAGGGTAACCAACCAGCGA |

TABLE 2-continued

| Microorganism | Seq ID | DIANA Sequence |
|---|---|---|
| Haemophilus parainfluenzae | SeqID-051 | AAGGCATTTAGTTTAATAGA |
| | SeqID-052 | GTTGAGCTTTAAGTTTGGCG |
| Haemophilus influenzae | SeqID-053 | CGGAAGATGAAAGTGCGGGA |
| | SeqID-054 | ATGAAAGTGCGGGACTGAGA |
| | SeqID-055 | GTGCGGGACTGAGAGGCCGC |
| | SeqID-056 | ATGTGTTAATAGCACATCAA |
| | SeqID-057 | TAATAGCACATCAAATTGAC |
| | SeqID-058 | CACATCAAATTGACGTTAAA |
| Viridans streptococci | SeqID-059 | CATGTTAGATGCTTGAAAG |
| | SeqID-060 | CTCTGTTGTAAGAGAAGAAC |
| | SeqID-061 | TGTGAGAGTGGAAAGTTCA |
| | SeqID-062 | TGTGAGAATGGAAAGTTCA |
| | SeqID-063 | AGGTGTTAGGTCCTTTCCGG |
| Bartonella spp. | SeqID-064 | CACTCTTTTAGAGTGAGCGG |
| | SeqID-065 | GATCGCGGAAGGTGGAGACA |
| | SeqID-066 | GGAAGGTGGAGACACCCTCC |
| | SeqID-067 | TGGAGACACCCTCCTTCAGT |
| | SeqID-068 | AATGAAATGGACCCACCCCT |
| | SeqID-069 | ACGGCGTCATAATGCGCCAA |
| | SeqID-070 | AATTTCTATTTTCAAAAAAA |
| | SeqID-071 | AGGTCCATGAAAGATATTAA |
| | SeqID-072 | TGGGTGTTGATATTGCAAAA |
| | SeqID-073 | TTTTCAACTGTGTGGAATTG |
| | SeqID-074 | TGGGGTAAAGTGATCTACAC |
| | SeqID-075 | GGGTTAAGCGTGCTCAGTAT |
| | SeqID-076 | CACCGTAGCCAGTCTTAAGG |
| | SeqID-077 | TGCGTGGTGATGGAAGCGTG |
| | SeqID-078 | GAGCGAACCATTGGTATCGG |
| | SeqID-079 | TATGGGGATGGGTATCCCAA |
| | SeqID-080 | TTGATCAGTCCGCAGCACGT |
| | SeqID-081 | CGTATGTCAAAAGTAACAAG |
| | SeqID-082 | TCGTAACGATGCGCAGGCGA |
| | SeqID-083 | GAAGCGGCTTCCCGCGCCTC |
| | SeqID-084 | GGTTTGTGCGGGGTAAAACG |
| | SeqID-085 | ACAACAAGACGTTCAAGCGC |
| | SeqID-086 | AAGATACGCGATCGTTTAGT |
| | SeqID-087 | GCCGCACGGCGCTGATCAAT |
| | SeqID-088 | TCGGGGGTTGTTGCAAGAAT |
| | SeqID-089 | CTCACGATGGCGCGTGGTGC |
| | SeqID-090 | GATTTTATGAAGAGCTCCCG |
| | SeqID-091 | TTTAGCGAGCGAAGCGGTGG |
| | SeqID-092 | ACACCGCGGATGAAACGGGT |
| | SeqID-093 | ATTGTTTGTATACCGAATTG |
| | SeqID-094 | CCGGGACGAAGCGATTGGTG |
| | SeqID-095 | GAGGAGGAATTAAAAGCGGT |
| | SeqID-096 | AAGCCAATGAGGATTGTCAA |
| | SeqID-097 | ACAGAGCATCCCGGGGGTGG |
| | SeqID-098 | TTAACGGCGCTCTCGGTTTA |
| | SeqID-099 | GCGTGGGTGACATTCATCAA |
| | SeqID-100 | TCGTTCCCGGCAGTTGTCGG |
| | SeqID-101 | ATTGGGTTGGTCCCTCGACA |
| | SeqID-102 | CGAGTGGGAATAAGGAGGTG |
| Coxiella burnetii | SeqID-103 | GGGGATTAGTAAACGCGGCA |
| | SeqID-104 | ATGTTAAGGACGTTATTGAT |
| | SeqID-105 | GCGCCCCGTGCGCTATTGCGT |
| | SeqID-106 | AAAAAATAAAACGGATAAAA |
| | SeqID-107 | CTGTGGTTAAAAGCACTCAT |
| | SeqID-108 | GCCGCGGAATGAATCGCGCT |
| | SeqID-109 | GGCGTTAGCGAATAAAAATG |
| | SeqID-110 | ATCATTTGGGCGCTTTTAAC |
| | SeqID-111 | AAGAAACGTATCGCTGTGGC |
| | SeqID-112 | AACACCGCCGTGGGTAAAAA |
| | SeqID-113 | ATTAACAAAAGGAGACACAC |
| | SeqID-114 | GAGTTCGAAACAATGAGGGC |
| | SeqID-115 | AAAGTAAGGTAAAACCTGAG |
| | SeqID-116 | TTAAGCTGATTCATACGGTG |
| | SeqID-117 | GTGAAGCCGATAGCCCGATA |
| | SeqID-118 | CAACCTTGCATAATTCATCA |
| | SeqID-119 | CCAATGGTGGCCAATTTAAA |
| | SeqID-120 | ATGCCGGATATACGAATGCA |
| | SeqID-121 | TTTCTTTTCATCAAAACTGA |

TABLE 2-continued

| Microorganism | Seq ID | DIANA Sequence |
|---|---|---|
| | SeqID-122 | GACAACAAGGGTGGGTCCAT |
| | SeqID-123 | TATGCAGCGAAGCGGAATAC |
| | SeqID-124 | TGAAATCATTTTCTCCGTAT |
| Cardiobacterium hominis | SeqID-125 | GAACGGAAACGATGGAGCTT |
| | SeqID-126 | AAACGATGGAGCTTGCTCCA |
| | SeqID-127 | TGGAGCTTGCTCCAGGCGTC |
| | SeqID-128 | TTGCTCCAGGCGTCGAGTGG |
| | SeqID-129 | TGGGAATCTGCCTTTTGCTG |
| | SeqID-130 | TCTGCCTTTTGCTGGGGGAT |
| | SeqID-131 | TTTTGCTGGGGGATAACGTA |

Table 3 shows DIANA sequences for identifying microorganisms commonly associated with Neonatal Sepsis

TABLE 3

| Microorganism | Seq ID | DIANA Sequence |
|---|---|---|
| Listeria monocytogenes | SeqID-132 | TAATACCGAATGATAAAGTG |
| | SeqID-133 | CGAATGATAAAGTGTGGCGC |
| | SeqID-134 | ATAAAGTGTGGCGCATGCCA |
| | SeqID-135 | TGTGGCGCATGCCACGCTTT |
| | SeqID-136 | GCATGCCACGCTTTTGAAAG |
| | SeqID-137 | CACGCTTTTGAAAGATGGTT |
| Neisseria meningitidis | SeqID-138 | AGGCTGTTGCTAATATCAGC |
| | SeqID-139 | TAATATCAGCGGCTGATGAC |
| Escherichia coli | SeqID-140 | GCATCTGATACTGGCA |

Table 4 Shows DIANA Sequences Commonly Associated with Antimicrobial Resistance

TABLE 4

| Target | Seq ID | DIANA Sequence |
|---|---|---|
| Gene(s) conferring resistance to antistaphylococcal | SeqID-141 | TGTCACTTTCAACATACAAT |
| | SeqID-142 | TGAAGAAATTGTATTTAAGG |
| | SeqID-143 | GTAACAGCACTTATTAATAA |
| | SeqID-144 | AATAAAACAGTGAAGCAACC |
| | SeqID-145 | TACGGATTGCTTCACTGTTT |
| | SeqID-146 | TTCATCTATATCGTATTTTT |
| | SeqID-146 | CCGTTCTCATATAGCTCATC |
| | SeqID-148 | CTTTACCTGAGATTTTGGCA |
| | SeqID-149 | GCTAGCCATTCCTTTATCTT |
| | SeqID-150 | TCTTTAACATTAATAGCCAT |
| | SeqID-151 | TGTTTGGATTATCTTTATCA |
| | SeqID-152 | TATAAACCACCCAATTTGTC |
| | SeqID-153 | GTTTCTCCTTGTTTCATTTT |
| | SeqID-154 | CTGCAGTACCGGATTTGCCA |
| | SeqID-155 | GTTTGCATAAGATCTATAAA |
| | SeqID-156 | TCTTTATGTGTTTTATTTAC |
| | SeqID-157 | TGTTTGGATTATCTTTATCA |
| | SeqID-158 | GTTGCATACCATCAGTTAAT |
| | SeqID-159 | GATATTTCTTTGGAAATAA |
| | SeqID-160 | TTCTTCCAAACTTTGTTTTT |
| | SeqID-161 | CTTTTAATAAGTGAGGTGCG |
| | SeqID-162 | ATTGCCATTATTTTCTAATG |
| | SeqID-163 | TAGATTGAAAGGATCTGTAC |
| | SeqID-164 | TAATCAGTATTTCACCTTGT |
| | SeqID-165 | ACCTGAATCAGCTAATAATA |
| | SeqID-166 | TTATCTAAATTTTTGTTTGA |
| | SeqID-167 | GAGCATTATAAAATGGATAA |
| | SeqID-168 | TGGTATATCTTCACCAACAC |
| | SeqID-169 | TTTTTCATGCCTTTTTCAAA |
| | SeqID-170 | TACTGCCTAATTCGAGTGCT |
| | SeqID-171 | AGCAAAGAAAATGTTATCTG |
| | SeqID-172 | TCTATTGCTTGTTTTAAGTC |
| | SeqID-173 | TACCATTTACCACTTCATAT |
| | SeqID-174 | AACGTTGTAACCACCCCAAG |
| | SeqID-175 | TCTTTTTGCCAACCTTTACC |
| | SeqID-176 | TTTTATAACTTGTTTTATCG |

TABLE 4-continued

| Target | Seq ID | DIANA Sequence |
|---|---|---|
| | SeqID-177 | CTGGTGAAGTTGTAATCTGG |
| | SeqID-178 | GTTGAGCAGAGGTTCTTTTT |
| | SeqID-179 | TCGGTTAATTTATTATATTC |
| | SeqID-180 | TACTCATGCCATACATAAAT |
| | SeqID-181 | GACGTCATATGAAGGTGTGC |
| | SeqID-182 | AGTGCTAATAATTCACCTGT |
| | SeqID-183 | GGTGGATAGCAGTACCTGAG |
| | SeqID-184 | ATCATTTTTCATGTTGTTAT |
| | SeqID-185 | CTCTTTTGAACTTTAGCATC |
| | SeqID-186 | TTAGTTGAATATCTTTGCCA |
| | SeqID-187 | TTTCTTTTTCTCTATTAATG |
| | SeqID-188 | GCGATTGTATTGCTATTATC |
| | SeqID-189 | CGATTGTGACACGATAGCCA |
| | SeqID-190 | ATGTTGGAGCTTTTATCGT |
| | SeqID-191 | TTTTCGAGTCCCTTTTTACC |
| | SeqID-192 | CTGCATCATCTTTATAGCCT |
| | SeqID-193 | TTCTTTTTGTTTTAATTCTT |
| | SeqID-194 | TTAATGGGACCAACATAACC |
| | SeqID-195 | GATGTGAAGTCGCTTTTTCT |
| | SeqID-196 | GAAGTCGCTTTTCCTAGAGG |
| | SeqID-197 | ATAGTTACGACTTTCTGTTT |
| | SeqID-198 | GTTGTAAGATGAAATTTTTT |
| | SeqID-199 | AATCACTTAAATATTCATCC |
| | SeqID-200 | AATCTCTTAAATATTCATCC |
| | SeqID-201 | TTTAACGGTTTTAAGTGGAA |
| | SeqID-202 | GTATCATCTTGTACCCAATT |
| | SeqID-203 | CCATTTGTTGTTTGATATAG |
| | SeqID-204 | AGAAATACTTAGTTCTTTAG |
| | SeqID-205 | GCTTTATAATCTTTTTTAGA |
| | SeqID-206 | TCTTTGGAACGATGCCTATC |
| | SeqID-207 | TGCTGTTCCTGTATTGGCCA |
| | SeqID-208 | ACATTGTTTCGGTCTAAAAT |
| | SeqID-209 | CACGTTCTGATTTTAAATTT |
| | SeqID-210 | ATGTATGCTTTGGTCTTTCT |
| | SeqID-211 | CCTGGAATAATGACGCTATG |
| | SeqID-212 | AATCTAACTTCCACATACCA |
| | SeqID-213 | TTTAACAAAATTAAATTGAA |
| | SeqID-214 | CGATCAATGTTACCGTAGTT |
| | SeqID-215 | TAATTTTATATTGAGCATCT |
| | SeqID-216 | TTTTTTATTTTTAGATACTT |
| | SeqID-217 | ATGAAAAAAATTTATATTAG |
| | SeqID-218 | GTGTTCTAGTTCTTTTGCTA |
| | SeqID-219 | TAGTTCTTTTACTAATTATG |
| | SeqID-220 | AATAACTTGGTTATTCAAAG |
| | SeqID-221 | TTATTCAGAGATAACGATAT |
| | SeqID-222 | GATATTGAGAAAACAATTAG |
| | SeqID-223 | GAAAACAATTAATTCTATTG |
| | SeqID-224 | TTGAAAAAGGAAACTATAAC |
| | SeqID-225 | AAACTATAACAAAGTATATA |
| | SeqID-226 | ATATAAAAATAGTTCAGAAA |
| | SeqID-227 | TAGTTCAGAAGCATCTAAAC |
| | SeqID-228 | AAACTGGCATATGGAGAAGA |
| | SeqID-229 | AGAAGAAATTATAGATAGGA |
| | SeqID-230 | TTGTAGATAGGAATAAAAAA |
| | SeqID-231 | CAAAGATTTAAGTGTCAATA |
| | SeqID-232 | AAAATTACTAATCATGAAAT |
| | SeqID-233 | CATAAAATCTAAAAAAATCGG |
| | SeqID-234 | AAACTGGAAAAGATAAAAAG |
| | SeqID-235 | AGTTGATGTTAGATATAACA |
| | SeqID-236 | TGATGTTAAATATAACATAT |
| | SeqID-237 | ATGGAAATATACGCCGTAAT |
| | SeqID-238 | AAATATGGAACTATACGACG |
| | SeqID-239 | TTATGAAGAAAGCATTGGA |
| | SeqID-240 | CACAATTAAACTTTATTTAT |
| | SeqID-241 | TGGACCAGGGTAGTAATAATA |
| | SeqID-242 | TAAGCATTGGAAATTAGATT |
| | SeqID-243 | GGATTGAAAAATAGGCAAAA |
| | SeqID-244 | CCAGACGTAATAGTACCTGG |
| | SeqID-245 | AAAATGGACAGAAAATTAAT |
| | SeqID-246 | TAAAATCAGAACGAGGCAAA |
| | SeqID-247 | AACATTAAAATCAGAGCGAG |
| | SeqID-248 | ATAAAAGATAGAAATGGTAT |
| | SeqID-249 | GTATAGAGTTGGCTAAAACT |
| | SeqID-250 | TAGCTAAAACTGGAAATACA |
| | SeqID-251 | AATCGGTATTGCCCTAACA |
| | SeqID-252 | GAAATACATACGAAATCGGT |
| | SeqID-253 | TAAAACACCCAAAAATAAGT |
| | SeqID-254 | CCCAAAGAAAAATATGATGA |
| | SeqID-255 | GACGATATTGCTCGTGGTTT |
| | SeqID-256 | CTCGTGACTTACAAATTGAT |
| | SeqID-257 | AGCTATAACCAATAAAGTTA |
| | SeqID-258 | AAATGGGTTCAGCCAGATTC |
| | SeqID-259 | AAAATGGGTACAGCCAGATT |
| | SeqID-260 | TACCAATTAAAAAGATAAAT |
| | SeqID-261 | AGATGAATATATAGACAAAT |
| | SeqID-262 | ATAAAAAGACGAATCTATAG |
| | SeqID-263 | AAATCATACAATTTACAAAT |
| | SeqID-264 | CTATAAAAAGCCGTGTTTAT |
| | SeqID-265 | AAATACTGTAAAAAGTCGTG |
| | SeqID-266 | GAACGAAGCAACAGTACACC |
| | SeqID-267 | TATCCATTGAATGAAGCAAC |
| | SeqID-268 | GGTTATGTGGGTCCAATTAA |
| | SeqID-269 | TATGTGGGCCCCATTAATTC |
| | SeqID-270 | ACGAGTTAAAAAGTAAGCAA |
| | SeqID-271 | TAAGCAATTTGGAAACTATA |
| | SeqID-272 | AAACTATAGCAAAAATACTG |
| | SeqID-273 | GGAAAAAAAGGCTTAGAACG |
| | SeqID-274 | AAAAAGGGGATTAGAGCGCC |
| | SeqID-275 | ATGATAAACAATTGCAAAAC |
| | SeqID-276 | TGGTTTTAAGGTATCCATTG |
| | SeqID-277 | TTTAGGGTATCCATTGCTAA |
| | SeqID-278 | ACTTATGCAATAAAACCTTT |
| | SeqID-279 | ACTTACGATAATAAATCTTT |
| | SeqID-280 | CATTATTGGAGAAAAAGGCT |
| | SeqID-281 | AGAAAAAAGCTAAAAACGGA |
| | SeqID-282 | CGGAAAAGATCTTCATTTAA |
| | SeqID-283 | AACAATAGATGCTAGGGTAC |
| | SeqID-284 | GATGCTAGAGTACAAGAAAG |
| | SeqID-285 | GTATTTATAATCATATGAAA |
| | SeqID-286 | ATAAACATATGAAAAATGAC |
| | SeqID-287 | AAAAATGACTTTGGATCTGG |
| | SeqID-289 | ATCTGGTACAGCATTACAAC |
| | SeqID-290 | ACTGGAGAAATTTTAGCTTT |
| | SeqID-291 | CAACCTAAAACTGGGGAAAT |
| | SeqID-292 | GTACCCCATCGTACGATGTT |
| | SeqID-293 | TACCCCTTCATATGATGTTT |
| | SeqID-294 | ATTCATGAATGGATTAAGCA |
| | SeqID-295 | TCATTAATGGAATTAGCAAT |
| | SeqID-296 | AATCATGATTATCATAAATT |
| | SeqID-297 | GACTACCGTAAATTAACTAA |
| | SeqID-298 | AAAAAGAGCCTTTGCTCAAC |
| | SeqID-299 | GAGCCGTTACTCAATAAATT |
| | SeqID-300 | TCAAATCACTACATCACCAG |
| | SeqID-301 | ACCCAAAAAATATTAACATC |
| | SeqID-302 | CTACATCACCGGGTTCAACC |
| | SeqID-303 | ATTAACGTCTATTATTGCCT |
| | SeqID-304 | TAGCCTTAAAAGAAAATAAA |
| | SeqID-305 | TAAACTAGACGACAATACTA |
| | SeqID-306 | CAAAAATACTAATTTTGATA |
| | SeqID-307 | GGTAAGGGTTGGCAAAAAGA |
| | SeqID-308 | TTATGGTAAAGGATGGCAAA |
| | SeqID-309 | CATGGGGGAATTATAATATC |
| | SeqID-310 | GATGTATCTTGGGGAGATTA |
| | SeqID-311 | ATTTAAAGTAGTAGACGGCA |
| | SeqID-312 | TAACAAGATTTAAAGTGGTA |
| | SeqID-313 | GATTTAAAGCAAGCAATAGA |
| | SeqID-314 | GACGGTAAGATAGATTTAAA |
| | SeqID-315 | CAGACAACATATTTTTTGCC |
| | SeqID-316 | TTTTTTGCACGTATTGCATT |
| | SeqID-317 | TGCATTAGCATTAGGAGCCA |
| | SeqID-318 | TAGCTTTAGGAGCTAAAAAA |
| | SeqID-319 | TTTGAGCAAGGTATGCAAGA |
| | SeqID-320 | AAGATTTAGGTGTTGGTGAA |
| | SeqID-321 | GAATCGGTGAAAATATCCCG |
| | SeqID-322 | TCCCGAGCGATTACCCCTTT |
| | SeqID-323 | TTATCCCTTTTATAAAGCAC |
| | SeqID-324 | GCACAAATTTCAAATAGTAA |
| | SeqID-325 | TCAAATAGTAATTTAAAAAA |
| | SeqID-326 | TATTATTAGCAGATTCAGGA |
| | SeqID-327 | AAATAATGACATATTACTAG |
| | SeqID-328 | CCAAGGCGAGATACTAGTAA |
| | SeqID-329 | TACTAGTAAATCCTATACAA |
| | SeqID-330 | ATACAAATTTTATCAATATA |
| | SeqID-331 | AATTTTGTCAATCTACAGTG |
| | SeqID-332 | CTTTAGAAAATAACGGAAAT |
| | SeqID-333 | AAATAACGGGAATATACAAA |

TABLE 4-continued

| Target | Seq ID | DIANA Sequence |
|---|---|---|
| | SeqID-334 | AAATCCTCATGTTTTACGTA |
| | SeqID-335 | TTACGTGAAACAAAGTCTCA |
| | SeqID-336 | AAATCTCAAATATGGAAAAA |
| | SeqID-337 | TTGGAAAAAGTCTATTATAT |
| | SeqID-338 | TTATACCTAAAAAAGACATA |
| | SeqID-339 | ATTAACTAATGGTATGGAAC |
| | SeqID-340 | ACGTGTAGTGACTAAAACAC |
| | SeqID-341 | GTTAATAAAACACATAGGGA |
| | SeqID-342 | TAGAGATGATATCTACAAAA |
| | SeqID-343 | TATACAAAAATTATGCCCGA |
| | SeqID-344 | CCCGAATTATAGGTAAATCT |
| | SeqID-345 | TGGTAAATCTGGCACAGCAG |
| | SeqID-346 | AAAATGAATCAAGGGGAAAC |
| | SeqID-347 | TGAAACAAGGTGAAACCGGA |
| | SeqID-348 | GACAAATAGGTTGGTTTGTT |
| | SeqID-349 | TAATAAAAATAATCCTAATA |
| | SeqID-350 | ATGATAAACATAACCCCAAT |
| | SeqID-351 | ATGGCGATTAATGTTAAAGA |
| | SeqID-352 | TATGCTAATGGCAATTAATG |
| | SeqID-353 | AAAATAAAGGGATGGCCAGC |
| | SeqID-354 | GGCTAGCTATAATGCTGCTA |
| | SeqID-355 | TGCTACTATATCTGGAAAAG |
| | SeqID-356 | GATGATTTGTATGATAATGG |
| | SeqID-357 | ATGATTTATATGATTATGGA |
| | SeqID-358 | CTCAATTTGATATAGATCAG |
| | SeqID-359 | CTAAATTTGACATAGATGAG |
| | SeqID-360 | GAAGCAATAGAATCATCAGA |
| | SeqID-361 | AATGAAATATTATTAGCAGA |
| | SeqID-362 | ATCACCAGGTTCAACCCAAA |
| | SeqID-363 | ATTTTACGATCCTGAATGTT |
| | SeqID-364 | CTTTAACGCCTAAACTATTA |
| | SeqID-365 | TTTTATCGGACGTTCAGTCA |
| | SeqID-366 | ACTTCACCATTATCGCTTTT |
| | SeqID-367 | TATAACTGCTATCTTTATAA |
| | SeqID-368 | TTTGAAATTTTTATCTTCAA |
| | SeqID-369 | TCAATAGTATTATTAATTTC |
| | SeqID-370 | CTTTTGAAGCATAAAAATAT |
| | SeqID-371 | AAACCCGACAACTACAACTA |
| | SeqID-372 | ATAAGTGGAACAATTTTTAT |
| Gene(s) conferring resistance to vancomycin | SeqID-373 | ATGAATAGAATAAAAGTTGC |
| | SeqID-374 | TGTTTGGGGGTTGCTCAGAG |
| | SeqID-375 | TGACGTATCGGTAAAATCTG |
| | SeqID-376 | GAGATAGCCGCTAACATTAA |
| | SeqID-377 | AAAAATACGAGCCGTTATAC |
| | SeqID-378 | AATTACGAAATCTGGTGTAT |
| | SeqID-379 | ATGTGCGAAAAACCTTGCGC |
| | SeqID-380 | GGGAAAACGACAATTGCTAT |
| | SeqID-381 | TGTACTCTCGCCGGATAAAA |
| | SeqID-382 | CACGGATTACTTGTTAAAAA |
| | SeqID-383 | ATGAATATGAAATCAACCAT |
| | SeqID-384 | TGTAGCATTTTCAGCTTTGC |
| | SeqID-385 | AAGTCAGGTGAAGATGGATC |
| | SeqID-386 | AAGGTCTGTTTGAATTGTCC |
| | SeqID-387 | CCCTTTTGTAGGCTGCGATA |
| | SeqID-388 | AGCTCAGCAATTTGTATGGA |
| | SeqID-389 | CGTTGACATACATCGTTGCG |
| | SeqID-390 | TGCTGGGATAGCTACTCCCG |
| | SeqID-391 | TGGGTTATTAATAAAGATGA |
| | SeqID-392 | TGTTTTTGTTAAGCCGGCGC |
| | SeqID-393 | GGCTCATCCTTCGGTGTGAA |
| | SeqID-394 | TCAATAGCGCGGACGAATTG |
| | SeqID-395 | CGCAATTGAATCGGCAAGAC |
| | SeqID-396 | GACAGCAAAATCTTAATTGA |
| | SeqID-397 | CTGTTTCGGGCTGTGAGGTC |
| | SeqID-398 | TGCGGTATTGGGAAACAGTG |
| | SeqID-399 | TTAGCTGTTGGCGAGGTGGA |
| | SeqID-400 | TCAGGCTGCAGTACGGAATC |
| | SeqID-401 | TATTCATCAGGAAGTCGAGC |
| | SeqID-402 | AAAGGCTCTGAAAACGCAGT |
| | SeqID-403 | CCGTTCCCGCAGACCTTTCA |
| | SeqID-404 | GGAGCGAGGACGGATACAGG |
| | SeqID-405 | GCAAAAAAATATATAAAGC |
| | SeqID-406 | GCTGTAGAGGTCTAGCCCGT |
| | SeqID-407 | TATGTTTTTACAAGATAACG |
| | SeqID-408 | ATTGTACTGAACGAAGTCAA |
| | SeqID-409 | TGCCCGGTTTCACGTCATAC |
| | SeqID-410 | TTATCCCCGTATGATGGCCA |
| | SeqID-411 | GGTATTGCACTTCCCGAACT |
| | SeqID-412 | ACCGCTTGATCGTATTAGCG |
| | SeqID-413 | GGCTGTGATATTCAAAGCTC |
| | SeqID-414 | GGCTGCGATATTCAAAGCTC |
| | SeqID-415 | AAAAATCTTAATTGAGCAAG |
| | SeqID-416 | TGATTACATTGGCGTTAAAG |
| | SeqID-417 | TGATTACATTGGCGATAAAG |
| | SeqID-418 | ATTTCGGTCTGTGAGGTCGG |
| | SeqID-419 | CGAGCCGGAAAAAGGCTCTG |
| | SeqID-420 | ATGAATAGAATAAAAGTCGC |
| | SeqID-421 | ATGAATAAAATAAAAGTCGC |
| | SeqID-422 | GTCGCAATCATCTTCGGCGG |
| | SeqID-423 | GTCGCAATTATCTTCGGCGG |
| | SeqID-424 | GTCGCAACTATCTTCGGCGG |
| | SeqID-425 | TCTTCGGCGGTTGCTCGGAG |
| | SeqID-426 | TGATGTGTCGGTAAAATCCG |
| | SeqID-427 | GAAATTGCTGCGAACATTGA |
| | SeqID-428 | GAACATTGATACGGAAAAAT |
| | SeqID-429 | GAACATTAATACTGAAAAAT |
| | SeqID-430 | AAAAATTCGATCCGCACTAC |
| | SeqID-431 | AATTACAAAAAACGGTGTAT |
| | SeqID-432 | AATTACAAAAAACGGCGTAT |
| | SeqID-433 | CTATGCAAGAAGCCATGTAT |
| | SeqID-434 | GGGAAGCCGACAGTCTCCCC |
| | SeqID-435 | GGGAAGCCGATAGTCTCCCC |
| | SeqID-436 | ATACTCTCCCCGGATAGGAA |
| | SeqID-437 | ATATTCTCCCCGGATAGGAA |
| | SeqID-438 | GCATGGGCTGCTTGTCATGA |
| | SeqID-439 | GCATGGTCTGCTTGTCATGA |
| | SeqID-440 | AAAGCGAATACGAAACACGG |
| | SeqID-441 | AAAGAGAATACGAAACTCGG |
| | SeqID-442 | GCGTATTGATGTGGCTTTCC |
| | SeqID-443 | GCGTATTGACGTGGCTTTCC |
| | SeqID-444 | GGCTTTCCCGGTTTTGCATG |
| | SeqID-445 | AAATGCGGGGAGGATGGTGC |
| | SeqID-446 | AGGGGCTGTTTGTATTGTCT |
| | SeqID-447 | AGGGTCTGTTTGAATTGTCT |
| | SeqID-448 | CTATGTGGGCTGTGATATTC |
| | SeqID-449 | CTATGTAGGCTGCGATATTC |
| | SeqID-450 | TCCGCAGCTTGCATGGACAA |
| | SeqID-451 | TGGCCTACATTCTTACAAAA |
| | SeqID-452 | GGGCATCGCCGTTCCCGAAT |
| | SeqID-453 | GGGCATCGCCGTCCCCGAAT |
| | SeqID-454 | TTCAAATGATTGATAAAGGT |
| | SeqID-455 | TTCAAATTATTGATAAAGGT |
| | SeqID-456 | TTCAAATGATTGAAAAAGGT |
| | SeqID-457 | CAAGCCGGAGGCGGGTGCGC |
| | SeqID-458 | CAAACCGGAGGCGAGGACGC |
| | SeqID-459 | AGGCGGGTGCGCTTACCTAC |
| | SeqID-460 | CTTTGTGAAGCCGGCACGGT |
| | SeqID-461 | TCGTCCTTTGGCGTAACCAA |
| | SeqID-462 | GATAGAAGCGGCAGGACAAT |
| | SeqID-463 | GATAGAAGCAGCAGGACAAT |
| | SeqID-464 | GAAAAATCTTAATTGAGCAA |
| | SeqID-465 | CTGTGAGGTCGGGTGTGCGG |
| | SeqID-466 | CTGTGAGGTCGGCTGCGCGG |
| | SeqID-467 | GGTCATGGGAAACGAGGATG |
| | SeqID-468 | GGTCATGGGGAACGAGGATG |
| | SeqID-469 | ATTGTCGGCGAAGTGGATCA |
| | SeqID-470 | CCGGCTGAGCCACGGTATCT |
| | SeqID-471 | CCGGTTGAGCCACGGTATCT |
| | SeqID-472 | CCATCAGGAAAACGAGCCGG |
| | SeqID-473 | GGCTCAGAAAATGCGATGAT |
| | SeqID-474 | GGCTCAGAGAATGCGATGAT |
| | SeqID-475 | ATTACAGTTCCCGCAGACAT |
| | SeqID-476 | ATTATCGTTCCAGCAGACAT |
| | SeqID-477 | ATCACGCTTCCTGCACTGAT |
| | SeqID-478 | ATCACGCTTCCCGCACTAAT |
| | SeqID-479 | ACATTCCGGTCGAGGAACGA |
| | SeqID-480 | ATCGGGTGCAAGAGACGGCA |
| | SeqID-481 | ATCGGGTGCAAGAAACGGCA |
| | SeqID-482 | ATCGGGTGCAGGAAACGGCA |
| | SeqID-483 | AAGAAGTATATCGGGTGCT |
| | SeqID-484 | GCAGAGGGCTTGCCCGTGTT |
| | SeqID-485 | GCAGAGGGCTTGCTCGTGTT |
| | SeqID-486 | TTTTTTGCAGGAGGATGGCG |
| | SeqID-487 | GTTCTAAATGAGGTCAATAC |
| | SeqID-488 | GTTCTAAACGAGGTCAATAC |

TABLE 4-continued

| Target | Seq ID | DIANA Sequence |
|---|---|---|
| | SeqID-489 | CAATACCATGCCCGGTTTTA |
| | SeqID-490 | CAATACCATGCCAGGTTTTA |
| | SeqID-491 | TACCCACGTATGGTGGCCGC |
| | SeqID-492 | TATCCACGCATGGCGGCTGC |
| | SeqID-493 | TACCCACGTATGATGGCCGC |

Table 5 Shows DIANA Sequences for Identifying Fungi

TABLE 5

| Target | Seq ID | DIANA Sequence |
|---|---|---|
| Candida parapsilosis | SeqID-494 | GGTATCAGTATTCAGTAGTC |
| | SeqID-495 | AGTATTCAGTAGTCAGAGGT |
| | SeqID-496 | CAGTAGTCAGAGGTGAAATT |
| | SeqID-497 | CAGAATGAAAAGTGCTTAAC |
| | SeqID-498 | TGCATTTTTTCTTACACATG |
| | SeqID-499 | GGTAGGCCTTCTATATGGGG |
| | SeqID-500 | TAATGTCAACCGATTATTTA |
| Candida tropicalis | SeqID-501 | GGCCGGTCCATCTTTCTGAT |
| | SeqID-502 | TCCATCTTTCTGATGCGTAC |
| | SeqID-503 | TTTCTGATGCGTACTGGACC |
| | SeqID-504 | CTGATTTGCTTAATTGCACC |
| | SeqID-505 | ACATGTGTTTTTTATTGAAC |
| | SeqID-506 | AAATTTCTTTGGTGGCGGGA |
| | SeqID-507 | GCAATCCTACCGCCAGAGGT |
| | SeqID-508 | TATAACTAAACCAAACTTTT |
| | SeqID-509 | TATTTACAGTCAAACTTGAT |
| | SeqID-510 | TTATTATTACAATAGTCAAA |
| Candida auris | SeqID-511 | GGGTTTTGGAGGGAGGTCCA |
| | SeqID-512 | GGGAGGTCCACCTCACGGTG |
| | SeqID-513 | CCTCACGGTGAGTACTTCCA |
| | SeqID-514 | GTACTTCCATATCCAAGACC |
| | SeqID-515 | TATCCAAGACCTTTCCTCTG |
| | SeqID-516 | CTTTCCTCTGCTTCCTCGCA |
| | SeqID-517 | TGATATTTTGCATACACACT |
| | SeqID-518 | TGATTTGGATTTTAAAACTA |
| | SeqID-519 | AACCCAACGTTAAGTTCAAC |
| | SeqID-520 | CTAAAACAAAAACATAAAAC |
| Candida lusitaniae | SeqID-521 | TCCTCCTCCTCTTAGCAATA |
| | SeqID-522 | CTTAGCAATAAGAGGAGGAC |
| | SeqID-523 | AGAGGAGGACTGTTACTTTG |
| | SeqID-524 | AAAAATACATTACACATTGT |
| | SeqID-525 | TGTTTTTGCGAACAAAAAAA |
| | SeqID-526 | AAATAAATTTTTTTATTCGA |
| | SeqID-527 | TTCGAATTTCTTAATATCAA |
| Candida kefyr | SeqID-528 | CTTTGGGTCTGGTTGGCCGG |
| | SeqID-529 | CCGGTCCGATTTTATGTCGC |
| | SeqID-530 | TCGCGCACTGGTTTTCAACC |
| | SeqID-531 | AACCGGATCTTTCCTTCTGG |
| | SeqID-532 | CTGGCTAACCTGTACTCCTT |
| | SeqID-533 | CCTTGTGGGTGCAGGCGAAC |
| | SeqID-534 | AGCAGGCGAAAGCTCGAATA |
| | SeqID-535 | GATCGTCTGAACAAGGCCTG |
| | SeqID-536 | GCCAGTTCTTGATTCTCTGC |
| | SeqID-537 | AGTTTTCTATTTCTCATCCT |
| | SeqID-538 | AACAATATTTTGTATTATGA |
| | SeqID-539 | CTATTATACTATAAAATTTA |
| Candida guilliermondii | SeqID-540 | TGGCTAACCATTCGCCCTTG |
| | SeqID-541 | GAAATTCTTAGATTTACTGA |
| | SeqID-542 | TTAATTATTTTTACAGTTAG |
| | SeqID-543 | ATTTTTACAGTTAGTCAAAT |
| | SeqID-544 | ACAGTTAGTCAAATTTTGAA |
| Candida rugosa | SeqID-545 | TTCGACGCATCTGAGGGGTC |
| | SeqID-546 | GGTGCGTACTCTGAGGGTGC |
| | SeqID-547 | GCGCCTTGCGGCAAGCCAGA |
| | SeqID-548 | AACAACAATACAACTTTGTG |
| | SeqID-549 | TGTGTCTGAACAATAACTTC |
| | SeqID-550 | CTTCAAGTACCGATCATCAA |
| | SeqID-551 | CATCAAATTGTTAAAACAAA |

TABLE 5-continued

| Target | Seq ID | DIANA Sequence |
|---|---|---|
| Candida famata | SeqID-552 | AGTATTCTTTTTGCCAGCGC |
| | SeqID-553 | TTAATTGCGCGGCGAAAAAA |
| | SeqID-554 | CCTTACACACAGTGTTTTTT |
| | SeqID-555 | GTTATTACAAGAACTTTTGC |
| | SeqID-556 | TTTGGTCTGGACTAGAAATA |
| | SeqID-557 | GTTTGGGCCAGAGGTTTACT |
| | SeqID-558 | GAACTAAACTTCAATATTTA |
| | SeqID-559 | TATTGAATTGTTACTTATTT |
| | SeqID-560 | AATTGTCAATTTGTTGATTA |
| | SeqID-561 | AATTCAAAAAATCTTCAAAA |
| Candida norvegensis | SeqID-562 | CTGTGATTTAAACTTCTTTC |
| | SeqID-563 | TTACACCGCGTGAGCGCACA |
| | SeqID-564 | ACAACACCTAAACACGAATA |
| | SeqID-565 | ACCATGTCACCCAGAGAAAA |
| | SeqID-566 | AAATCTCAAACGAGAAGAAA |
| Candida inconspicua | SeqID-567 | TGTGATTTTAACATCTTTAC |
| | SeqID-568 | ACACTGCGTGAGCGCACAAC |
| | SeqID-569 | ACAACACCTAAACATGAATA |
| | SeqID-570 | TACTTACTAGTCACTAAGAA |
| | SeqID-571 | GAAAAATCTAAAAGAAATAA |

In some embodiments, the preferred DIANA oligomer is between 7-20 bases in length (i.e. 7-20 mer). In other embodiments, the preferred DIANA oligomer is between 12-18 bases in length (i.e. 12-18 mer).

In some embodiments, the DIANAs provided herein comprise a sequence that is the complement, reverse, or reverse complement of a sequence described in Tables 1-5. In some embodiments, the DIANAs provided herein comprise a sequence that shares at least about 60-70% identity with a sequence described in Tables 1-5, or the complement, reverse, or reverse complement of a sequence described in Tables 1-5. In another embodiment, the DIANA has a sequence that shares at least about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identity with the sequences of Tables 1-5, or the complement, reverse, or reverse complement of a sequence described in Tables 1-5. The terms "identity" or "homology" or "similarity" refer to sequence relationships between two DIANA sequences and can be determined by comparing a nucleotide position in each sequence when aligned for purposes of comparison. The term "identity" refers to the degree to which nucleic acids are the same between two sequences. The term "homology" or "similarity" refers to the relatedness of two functionally-equivalent DIANA sequences.

The DIANA sequences also include functional fragments of the sequence provided in Tables 1-5 and sequences sharing certain sequence identities with those in Tables 1-5, as described above, provided they function to specifically anneal to and identify microorganisms. In one aspect, these fragment sequences have 1, 2, 3, 4, 5, or 6 less bases at either or both ends of the original sequences in Tables 1-5. These shorter sequences are also within the scope of the present disclosure.

In addition, the DIANA sequences, including those provided in Tables 1-5 and sequences sharing certain sequence identities with those in Tables 1-5, as described above, can be incorporated into longer sequences, provided they function to specifically anneal to and identify microorganisms. In one aspect, the longer sequences have 1, 2, 3, 4, 5, 6, 7, 8, 9, or 10 additional bases at either or both ends of the original sequences. These longer sequences are also within the scope of the present disclosure.

In some embodiments, the DIANA oligomer may include one or more artificial nucleobases such as, but not limited to pseudo-cytosines, guanidinium G-clamps, diaminopurines, inosines, etc. It is to be understood, that those skilled in the art may utilize artificial or unnatural bases for a number of reasons. Notwithstanding the above, it is the base-pairing rules which dictate if binding (invasion) will occur or not. It is thus to be understood that, in a non-limiting example, the use of a pseudo-cytosines in a DIANA oligomer in place of a cytosine is defined as a homologous sequence.

In some embodiments, ssDNA are targeted rather than dsDNA. In some embodiments, ssDNA are created from dsDNA via denaturing protocols or through an asymmetric amplification process prior to DIANA tagging of the DNA molecule.

In some embodiments the DNA is entirely in duplex form. In some embodiments, the DNA is locally in duplex form.

In some embodiments, the DIANA oligomer is modified to contain a one or more binding moieties. In some embodiments, the binding moiety binds the DIANA to a solid substrate. In some embodiments, the binding DIANA to a solid substrate is useful for separation or washing steps downstream. By way of example, but not by way of limitation, in some embodiments, the binding moieties include, but are not limited to, non-covalent binding moieties (e.g., such as biotin, digoxin, digitoxin) or covalent binding moieties (e.g., COOH group, NHS-ester group, malemide chemistry, and Click chemistry).

In some embodiments, the binding moiety is spaced from the DIANA probe by one or more linkers. In some embodiments, the linker is a single molecule. In some embodiments the linker is comprised of a chain of multiple individual molecules, either linear or branched, that are combined to create a single linker molecule.

In some embodiments, the linker length is between about 20 to 200, about 40 to 180, about 60 to 160, about 80 to 140, or about 100 to 120 atoms. In some embodiments, the linker length is at least 40 atoms. The disclosed linker lengths are not commonly used in the art.

In some embodiments, one or more binding moieties are used along a single linker. In some embodiments, two or more binding moieties along a single linker, wherein each linker has one or more binding moieties and wherein each binding moiety is attached to a different location along the oligomer. In some embodiments, multiple binding moieties increase the surface binding kinetics and/or yield and/or efficiently, and/or strength.

In some embodiments, the DNA amplicon is first tagged with one or more DIANAs and then the hybrid complex is captured onto the solid-phase surface.

In some embodiments, the DIANA is incubated with a solid surface prior to capturing the microbial genetic material DNA.

In some embodiments, the solid-phase surface is a bead, nanoparticle, microparticle or flat substrate. In some embodiments, the solid-phase surface is further chemically modified to facilitate binding of the DIANA to it. In some embodiments, capturing a target amplicon and immobilizing it onto the solid-phase surface occurs in individuals wells or chambers on system (e.g., a plate or a chip).

In some embodiments, a well is activated with more than one DIANA probe for a single pathogen; for example, the detection region for *Staphylococcus aureus*. In some embodiments, one or more probes in a single well may be used for multiple pathogens; for example, a single well for *Staphylococcus aureus, Enterococcus faecalis*, and *Candida albicans*.

As used herein, "atom" refers to a carbon atom, a nitrogen atom, an oxygen atom, or any atom capable of making two or more covalent bonds. Alternatively, in some embodiments, "atom" refers to the distance between two covalently bound atoms. By way of example, but not by way of limitation, the following structure: DIANA-$(CH_2)_{40}$-(binding moiety) has a linker (—$(CH_2)_{40}$—) with a length of 40 atoms. By way of example, but not by way of limitation, the following structure: DIANA-$(CH_2)_{40}$—O—$(CH_2)_{40}$-(binding moiety) has a linker (—$(CH_2)_{40}$—O—$(CH_2)_{40}$—) with a length of 81 atoms. By way of example, but not by way of limitation, the following structure: DIANA-$(CH_2)_{40}$—O—NH—$(CH_2)_{30}$-(binding moiety) has a linker (—$(CH_2)_{40}$—O—NH—$(CH_2)_{30}$—) with a length of 72 atoms. By way of example, but not by way of limitation, the following structure: DIANA-$(CH_2)_{40}$—O—N$(CH_2)_3CH_3$—$(CH_2)_{30}$-(binding moiety) has a linker (—$(CH_2)_{40}$—O—N$(CH_2)_3CH_3$—$(CH_2)_{30}$—) with a length of 72 atoms (the —$(CH_2)_3CH_3$ component branches off of the nitrogen atom and does not contribute to the length of the linker).

Microbial Genetic Material

The methods, assays, and kits disclosed herein are directed to detecting binding of DIANAs to microbial genetic material. As is used herein, "microbial genetic material" comprises polynucleotides of microorganisms. Polynucleotides includes any compound and/or substance that comprises a polymer of nucleotides (nucleotide monomer). Polynucleotides include, for example, deoxyribonucleic acid (DNA) and ribonucleic acid (RNA). Exemplary polynucleotides of a microorganism include, e.g., genomic DNA, plasmid DNA, mRNA, tRNA, rRNA, and sRNA.

In some embodiments, microbial genetic material is from a bacterial cell. In some embodiments, the microbial genetic material is from a Gram positive bacterial cell. In some embodiments, the microbial genetic material is from a Gram negative bacterial cell. In some embodiments, the microbial genetic material is from a fungal cell.

Samples and Sample Collection

In some embodiments, the sample is about 1 µl, 10 µl, 20 µl, 30 µl, 40 µl, 50 µl, 60 µl, 70 µl, 80 µl, 90 µl, 100 µl, or any amount between any two of the previously listed amounts. In some embodiments, the sample is between about 100 µl to 2.5 ml, about 200 µl to 2 ml, about 300 µl to 1.5 ml, about 400 µl to 1 ml, or about 500 µl to 750 µl. In some embodiments, the sample is between about 0.5 ml to 10 ml, about 1 ml to 9 ml, about 2 ml to 8 ml, about 3 ml to 7 ml, or about 4 ml to 6 ml. In some embodiments, the sample is between about 1.0 ml to 3 ml. In some embodiments, the sample is between about 0.1 ml to 1.0 ml. In some embodiments, larger sample volumes provide greater sensitivity to microorganisms present at low concentrations.

In some embodiments, smaller sample volumes can be used, for example, when testing for neonatal septicemia. In some embodiments, the sample is about 0.5 ml to about 1.5 ml. In some embodiments, sample is about 0.1 ml to about 1.0 ml. In some embodiments, the sample is about 0.1 ml, about 0.2 ml, about 0.3 ml, about 0.4 ml, about 0.5 ml, about 0.6 ml, about 0.7 ml, about 0.8 ml, about 0.9 ml, about 1.0 ml, about 1.1 ml, about 1.2 ml, about 1.3 ml, about 1.4 ml, about 1.5 ml, about 1.6 ml, about 1.7 ml, about 1.8 ml, about 1.9 ml, or about 2.0 ml.

In some embodiments, the sample is from a subject. Subjects include, but are not limited to, mammals, avians, reptiles, insects, amphibians, and fish. In some embodiments, a mammalian subject is human. In some embodiments, the subject is an adult human. In some embodiments, the subject is a child human (i.e., 2-16 years of age). In some embodiments, the subject is an infant (i.e., under 2 years of age).

In some embodiments, the subject has or is suspected of having an infection, e.g., a microbial infection. Examples of microbial infections include, for example, sepsis, e.g., infective endocarditis, and neonatal septicemia. Other examples of microbial infections include, but are not limited to pneumonia, urinary track infections, joint infections, spinal fluid infections, etc.

In some embodiments, the microbial cells in the sample or suspected of being in the sample, include, but are not limited to bacterial cells, fungal cells, viral particles, or a combination thereof.

In some embodiments, the sample comprises a bodily fluid, bodily excretion, or bodily secretion, e.g., blood, urine, saliva, stool, or sputum. In some embodiments, samples are comprised of human blood. In some embodiments, it is advantageous to utilize whole-blood or unprocessed blood as this removes the need to separate the blood into its various components, a rather laborious process.

In some embodiments, the methods described herein comprise acquiring a sample from a subject.

For assays in blood, microbial loads can be low and the potential for contaminations is a serious concern. Contaminations may come in the form of free nucleic acids or microbes (microorganisms). Contaminating microbes may come from many sources, including the patient's skin, healthcare provider, hospital equipment, etc. Provided herein are improved methods for collecting blood samples. Without wishing to be bound by theory, collecting more than one blood sample in the same draw, for example, by collecting multiple vials of blood in sequence, from the same blood-draw, or intravenous line, can allow for reduced levels of contamination in the second and additional samples because the contaminants will be contained in the first sample. This reduction in the level of contaminants likewise results in improved performance in the assays described herein. In some embodiments, acquiring a sample from a subject comprises drawing one or more vials of blood from a subject, preferably from the same blood-draw, or intravenous line. In some embodiments, the blood is drawn from a single line in the subject, e.g., a peripheral blood line or from an IV line.

In some embodiments, more than one vial of blood are drawn from the patient from the same line. Without wishing to be bound by theory, the use of two or more sample tubes for collecting the patient blood is advantageous for, among other things, reducing false-positives, increasing sensitivity, and increasing accuracy. In some embodiments, the first vial of blood is not used in the assay described herein. In some embodiments, the first vial of blood is discarded or used for alternate purposes.

In some embodiments, the vial to be used in the methods described herein contains an anticoagulant such as, for example, EDTA, which is the preferred anticoagulant to be used in the test disclosed here. In some embodiments, a volume between about 0.05-5 ml of blood is collected into the first blood vial (that which is not tested). In some embodiments, the blood volume to be tested is between about 1-10 ml. In other embodiments the blood volume to be tested is between about 1.5 ml and 25 ml.

Integrated Methods for Identifying and Evaluating Microbial Species Using DIANAs In some embodiments, the present technology provides a method for monitoring and/or identifying and/or characterizing microbial cells in a subject. In some embodiments, the method includes one or more of the following steps: (i) depleting eukaryotic DNA from the sample, (ii) lysing one or more microbial cells in the sample, wherein the lysing of one or more microbial cells releases a plurality of microbial genetic materials, (iii) isolating the plurality of microbial genetic materials, (iv) amplifying the plurality of microbial genetic materials, (v) contacting or incubating the amplified microbial genetic materials with a plurality of duplex DNA Invading Artificial Nucleic Acids (DIANAs), and (vi) detecting binding of one or more DIANAs to their target microbial genetic material.

In some embodiments, all of steps (i)-(vi) are performed. In some embodiments, some of steps (ii)-(v) are performed. By way of example, but not by way of limitation, in some sample matrices, it might be possible to skip step (i) because of the relatively low concentration of eukaryotic cells. For example, certain samples, e.g., urine, commonly do not require step (i) because of the low concentration of eukaryotic cells. In another non-limiting example, it might be possible to skip step (i) if the concentration of microbial cells is high enough to allow the user to utilize a smaller sample volume such that the human DNA in the eukaryotic cells is not of sufficient quantity to hinder/inhibit/reduce sensitivity/etc of downstream processes such as, but not limited to, enzymatic amplification.

Depleting Eukaryotic DNA in a Sample

In some embodiments, the methods described herein comprise depleting eukaryotic DNA in a sample.

In some embodiments, for example, but not limited to, when the patient sample does not undergo preprocessing steps such as centrifugation, the first step in the procedure is to selectively remove the human DNA from the specimen through a selective lysis process employing osmotic stress, a combination of non-ionic detergents, and ion exchange resins as described in WO 2016/044621A1, the entirety of which is incorporated herein.

In some embodiments, depleting eukaryotic DNA from the sample includes adding a eukaryotic cell lysis solution to the sample, wherein the eukaryotic cell lysis solution predominantly lyses eukaryotic cells as opposed to microbial cells and removing the eukaryotic DNA released by the lysis of the eukaryotic cells from the sample, wherein one or more intact microbial cells remain in the sample. In some embodiments, the method includes terminating the eukaryotic cell lysis reaction.

Lysis of Eukaryotic Cells

In some embodiments, the eukaryotic cell lysis agent is a solution (hereinafter "a eukaryotic cell lysis solution"). Alternatively, in some embodiments, the eukaryotic cell lysis agent is pelleted and re-suspended in water or an aqueous buffer prior to use.

In some embodiments, the eukaryotic cell lysis solution includes one or more detergents or surfactants. In some embodiments, the detergents or surfactants are non-ionic, anionic, cationic, zwitterionic, or non-detergent sulfobetaines. Detergents and surfactants, include, but are not limited to BigCHAP, Deoxy BigCHAP, Brij 35, Brij 58P, Cymal-1, Cymal-2, Cymal-5, Cymal-6, Decyl-β-maltopyranoside, n-Dodecyl--D-maltoside, n-Hexadecyl- β-D-maltoside, Undecyl-β-D-maltoside, Decyl-β-D-1-thiomaltopyranoside, Octyl-β-D-glucopyranoside, Decyl-β-D-1-thioglucopyranoside, Octyl-β-Dthioglucopyranoside, Digitonin, Dimethyldecylphosphine oxide (APO-10), Dodecyldimethylphosphine oxide (APO-12), IGEPAL CO-520, IGEPAL CO-630, and IGEPAL CO-720, N-Octanoyl-N-methylglucamine(MEGA-8), N-nonanoyl-N-methylglucamine(MEGA-9), N-Decanoyl-N-methylglucamine(MEGA-10), nonidet P40-substitute, Pluronic F-68, saponin, thesit, Triton X-100, Triton X-1 14, TWEEN 20, TWEEN 40, TWEEN 80, sodium cholate, Sodium deoxycholate, sodium glycocholate, sodium taurocholate, sodium taurodeoxycholate, N-1-lauroylsarcosine, lithium dodecyl sulfate, sodium dodecyl sulfate (SDS), hexadecyltrimethyl ammonium bromide (CTAB), trimethyl(tetradecyl) ammonium bromide (TTAB), ASB-14(amidosulfobetaine-14), ASB-16(amidosulfobetaine-16), C7BzO, CHAPS, CHAPSO, EMPIGEN BB, 3-(N,N-Dimethyloctylammonio) propanesulfonate inner salt (SB3-8), 3-(decyldimethylammonio)-propanesulfonate inner salt (SB3-10), 3-(dodecyldimethylammonio)-propanesulfonate inner salt (SB3-12), 3-(N,N-dimethylmyristylammonio)-propanesulfonate(SB3-14), 3-(N,N-dimethylpalmitylammonio)-propanesulfonate (SB3-16), 3-(N,N-dimethyloctadecylammonio)-propanesulfonate(SB3-18), 3-(1-pyridinio)-1-propanesulfonate (NDSB 201), and 3-(benzyldimethylammonio) propanesulfonate (NDSB 256).

By way of example, but not by way of limitation, in some embodiments, the eukaryotic cell lysis solution has a concentration of surfactants between about 0.27% to 15% v/v, between about 0.39% to 13% v/v, between about 0.45% to 12% (v/v), or between about 0.60% to 10% (v/v) of a Tween surfactant and/or between about 0.22% to 10% (v/v), between about 0.16% to 8.25% (v/v), or between about 0.44% to 6.75% (v/v) of Triton or IGEPAL. In some embodiments, the Tween surfactant is selected from the group consisting of Tween-20, Tween-40, and Tween-80. In some embodiments, the Triton is Triton X-100 or Triton X-1 14. In some embodiments, the IGEPAL is selected from the group consisting of IGEPAL CO-520, IGEPAL CO-630, and IGEPAL CO-720.

In some embodiments, the surfactants are stored individually in dry form and re-suspended prior to use.

By way of example, but not by way of limitation, in some embodiments, the eukaryotic cell lysis reaction (e.g., eukaryotic cell lysis solution combined with the sample (herein after the "mixture")) comprise a final concentration of surfactants between about 0.25% to 1% (v/v), between about 0.35% to 0.85% (v/v), between about 0.45% to 0.75% (v/v), or between about 0.55% to 0.65% (v/v) of a Tween surfactant and/or between about 0.15% to 0.65% (v/v), between about 0.25% to 0.55% (v/v), or between about 0.35% to 0.45% (v/v) of Triton or IGEPAL. In some embodiments, the Tween surfactant is selected from the group consisting of Tween-20, Tween-40, and Tween-80. In some embodiments, the Triton is Triton X-100 or Triton X-1 14. In some embodiments, the IGEPAL is selected from the group consisting of IGEPAL CO-520, IGEPAL CO-630, and IGEPAL CO-720.

In some embodiments, the detergent or detergents reduce the structural integrity of the eukaryotic cell.

In some embodiments, at least one anti-foaming agent is combined with the eukaryotic cell lysis solution. Antifoaming agents include, but are not limited to, Antifoam A, Antifoam 204, Antifoam B, Antifoam C, Antifoam Y-30, Antifoam SE-15, and simethicone-based antifoams.

In some embodiments, the mixture contains less than about 0.15 M of monovalent salts. Without wishing to be bound by theory, in some embodiments, when the mixture contains less than about 0.15 M of monovalent salts there is an induction of osmotic stress. In some embodiments, the mixture includes between about 0.15 M to 0.75 M, about 0.2 M to 0.7 M, about 0.25 M to 0.65 M, about 0.3 M to 0.6 M, about 0.35 M to 0.55 M, or about 0.4 M to 0.5 M or monovalent salts.

In some embodiments, the volume ratio of the eukaryotic cell lysis solution to the sample is about 0.25:1, 0.5:1, 0.75:1, 1:1, 2:1, 3:1, 4:1, 5:1, 6:1, 7:1, 8:1, 9:1, 10:1, or any ratio between any two of these ratios.

In some embodiments, the eukaryotic cell lysis reaction is carried out at about room temperature. In some embodiments, the eukaryotic cell lysis reaction is carried out at between about 5° C. to 20° C., about 9° C. to 16° C., or about 12° C. to 13° C. In some embodiments, the eukaryotic cell lysis reaction is carried at temperatures between about 25° C. to 75° C., about 30° C. to 70° C., about 35° C. to 65° C., about 40° C. to 60° C., or about 45° C. to 55° C.

In some embodiments, the eukaryotic cell lysis reaction is carried out for between about 0.01-20 minutes, between about 0.1-9.0 minutes, between about 1.0-8.0 minutes, between about 2.0-7.0 minutes, between about 3.0-6.0 minutes, between about 4.0-5.0 minutes. In some embodiments, the eukaryotic cell lysis process is stopped after about 5 minutes.

In some embodiments, the eukaryotic cell lysis solution does not contain a buffering agent. In other embodiments, the eukaryotic cell lysis solution contains a buffering agent. Examples of buffering agents include, but are not limited to 2-(N-morpholino)ethanesulfonic acid (MES), 2-Bis(2-hydroxyethyl)amino-2-(hydroxymethyl)-1,3-propanediol (Bis-Tris), 3-(—morpholino)propanesulfonic acid (MOPS), 4-(2-hydroxyethyl)-1-piperazineethanesulfonic acid (HEPES), tris(hydroxymethyl)aminomethane) (TRIS), Sodium Phosphate, Potassium Phosphate, Sodium Acetate, Sodium Carbonate/Bicaronate buffers, Sodium Acetate, N-cyclohexyl-2-hydroxyl-3-aminopropanesulfonic acid (CAPSO), N-(2-Hydroxyethyl)piperazine-N'-(4-butanesulfonic acid) (HEPBS), N-methylpiperazine, piperazine, diethanolamine, and propane 1,3-diamino.

In some embodiments, the pH of the eukaryotic cell lysis reaction is between about a pH of 6 to 9. In some embodiments, the pH is at or near neutral. Selective lysis of eukaryotic cells at a pH between about 6 to 9 or near neutral is in contrast to current methods, which emphasize alkaline conditions for eukaryotic cell lysis reactions (e.g., at pH 9.5-14). In some embodiments, performing the eukaryotic cell lysis reaction at a pH between about 6 to 9 or near neutral is advantageous over current methods known in the art due to an increase in the viability and/or structural integrity of microbial cells in the presence of some surfactants.

In some embodiments, the methods for eukaryotic cell lysis reactions described herein are advantageous over current methods known in the art because the eukaryotic cell lysis reaction methods described herein are suitable for automation in an integrated device.

Termination of Lysis of Eukaryotic Cells

In some embodiments, the eukaryotic cell lysis reaction is terminated by adding a lysis termination solution that includes at least one electrolyte to the mixture (i.e., the eukaryotic cell lysis solution/sample combination). In some embodiments, the final concentration of the electrolyte in the reaction is between about 25 mM to 850 mM, about 100 mM to 750 mM, about 150 mM to 650 mM, about 200 mM to 550 mM, about 250 mM to 450 mM, or about 300 mM to 400 mM. Electrolytes that can be added to the lysis termination buffer include, but are not limited to, monovalent salts and divalent salts. In some embodiments, the termination of the eukaryotic cell lysis reaction using at least one electrolyte improves downstream processes that use anion-exchange resins (e.g., removal of eukaryotic DNA, isolation of microbial cells, lysis of microbial cells, or isolation of microbial genomic material).

In some embodiments, the electrolyte added to the lysis termination buffer comprises at least one monovalent salt. Monovalent salts include, but are not limited to sodium chloride, potassium chloride, potassium iodide, sodium iodide, lithium chloride, lithium iodide, potassium bromide, sodium fluoride, and potassium fluoride. In some embodiments, the monovalent salt alone is added to the mixture to terminate the lysis reaction. In some embodiments, no termination of the lysis process is required. In some embodiments, the lysis termination buffer has a pH below about 9. In some embodiments, the pH of the lysis termination buffer is between about 6 and 9. In some embodiments, the lysis termination buffer does not have a pH below 4.0 or above 11.0. In some embodiments, the lysis termination buffer has a pH at about neutral.

In some embodiments, the lysis termination buffer and mixture combination has a pH below about 9. In some embodiments, the lysis termination buffer and mixture combination has a pH between about 6 to 9. In some embodiments, the lysis termination buffer and mixture combination has a pH at about neutral. In some embodiments, maintaining the combination of the lysis termination buffer and mixture at a pH between about 6 to 9 or at about neutral improves downstream processing (e.g., removal of eukaryotic DNA, isolation of microbial cells, lysis of microbial cells, or amplification of microbial DNA) of the intact microbial cells.

Removing Eukaryotic DNA/RNA

In some embodiments, the separation of the eukaryotic genomic material from the intact microbial cells in the mixture or lysis termination buffer and mixture combination is performed through "selective capture" of eukaryotic genomic material or immobilization of the eukaryotic DNA without capturing or immobilization of the intact microbial cells, eukaryotic cellular debris, or other non-nucleic acid material. In some embodiments, the eukaryotic genomic material captured is eukaryotic DNA and/or RNA.

In some embodiments, an anion exchange resin is used to capture/immobilize eukaryotic genomic material. In some embodiments, an anion exchange resin is one or more weak anion-exchange resins (WAX). Examples of WAX include, but are not limited to, carboxymethyl (CM), diethylaminopropyl (ANX), diethylethanolamine (DEAE), Amberlite Ira67, Purolite A847, Amberlite Ira96, Amberlite IRA96SB, Dowex Marathon WBA, Dowex Upcore Mono WB-500, Purolite A835, Dowex Monosphere 77, and Dowex Monosphere 66. In some embodiments, the WAX resin contains at least one tertiary amine functional group.

In some embodiments, an anion exchange resin is one or more strong anion-exchange resins (SAX). Examples of SAX include, but are not limited to, —O—$CH_2$—CHOH—$CH_2$—O—$CH_2$—CHOH—$CH_2$-N±$(CH_3)_3$, Amberjet Up4000, Amberjet 9000 OH, Amberlite FPA40 CI, and Dowex Upcore Mono MA-600. In some embodiments a SAX based resin contains a quaternary amine functional group.

In some embodiments, the anion exchange resin is a combination of at least one WAX and at least one SAX.

In some embodiments, the form of the anion exchange resin is selected from fibers, membranes, sorbents, gels, and filter paper. In some embodiments, the sample with the lysed eukaryotic cells is passed through or contacted with the anion exchange resin. In some embodiments, the anion exchange resin is in a solution.

In some embodiments, the anion exchange resin is conjugated to a support substrate. Examples of a support substrate include, but are not limited to, a particle, a bead, a surface, or a sphere. In some embodiments, the support substrate is magnetic, e.g., a magnetic particle or bead. In some embodiments, the anion exchange resin is conjugated to a support substrate is in a solution.

In some embodiments, the support substrate comprises silica, glass, metal, polystyrene-based material, cellulose-based material, agarose-based material, dextran-based material, methacrylate-based material, sepharose-based material, or a combination thereof. In some embodiments, the support substrate is porous.

In some embodiments, the support substrate is a bead or sphere has a diameter between about 10 to 100 µm, between about 20 to 90 µm, between about 30 to 80 µm, between about 40 to 70 µm, or between about 50 to 60 µm.

In another embodiment, the support substrate is a bead or sphere have a diameter between about 0.01 to 10 µm, about 0.1 to 9.0 µm, about 1.0 to 8.0 µm, about 2.0 to 7.0 µm, about 3.0 to 6.0 µm, or between about 4.0 to 5.0 µm.

In some embodiments, the mixture is incubated with the anion exchange resin between about 0.1 to 10 minutes, between about 2 to 9 minute, between about 3 to 8 minutes, between about 4 to 7 minutes, or between about 5 to 6 minutes. In some embodiments, the mixture is incubated with the anion exchange resin between about 10 to 30 minutes, between about 12 to 28 minutes, between about 15 to 25 minutes, between about 18 to 23 minutes, or between about 19 to 22 minutes. In some embodiments, the mixture is incubated with the anion exchange resin for less than 1 minute.

In some embodiments, the anion exchange resin is permanently immobilized on the support substrate. In some embodiments, the immobilized anion exchange resin is contacted and/or incubated with the mixture and then the mixture is removed.

In some embodiments, at least one anion exchange resin conjugated to a support substrate, e.g., a bead or a particle, is contacted and/or incubated with the mixture. In some embodiments, after contacting and/or incubation with the mixture, the anion exchange resin conjugated to a support substrate is removed from the mixture. In another embodiment, after contacting and/or incubation with the mixture, the anion exchange resin conjugated to a support substrate is immobilized and the mixture is removed. By way of example, but not by way of limitation, in some embodiments, the anion exchange resin conjugated to a support substrate is selectively immobilized when the support substrate is a magnetized or metal bead and the magnetized or metal bead is exposed to a magnet or magnetic field.

In some embodiments, contacting and/or incubating the mixture with the anion exchange resin extracts eukaryotic DNA, e.g., human DNA (hDNA), and/or RNA from the mixture. In some embodiments, the eukaryotic DNA (and/or RNA) binds to the anion exchange resin. In some embodiments, the anion exchange resin extracts between about 5% to 100%, between about 10% to 99%, between about 15% to 85%, between about 20% to 80%, between about 25% to 75%, between about 30% to 70%, between about 35% to 65%, between about 40% to 60%, or between about 45% to 55% of the eukaryotic DNA (and/or RNA), e.g., hDNA, from the mixture. In some embodiments, the anion exchange resin extracts over 95% of the eukaryotic DNA from the mixture.

Lysing of Microorganisms

In some embodiments, wherein it is desirable to assay the panel listed in Tables 1-5 inclusive for bacteria and/or fungi, it is preferred to ensure that the microbial lysis step be effective on all targets. This process, as well as the process for preparing the reagents, is illustrated in detail in WO 2016/044621A1. In some embodiments, the mixture (or lysis termination solution and mixture combination) with the eukaryotic DNA removed (hereinafter "isolated microbial cell sample") contains one or more microbial cells. In some embodiments, the isolated microbial cell sample is subjected to further processing. In some embodiments, the isolated microbial cell sample is contacted with a microbial cell lysis solution.

In some embodiments, the microbial cells are lysed using a lysis solution including one or more chemical lysis agents. In some embodiments, the chemical lysis agents include, but are not limited to, cationic detergents, non-ionic detergents, zwitterionic detergents, and enzymes.

In some embodiments, the microbial lysis reaction is performed at a pH between about 6 to 9 or at a neutral pH.

In some embodiments, the microbial lysis solution also includes one or more of the following: enzymes, detergents, and other components such as salts, buffering agents, and metal chelators.

In some embodiments, multiple lysis solutions are used. In some embodiments, the multiple lysis buffers are added in a step wise fashion. In some embodiments, only a single microbial lysis solution is used.

In some embodiments, the microbial lysis reaction is heated to between about 15° C. to 50° C., about 20° C. to 45° C., about 25° C. to 40° C., or about 30° C. to 35° C. In some embodiments, the microbial lysis reaction is performed at room temperature.

In some embodiments, the microbial lysis solution includes one or more of the following enzymes or enzyme groups:lysozyme, lyticase, zymolyase, mutanolysin, and lysostaphin. In some embodiments, the one or more enzymes are stored in dry or pelleted form, where upon re-suspension of the respective enzyme, the enzyme reaches the concentrations identified below.

In some embodiments, the lysozyme concentration in the microbial lysis solution is between about 5 to 200 mg/ml, about 1 to 150 mg/ml, 5 to 175 mg/ml, about 15 to 140 mg/ml, about 20 to 100 mg/ml, about 30 to 95 mg/ml, about 45 to 75 mg/ml, about 50 to 62 mg/ml, or between any two of the previously disclosed concentrations.

In some embodiments, the lysozyme concentration in the microbial lysis reaction (e.g., a solution including the microbial lysis solution and the isolated microbial cell sample) is between about 0.01 to 1 mg/ml, about 0.1 to 10 mg/ml, 0.5 to 15 mg/ml, about 1 to 20 mg/ml, about 0.3 to 8 mg/ml, about 0.7 to 7 mg/ml, about 0.2 to 0.9 mg/ml, about 0.05 to 0.35 mg/ml, or between any two of the previously disclosed concentrations.

In some embodiments, the lyticase concentration in the microbial lysis solution is between about 500 to 50,000 U/ml, about 250 to 10,000 U/ml, 425 to 8,000 U/ml, about 300 to 6,000 U/ml, about 400 to 5,000 U/ml, about 1,000 to 4,750 U/ml, about 1,500 to 4,500 U/ml, about 2,000 to 6,500 U/ml, about 2,500 to 5,500 U/ml, about 3,000 to 15,000 U/ml, or between any two of the previously disclosed concentrations.

In some embodiments, the lyticase concentration in the microbial lysis reaction is between about 1 to 1000 U/ml, about 5 to 200 U/ml, 20U to 800 U/ml, about 30 to 700 U/ml, about 40 to 600 U/ml, about 50 to 500 U/ml, about 60 to 400 U/ml, about 70 to 300 U/ml, about 80 to 200 U/ml, about 90 to 100 U/ml, or between any two of the previously disclosed concentrations.

In some embodiments, the zymolyase concentration in the microbial lysis solution is between about 500 to 50,000 U/ml, about 250 to 10,000 U/ml, 425U to 8,000 U/ml, about 300 to 6,000 U/ml, about 400 to 5,000 U/ml, about 1,000 to 4,750 U/ml, about 1,500 to 4,500 U/ml, about 2,000 to 6,500 U/ml, about 2,500 to 5,500 U/ml, about 3,000 to 15,000 U/ml, or between any two of the previously disclosed concentrations.

In some embodiments, the zymolyase concentration in the microbial lysis reaction is between about 1 to 1000 U/ml, about 5 to 200 U/ml, 20U to 800 U/ml, about 30 to 700 U/ml, about 40 to 600 U/ml, about 50 to 500 U/ml, about 60 to 400 U/ml, about 70 to 300 U/ml, about 80 to 200 U/ml, about 90 to 100 U/ml, or between any two of the previously disclosed concentrations.

In some embodiments, the mutanolysin concentration in the microbial lysis solution is between about 500 to 50,000 U/ml, about 250 to 10,000 U/ml, 425 to 8,000 U/ml, about 300 to 6,000 U/ml, about 400 to 5,000 U/ml, about 1,000 to 4,750 U/ml, about 1,500 to 4,500 U/ml, about 2,000 to 6,500 U/ml, about 2,500 to 5,500 U/ml, about 3,000 to 15,000 U/ml, or between any two of the previously disclosed concentrations.

In some embodiments, the mutanolysin concentration in the microbial lysis reaction is between about 1 to 1000 U/ml, about 5 to 200 U/ml, 20 to 800 U/ml, about 30 to 700 U/ml, about 40 to 600 U/ml, about 50 to 500 U/ml, about 60 to 400 U/ml, about 70 to 300 U/ml, about 80 to 200 U/ml, about 90 to 100 U/ml, or between any two of the previously disclosed concentrations.

In some embodiments, the lysostaphin concentration in the microbial lysis solution is between about 500 to 50,000 U/ml, about 250 to 10,000 U/ml, 425U to 8,000 U/ml, about 300 to 6,000 U/ml, about 400 to 5,000 U/ml, about 1,000 to 4,750 U/ml, about 1,500 to 4,500 U/ml, about 2,000 to 6,500 U/ml, about 2,500 to 5,500 U/ml, about 3,000 to 15,000 U/ml, or between any two of the previously disclosed concentrations.

In some embodiments, the lysostaphin concentration in the microbial lysis reaction is between about 1 to 1000 U/ml, about 5 to 200 U/ml, 20 to 800 U/ml, about 30 to 700 U/ml, about 40 to 600 U/ml, about 50 to 500 U/ml, about 60 to 400 U/ml, about 70 to 300 U/ml, about 80 to 200 U/ml, about 90 to 100 U/ml, or between any two of the previously disclosed concentrations.

In some embodiments, one or more salts are added to the microbial lysis solution. In some embodiments, the concentration of the monovalents salts is between about 50 mM and 6 M, about 150 mM and 5 M, about 350 mM and 4.5 M, about 550 mM and 4 M, about 900 mM and 3.75 M, about 1 M and 3.5 M, or between any two of the previously disclosed concentrations. In some embodiments, the salt comprises one or more monovalent salts. By way of example, but not by way of limitation, in some embodiments, the monovalent salt is one or more of NaCl, KCl, and/or LiCl.

In some embodiments, the salt concentration in the microbial lysis reaction is between about 50 mM and 800 mM, about 100 mM and 700 mM, about 200 mM and 600 mM, about 300 mM and 500 mM, and about 350 mM and 450 mM, or between any two of the previously disclosed concentrations.

In some embodiments, the one or more monovalents salts is stored in dry or pelleted form, where upon re-suspension of the respective salt, the salt reaches the concentrations identified above.

In some embodiments, an enzymatic reaction time is between about 1-60 minutes, about 5-55 minutes, about 10-45 minutes, about 15-40 minutes, about 20-35 minutes, or about 25-30 minutes.

In some embodiments, DNA contaminants in the enzymatic reaction are removed or rendered non-amplifiable or unamplifiable. In some embodiments, removal of DNA is achieved using ion exchange resins.

In some embodiments, at least one DNA intercalating dye is added to the microbial lysis solution. In some embodiments, the DNA intercalating dyes are dyes that create a covalent bond to both DNA strands after activation with a light source of the appropriate wavelength and dosage. Without wishing to be bound by theory, in some embodiments, the covalent bond renders at least some of the DNA present in the sample unamplifiable. By way of example, but not by way of limitation, in some embodiments, the DNA intercalating dye include, but are not limited to, ethidium monoazide (EMA) and propidium monoazide (PMA).

In some embodiments, the concentration of the DNA intercalating dye in the microbial lysis solution is between about 0.01 μM to 1.0 μM, about 0.1 μM to 0.9 μM, 0.2 11M to 0.8 04, about 0.3 μM to 0.7 μM, or about 0.4 μM to 0.6 μM, or between any two of the previously disclosed concentrations.

In some embodiments, the microbial lysis solution also includes one or more nucleases. In some embodiments, the nucleases are neutralized prior to usage of the microbial lysis solution. The exact nucleases used depend on the downstream sequences of interest. By way of example, but not by way of limitation, in some embodiments, the nucleases are selected from, but not limited to, EcoRI, HindIII, Sail, HhaI, DdeI, RsaI, Sau3AI and MspI.

In some embodiments, the microbial lysis solution includes one or more detergents. In some embodiments, the detergent is a zwitterionic detergent. In some embodiments, the zwitterionic detergent is from the sulfobetaine families. By way of example, but not by way of limitation, in some embodiments, sulfobetaine detergents include, but are not limited to, N-Decyl-N,N-dimethyl-3-ammonio-1-propanesulfonate, N-Decyl-N,N-dimethyl-3-ammonio-1-propanesulfonate, N-Dodecyl-N,N-dimethyl-3-ammonio-1-propanesulfonate, N-Hexadecyl-N,N-dimethyl-3-ammonio-1-propanesulfonate, N-Octadecyl-N,N-dimethyl-3-ammonio-1-propanesulfonate, and 3-[N,N-Dimethyl(3-myristoylaminopropyl)ammonio]propanesulfonate.

In some embodiments, the detergents are a non-ionic detergent from the glucopyranoside family. By way of example, but not by way of limitation, in some embodiments, non-ionic glucopyranoside detergents include, but are not limited to, 3-acetylumbelliferyl b-D-glucopyranoside, N-amyl b-D-glucopyranoside decyl b-D-thioglucyranoside, n-dodecyl b-D-glucopyranoside, hexadecyl b-D-glucopyranoside, hexyl b-D-glucopyranoside, methyl a-D-glucopyranoside, octyl b-D-glucopyranoside, and phenyl-a-D-glucopyranoside.

In some embodiments, the detergent is a cationic detergent. By way of example, but not by way of limitation, in some embodiments, cationic detergents include, but are not limited to, alkyltrimethylammonium bromide, hexadecyltrimethylammonium bromide, hexadecylpyridinium bromide, myristyltrimethylammonium bromide, benzyldodecyldimethylammonium bromide, hexadecyl(2-hydroxyethyl)dimethylammonium, hexadecylpyridinium chloride, hexadecyltrimethylammonium chloride, or tetrakis (decyl)ammonium bromide. In some embodiments, the concentration of cationic detergents is between about 1-100× critical micelle concentration (CMC).

In some embodiments, a single detergent from the sulfobetaine and glucopyranoside family is added to the microbial lysis solution. In some embodiments, one or more detergents from the sulfobetaine family and the glucopyranoside family are added to the microbial lysis solution. Additionally, or alternatively, in some embodiments, the microbial lysis solution includes one or more cationic detergents. By way of example, but not by way of limitation, in some embodiments, cationic detergents include alkyltrimethylammonium bromide, amprolium hydrochloride, benzalkonium chloride, benzyldimethyldodecylammonium chloride, benzyldimethyltetradecylammonium chloride, benzyldodecyldimethylammonium bromide, cetylpyridinium chloride, cetyltrimethylammonium bromide, dimethyldioctadecylammonium bromide, dodecylethyldimethylammonium bromide, dodecyltrimethylammonium bromide, ethylhexadecyldimethylammonium bromide, hexadecylpyridinium bromide, hexadecylpyridinium chloride, hexadecyltrimethylammonium bromide, methylbenzethonium chloride, myristyltrimethylammonium bromide, oxyphenonium bromide, tetraheptylammonium bromide, tetrakis(decyl)ammonium bromide, tetrakis(decyl)ammonium bromide, and tricaprylylmethylammonium chloride.

In some embodiments, the concentration of the individual detergent is dependent on the critical micelle concentration (CMC) of the specific detergent in the microbial lysis reaction. In some embodiments, each detergent concentration in the microbial lysis solution is between about to 1 1,000, about 25 to 12,500, about 50 to 8,000, about 75 to 7,000, about 95 to 8,500, or about 98 to 6,750 times the CMC. In some embodiments, the detergent concentration in the microbial lysis solution is between about 100 to 5,000, about 125 to 9,000, about 200 to 8,000, about 400 to 7,000, or about 500 to 6,000 times the CMC.

In some embodiments, the detergent concentration in the microbial lysis solution is between about 100 to 1000, about 200 to 900, about 300 to 800, about 400 to 700, or about 500 to 600 times the CMC. In some embodiments, each detergent concentration in the microbial lysis reaction is between about 0.1 to 100, about 1.0 to 90, about 10 to 80, about 20 to 70, about 30 to 60, or about 40 to 50 times the CMC.

In some embodiments, the detergents (either as a group or individually, or any combination thereof) are stored in dry or pelleted form, where upon re-suspension of the respective detergent, the detergent reaches the concentrations identified above.

In some embodiments, the microbial lysis solution includes one or more metal chelators. By way of example, but not by way of limitation, in some embodiments, metal chelators include, but are not limited to, ethylene-glycoltetra acetic acid (EGTA) and ethylenediaminetetraacetic acid (EDTA). In some embodiments, the concentration of the metal chelators in the microbial lysis solution is between about 50 mM to 1.0 M, about 100 mM to 0.75 M, about 110 mM to 500 mM, about 125 mM to 500 mM, about 125 mM to 450 mM, or between any two of the previously disclosed concentrations. In some embodiments, the concentration of the metal chelators in the microbial lysis reaction is between about 5 mM to 250 mM, about 10 mM to 100 mM, about 15 mM to 90 mM, about 20 mM to 80 mM, about 125 mM to 450 mM, or between any two of the previously disclose concentrations.

In some embodiments, the metal chelators are stored in dry or pelleted form, where upon re-suspension of the metal chelators, the metal chelators reach the concentrations identified above.

In some embodiments, the microbial lysis solution includes one or more reducing agents. By way of example, but not by way of limitation, in some embodiments, the reducing agent is 2-mercaptoethanol or dithiothreitol. In some embodiments, the concentration of the reducing agent in the microbial lysis solution is between about 10 mM to 20 M, about 15 mM to 15 M, about 50 mM to 14 M, about 100 mM to 14 M, or about 1 10 mM to 15 M, or between any two of the previously disclosed concentrations.

In some embodiments, the concentration of the reducing agent in the microbial lysis reaction is between about 1 mM to 100 mM, about 10 mM to 90 mM, about 20 mM to 80 mM, about 30 mM to 70 mM, about 40 mM to 60 mM, or about 45 mM to 55 mM, or between any two of the previously disclosed concentrations.

In some embodiments, the reducing agents are stored in dry or pelleted form, where upon re-suspension of the respective reducing agent, the reducing agent reaches the concentrations identified above.

In some embodiments, the microbial cell lysis reaction is performed at a pH below about 9. In some embodiments, the microbial cell lysis reaction is performed at a pH between about 6 to 9.

In some embodiments, the microbial cell lysis reaction is performed at about a neutral pH. In some embodiments, the microbial cell lysis methods disclosed herein, lead to the release of high molecular weight microbial DNA. Without wishing to be beyond by theory, in some embodiments, the microbial cell lysis methods disclosed herein lead to reduced shearing of microbial genetic materials during the microbial cell lysis and promote the presence of high molecular weight microbial DNA in the lysis solution. In some embodiments, high molecular weight microbial DNA is between about 2 kbp to 200 kbp, about 10 kbp to 190 kbp, about 20 kbp to 180 kbp, about 30 kbp to 170 kbp, about 40 kbp to 160 kbp, about 50 kbp to 150 kbp, about 60 kbp to 140 kbp, about 70 kbp to 130 kbp, about 80 kbp to 120 kbp, or about 90 kbp to 110 kbp.

Isolation of Microbial Genomic Material

Having lysed the microbial content of the blood-based solution, in some embodiments it is preferred to isolate or purify the microbial genomic-DNA (herein 'gDNA') from the non-DNA components of the sample. In contrast to the majority of current methods employing the addition of chaotropic salts to achieve the same, our preferred method entails the use of anion exchange resins for capturing free microbial gDNA, and washing away non-DNA components from the system. Upon elution, and in some embodiments, the isolated gDNA has the advantage of being of sufficient purity such that it does not need to be diluted prior to downstream enzymatic amplification.

In some embodiments, after microbial cell lysis, the microbial genetic material is isolated and/or purified. In some embodiments, the genetic material isolated and/or purified is RNA or DNA. In some embodiments, the DNA is single stranded DNA (ssDNA) or double stranded DNA (dsDNA).

In some embodiments, microbial genetic material is isolated by contacting the microbial lysis reaction solution with anion exchange materials packed into columns, wherein the anion exchange material is used for the adsorption and subsequent elution of microbial genetic material. In some embodiments, a solution of known ionic strength and pH enable binding of nucleic acids to the anion exchange column and enable lesser-bound contaminants to be washed away. By way of example, but not by way of limitation, in some embodiments, conditions for selectively binding microbial genetic material with anion exchange materials include contacting the microbial lysis reaction solution with anion exchange in one or more of the following conditions: the contacting reaction is performed at a pH of between about 6 to 9, about 4.5 to 7, or about 8 to 9.5, and the contacting reaction has a monovalent salt concentration of between about 100 mM to 750 mM, about 450 mM to 1.75 M, or about 50 mM to 350 mM. The bound genetic material may then be eluted after contaminants have been removed.

In some embodiments, an anion exchange resin is used to capture/immobilize microbial genomic material. In some embodiments, an anion exchange resin is one or more weak anion-exchange resins (WAX). Examples of WAX include, but are not limited to, carboxymethyl (CM), diethylaminopropyl (ANX), diethylethanolamine (DEAE), Amberlite Ira67, Purolite A847, Amberlite Ira96, Amberlite IRA96SB, Dowex Marathon WBA, Dowex Upcore Mono WB-500, Purolite A835, Dowex Monosphere 77, and Dowex Monosphere 66. In some embodiments, the WAX resin contains a tertiary amine functional group.

In some embodiments, an anion exchange resin is one or more strong anion-exchange resins (SAX). Examples of SAX include, but are not limited to, —O—$CH_2$—CHOH—$CH_2$—O—$CH_2$—CHOH—$CH_2$-N±$(CH_3)_3$, Amberjet Up4000, Amberjet 9000 OH, Amberlite FPA40 CI, and Dowex Upcore Mono MA-600. In some embodiments, a SAX based resin contains a quaternary amine functional group.

In some embodiments, the anion exchange resin is a combination of WAX and SAX.

In some embodiments, the form of the anion exchange resin is selected from fibers, membranes, sorbents, gels, and filter paper. In some embodiments, the sample with the lysed eukaryotic cells is passed through or contacted with the anion exchange resin. In some embodiments, the anion exchange resin is in a solution.

In some embodiments, the anion exchange resin is conjugated to a support substrate. Examples of a support substrate include, but are not limited to, a particle, a bead, a surface, or a sphere. In some embodiments, the support substrate is magnetic, e.g., a magnetic particle or bead. In some embodiments, the anion exchange resin is conjugated to a support substrate is in a solution.

In some embodiments, the support substrate comprises silica, glass, metal, polystyrene-based material, cellulose-based material, agarose-based material, dextran-based material, methacry late-based material, sepharose-based material, or a combination thereof. In some embodiments, the support substrate is porous.

In some embodiments, the support substrate is a bead or sphere has a diameter between about 10 to 100 μm, between about 20 to 90 μm, between about 30 to 80 μm, between about 40 to 70 μm, or between about 50 to 60 μm.

In another embodiment, the support substrate is a bead or sphere have a diameter between about 0.1 to 10 μm, between about 1.0 to 9.0 μm, between about 2.0 to 8.0 μm, between about 3.0 to 7.0 μm, or between about 4.0 to 6.0 μm.

In some embodiments, the microbial lysis reaction is incubated with the anion exchange resin between about 0.1 to 10 minutes, between about 2 to 9 minute, between about 3 to 8 minutes, between about 4 to 7 minutes, or between about 5 to 6 minutes. In some embodiments, the microbial lysis reaction is incubated with the anion exchange resin between about 10 to 30 minutes, between about 12 to 28 minutes, between about 15 to 25 minutes, between about 18 to 23 minutes, or between about 19 to 22 minutes. In some embodiments, the microbial lysis reaction is incubated with the anion exchange resin for less than 1 minute.

In some embodiments, the microbial lysis reaction is incubated with the anion exchange resin between about 0.01 to 10 minutes, about 0.1 to 9 minutes, 1 to 8 minutes, about 2 to 7 minutes, 3 to 6 minutes, or about 4 to 5 minutes beyond that which is required to lysis the microbial cells.

In some embodiments, the anion exchange resin is permanently immobilized on the support substrate. In some embodiments, the immobilized anion exchange resin is contacted and/or incubated with the mixture and then the mixture is removed.

In some embodiments, at least one anion exchange resin conjugated to a support substrate, e.g., a bead or a particle (e.g., a microparticle), is contacted and/or incubated with the mixture. In some embodiments, after contacting and/or incubation with the microbial lysis reaction, the anion exchange resin conjugated to a support substrate is removed from the microbial lysis reaction. In another embodiment, after contacting and/or incubation with the microbial lysis reaction, the anion exchange resin conjugated to a support substrate is immobilized and the microbial lysis reaction is removed. By way of example, but not by way of limitation, in some embodiments, the anion exchange resin conjugated to a support substrate is selectively immobilized when the support substrate is a magnetized or metal bead and the magnetized or metal bead is exposed to a magnet or magnetic field.

In some embodiments, the beads or particle are packed into a column. In some embodiments, the beads or particle are free floating form.

In some embodiments, the anion-exchange-microparticles is a weak anion exchange material bound to magnetizable microspheres. In some embodiments, the anion-exchange-microparticles is a strong anion exchange material bound to magnetizable microspheres.

In some embodiments, the anion-exchange-microparticles is a weak anion exchange material bound to porous agarose based-microspheres. In some embodiments, the anion-exchange-microparticles is a strong anion exchange material bound to porous agarose based-microspheres.

In some embodiments, after binding the microbial genetic material to the anion-exchange-microparticles, the anion-exchange-microparticles are washed using a wash buffer or wash solution.

In some embodiments, a salt concentration of the wash solution is elevated as compared to the salt concentration during binding of the microbial genetic material. In some embodiments, the pH of the wash conditions is altered to achieve more stringent wash conditions. In some embodiment, the pH of the wash solution is between about 3.0 to 7.5, about 3.5 to 7.0, about 4.0 to 6.5, about 4.5 to 6.0, or about 5.0 to 5.5.

In some embodiments, the wash solution has a salt concentration between about 0.5 M to 3.0 M, about 0.75 M to 2.75 M, about 1.0 M to 2.5 M, about 1.25 M to 2.25 M, or about 1.5 M to 2.0 M.

In some embodiments, a more alkaline wash solution is preferred. In some embodiments, the pH of the wash solution is between about 9.5 to 10.5, about 10.0 to 11.0, about 10.5 to 11.5, about 11.0 to 12.0, or about 11.5 to 12.5. In some embodiments, the more alkaline solution has a salt concentration of less than about 0.5M, between about 0 mM to 100 mM, 50 mM-200 mM, 100 mM-300 mM, or about 200 mM –500 mM.

In some embodiments, the wash solution includes one or more surfactants. By way of example, but not by way of limitation, in some embodiments, surfactants include, but are not limited to, Tween and Triton-X. In some embodiments, the Tween and/or Triton-X concentration is between about 0.01% to 1.0% (v/v), about 0.1% to 0.9% (v/v), about 0.2% to 0.8% (v/v), about 0.3% to 0.7% (v/v), or about 0.4% to 0.6% (v/v). In some embodiments, the wash solution includes one or more detergents. By way of example, but not by way of limitation, in some embodiments, detergents include, but are not limited to, zwitterionic detergents. In some embodiments, the zwitterionic detergent concentration is between about 0.1× to 350× CMC, about 1.0× to 300× CMC, about 10× to 250× CMC, about 50× to 200× CMC, or about 100× to 150× CMC.

In some embodiments, the methods for isolating the microbial DNA includes an elution step. In some embodiments, competition of the isolation process is facilitated by eluting or removing the DNA off of the anion-exchange-microparticles.

In some embodiments, the pH of the elution buffer is between about 12 to 13.5. The use of an elution buffer with a pH greater than about 12 is not commonly used in the art.

In some embodiments, the elution buffer comprises of a buffering agent such as sodium phosphate or potassium phosphate. In some embodiments, the concentration of sodium phosphate or potassium phosphate is between about 0.01 M to 1 M, about 0.1 M to 1.8 M, about 0.4 M to 1.6 M, about 0.8 M to 1.4 M, or about 1.0 M to 1.2 M. In some embodiments, no buffering agent is required.

Additionally, or alternatively, in some embodiments, the elution buffer comprises sodium hydroxide or potassium hydroxide. In some embodiments, the concentration sodium hydroxide or potassium hydroxide is between about 10 to 500 mM, about 30 to 450 mM, about 50 to 400 mM, about 70 to 350 mM, about 90 to 300 mM, about 1 10 to 250 mM, or about 130 to 200 mM.

In some embodiments, the elution buffer also includes one or more monovalent salts. By way of example, but not by way for limitation, in some embodiments, monovalent salts include, but are not limited to, NaCl, KCl and LiCl.

In some embodiments, the concentration of the one or more monovalent salts in the elution buffer is between about 0 mM to 200 mM, about 25 mM to 175 mM, about 50 mM, to 150 mM, about 75 mM to 125 mM, or about 90 mM to 110 mM. The use of an elution buffer with monovalent salt concentrations less than about 200 mM is not commonly used in the art. In some embodiments, the elution buffer does not contain any monovalent salts.

In some embodiments, the isolation of microbial genetic material also includes a nucleic acid (e.g., DNA or RNA) purification step. In some embodiments, the purification step includes using chaotropic salts.

In some embodiments, the nucleic acid purification step includes the addition of about 6 M to 9 M of guanidinium chloride or guanidinium thiocyanate. Without wishing to be bound by theory, in some embodiments, the purification allows for efficient binding of a nucleic acid to a silica based solid-phase material such as a filter/membrane, a filter/membrane embedded in a gravity or spin column, or a bead/microsphere/magnetic particle. In some embodiments, subsequent washing of the solid-phase material further removes most of the remaining salts and other hold-over components. In some embodiments, washing is completed using a salt rich, alcohol based buffer. In some embodiments, less than 2 M of guanidinium chloride or guanidinium thiocyanate is added.

In some embodiments, the above isolated microbial genetic material is eluted through the addition of a water-based solution with a pH that is greater than about 5.0. In some embodiments, the isolated microbial genetic material is eluted through the addition of a water-based solution with a pH between about 6 to 9. In some embodiments, the isolated microbial genetic material is eluted through the addition of a water-based solution with a pH that is greater than about 10.

In some embodiments, no additional purification or desalting is required after eluting the genomic material from the anion-exchange resin.

In some embodiments, the gDNA is concentrated and/or purified using a size exclusion membrane following elution from the anion exchange resin. In some embodiments, the gDNA is concentrated and/or purified by applying one or more binding, wash, and/or elution steps to the anion exchange resin. In some embodiments, the concentration and/or purification comprises one or more of the following: (i) one or more binding steps; one or more washing steps; and one or more elution steps. Those skilled in the art will be to modify the process to meet purity and volume restrictions as required for optimal operation. Notwithstanding the above, this process, as well as the process for preparing the reagents, is illustrated in detail in WO2016044621A1.

Enzymatic Amplification of the Microbial Genomic Material

In some embodiments, it is preferred to enzymatically amplify the microbial genetic material (microbial gDNA). In some embodiments, the isolated microbial genetic material is subject to amplification. In some embodiments, the genetic material amplified is RNA or DNA. In some embodiments, the DNA is single stranded DNA (ssDNA) or double stranded DNA (dDNA). In some embodiments, the DNA is ribosomal DNA (rDNA). In some embodiments, microbial genetic material specific to a species or genus of microorganisms is amplified.

In some embodiments, enzymatic amplification can be achieved either through isothermal amplification or thermal-cycling amplification processes. In some embodiments, polymerase chain reaction, or PCR, is the preferred method of enzymatic amplification which is a well-known method of thermal-cycling based enzymatic amplification.

In some embodiments, a single amplification reaction is performed, e.g., the gDNA is not split into more than one reaction. Without wishing to be bound by theory, this can increase sensitivity.

In some embodiments, it is preferred to utilize a minimal set of primer pairs, for example rDNA primers, for the entire range of pathogens to be assayed. Without wishing to be bound by theory, this has been shown to increase sensitivity, and decrease amplification bias of specific genomic regions. By way of example but without limitation, should the user choose to assay the entire panel identified in Tables 1-3 & 5 utilizing rDNA, a suitable primer mixture may include a single primer pair for amplifying bacterial gDNA, and a single primer pair for amplifying fungal gDNA. In some embodiments, the addition of one or more targets from Table 4 would require one or more primer pairs. In some embodiments, the primer binding sites are highly conserved among all target microorganism. Primer pairs for amplifying conserved regions of interest are well known to those skilled in the art. Designing primer pairs for specific genomic regions are also well known to those skilled in the art.

In some embodiments, some or all of the following primers can be used: CCC CCC CCT CAG TTA TCG TTT ATT TGA TAG TAC C (SEQ ID NO: 572); CCC CCC CCT CAG TTA TCG TTT ATT TGA TAG TTC C (SEQ ID NO: 573); CCC TTC CCA GAG TTT GAT CAT GGC TCA G (SEQ ID NO: 574); CCC TTC CAG AGT TTG ATC CTG GCT CAG (SEQ ID NO: 575); CCC CCC GGT TAC CTT GTT ACG ACT T (SEQ ID NO: 576); CCC CCGG CTA CCT TGT TAC GACT T (SEQ ID NO: 577); CCC TTC CCT GAT GAC TCG TGC CTA CTA (SEQ ID NO: 578); CCC TCT CCC TGA TGA CTT GCG CTT ACT A (SEQ ID NO: 579); TGT TGC AAG AAT ACG GAC TCA (SEQ ID NO: 580); CTT CAC AGA GCC ACC GTA (SEQ ID NO: 581).

In some embodiments, the amplicon is greater than about 400 bp. In some embodiments, the amplicon is between about 400 to 4000 bp, about 700 to 3700 bp, about 1000 to 3400 bp, about 1300 to 3100 bp, about 1600 to 2700 bp, about 1900 to 2400 bp, or about 2100 to 2200 bp. In some embodiments, use of amplicons of the lengths disclosed above are advantageous for downstream processing (e.g., detection and identification of microbial genetic materials) in the methods disclosed herein.

In some embodiments, the amplification product is purified. By way of example, but not by way of limitation, in some embodiments, a method for purifying the amplification product includes the reversible binding or absorption of the amplicon onto glass or silica fibers or particles in combination with chaotropic salts followed by their washing and elution. In some embodiments, purification methods include, but is not limited to, precipitation in an alcohol based solutions (e.g., such as ethanol or isopropanol), contacting with anion exchange resins, or size exclusion filters. In some embodiments, the cleaning-up of the amplification product removes excess primers, dNTPs, salts and other components that may interfere with downstream processes.

In some embodiments, no purification process is required, and the amplification product/solution can be used as is in downstream processes.

In some embodiments, the microbial genetic material is amplified by PCR and the number of PCR cycles are modified to adjust for sample input volume, sample type, and/or microbial load assessments. In some embodiments, the microbial genetic material is amplified by isothermal amplification and the amplification times are modified to adjust for sample input volume, sample type, and/or microbial load assessments.

Notwithstanding the above, this process, as well as the process for preparing the reagents, is illustrated in detail in WO 2016/044621A1.

DIANA-Based Capture and/or Immobilization of Amplified Genomic Material

In some embodiments, the amplified microbial genetic materials are contacted or incubated with a plurality of DIANAs and the amplified microbial genetic materials are detected. In some embodiments, the incubation of DIANAs and the microbial genetic material (e.g., amplified microbial DNA) is at a temperature between about 20° C. to 65° C. In some embodiments, the incubation of DIANAs and the microbial genetic material is at a temperature between about 25° C. to 65° C. In some embodiments, the incubation of DIANAs and the microbial genetic material is at a temperature between about 30° C. to 65° C. In some embodiments, the incubation of DIANAs and the microbial genetic material is at a temperature between about 37° C. to 65° C. In some embodiments, the incubation of DIANAs and the microbial genetic material is at a temperature between about 45° C. to 65° C. In some embodiments, the incubation of DIANAs and the microbial genetic material is at a temperature between about 55° C. to 65° C. In some embodiments, the the incubation of DIANAs and the microbial genetic material is at a temperature of about 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., or 65° C. In some embodiments, the incubation of DIANAs and the microbial genetic material (e.g., amplified microbial DNA) is at a temperature between about 65° C. to 99° C.

Provided herein are methods that provide for the invasion of DIANAs at the reduced temperatures of above 25° C. DIANAs in 10 minutes or less. As is described in more detail below, the use of invasion temperatures below 65° C. for invasion reactions lasting 10 minutes or less is new and advantageous.

In some embodiments, the invasion reaction last between about 0.1 to 5 minutes, about 1 to 10 minutes, about 5 to 30 minutes, or about 10 to 60 minutes. In some embodiments, the invasion reaction lasts less than 10 minutes, less than 9 minutes, less than 8 minutes, less than 7 minutes, less than 6 minutes, less than 5 minutes, less than 4 minutes, less than 3 minutes, less than 2 minutes, or less than 1 minute, for example, 1 minute, 2 minutes, 3 minutes, 4 minutes, 5 minutes, 6 minutes, 7 minutes, 8 minutes, 9 minutes, or 10 minutes.

In some embodiments, the composition of the DIANA invasion solution is depicted in WO 2016/044621A1.

In some embodiments, the invasion solution includes a buffering agent. By way of example, but not by way of limitation, in some embodiments, the buffering agent includes, but is not limited to, tris, sodium-phosphate, and potassium phosphate.

In some embodiments, the concentration of the buffering agent is between about 1 mM to 500 mM, about 50 mM to 450 mM, about 100 mM to 400 mM, about 150 mM to 350 mM, or about 200 mM to 300 mM. In some embodiments, no buffering agent is required. In some embodiments, the pH of the invasion solution is between about pH 6 and about pH 9. In some embodiments, the invasion solution includes one or more monovalent salts. In some embodiments, the monovalent salt is NaCl or KCl. In some embodiments, the concentration of monovalent salt is between about 1 mM to 150 mM, about 5 mM to 145 mM, about 15 mM to 130 mM, about 25 mM to 1 15 mM, about 35 mM to 100 mM, about 45 mM to 85 mM, or about 55 mM to 70 mM. In some embodiments, the invasion solution contains no monovalent salts. The disclosed salt concentrations of the invasion assay are below the salt concentration used in standard hybridization assays.

In some embodiments, the invasion solution include one or more surfactants. In some embodiments, the surfactant reduces non-specific binding. By way of example, but not by way of limitation, surfactants include, but are not limited to, Tween-20, or TritonX-100. In some embodiments, the concentration of the surfactant in the invasion solution is between about 0.01% to 1.0% (v/v), about 0.1% to 0.9% (v/v), about 0.2% to 0.8% (v/v), about 0.3% to 0.7% (v/v), or about 0.4% to 0.6% (v/v).

In some embodiments, the invasion solution includes components to vary the excluded volume (e.g., crowding agents). By way of example, but not by way of limitation, crowding agents include, but are not limited to, polyethylene glycol (PEG), PEG-200, PEG-250, PEG-300, PEG-400, PEG-500, PEG-750, PEG-1,000, PEG-9,500, PEG-2,000, PEG-4,000, PEG-5,000, PEG-6,000, PEG-8,000, PEG-10,000, PEG-12,000, PEG-13,000, PEG-20,000, dextrans (DX), polyvinyl-alcohols (PVA), Ficolls (FC), DX-1,000, DX-5,000, DX-12,000, DX-50,000, DX-80,000, PVA 89k-98k, PVA 85k-124k, PVA 130k, PVA 31k-50k, PVA 50k-80k, PVA 70k-100k, PVA 90k-120k, PVA 170k-250k, PVA 61k, PVA 31k, PVA 130k, PVA 67k, PVA 27k, PVA 25k, FC-400, FC-70, FC-40, glycerol, glucose, and sucrose. In some embodiments, the concentration range of the crowding agent in the invasion solution is between about 1% to 20% (v/v), about 3% to 17% (v/v), about 6% to 14% (v/v), or about 9% to 11% (v/v) of the total volume of invasion solution. In some embodiments, the invasion solution included one or more DNA denaturants. By way of example, but not by way of limitation, DNA denaturants include, but are not limited to, DMSO, formamide, and betaines.

In some embodiments, the invasion solution also includes DMSO, formamide, betaines, or a combination thereof. In some embodiments, the DMSO and/or formamide are between about 1% to 30% (v/v), about 5% to 25% (v/v), about 10% to 20% (v/v), or about 14% to 16% (v/v) of the total volume of invasion solution. In some embodiments, the concentration of the betaines in the invasion buffer is between about 0.1 M and 2.5 M, about 0.5 M and 2.0 M, or about 1.0 M and 1.5 M.

In some embodiments, the invasion solution has a pH of about 10 or more. In some embodiments, an invasion solution with a pH greater than about 10 is conducive to DNA denaturing or destabilization.

Washing

In some embodiments, a washing step is performed after DIANA invasion. In some embodiments, the wash step reduces non-specific binding. In some embodiments, the wash uses high temperature wash solutions. In some embodiments, the temperature of the wash solution is between about 60° C. and 99° C., or between 20° C. to 65° C. The composition of the preferred DIANA wash buffer is depicted in WO 2016/044621A1.

In some embodiments, the wash buffer comprises one or more of the following: 1) monovalent salt, e.g., as NaCl or KCl, at between about 50 to 650 mM, about 100 to 600 mM, about 150 to 550 mM, about 200 to 500 mM, about 250 to 450 mM, or about 300 to 400 mM; 2) buffered to a near neutral pH, for example between about 6-9; and 3) surfactants, e.g., Tween-20 or Triton X-100 at between about 0.1% to 1.0% (v/v), about 0.2% to 0.9% (v/v), about 0.3% to 0.8% (v/v), about 0.4% to 0.7% (v/v), or about 0.5% to 0.6% (v/v). In some embodiments, the wash buffer is heated.

In some embodiments, the wash buffer includes one or more DNA destabilizing or denaturing agents, e.g., DMSO, betaines, and formamide. In some embodiments, the DMSO and/or formamide are between about 10% to 30% (v/v), about 15% to 25% (v/v), about 10% to 20% (v/v), or about 14% to 16% (v/v) of the total volume of invasion solution. In some embodiments, the concentration of the betaines in the invasion buffer is between about 0.1 M and 2.5 M, about 0.5 M and 2.0 M, or about 1.0 M and 1.5 M.

In some embodiments, the pH of the wash buffer is above 9.0 and includes between about 0 mM to 300 mM, about 50 mM to 250 mM, about 100 mM to 200 mM, or about 125 mM to 175 mM of monovalent salts and/or surfactants. In some embodiments, the pH of the wash buffer is below 9.0 and includes between about 0 mM to 800 mM, about 50 mM to 750 mM, about 100 mM to 700 mM, about 150 mM to 650 mM, or about 200 mM to 600 mM, about 250 mM to 550 mM, about 300 mM to 500 mM, or about 350 mM to 450 mM of monovalent salts and/or surfactants.

By way of example, but not by way of limitation, in some embodiments, the washing step comprises washing DIANA oligomers that are sized between about 14 to 18 bases, wherein the lower wash temperature is defined as about: $T_M$(DNA)+20° C. and the upper wash temperature is 99° C.

In some embodiments, the preferred temperature for invasion and washing is dictated by the length of the DIANA probe, its base composition (i.e. GC content), and the conditions at which the reactions take place. Without wishing to be bound by theory, in some embodiments, the DIANA invasion reaction is rate limited by that which the duplex DNA region of interest can be effectively 'opened', thus exposing the nucleobases. As such, an increase in temperature is but one parameter which plays a role, which additive reagents also play a role. Further, with regards to washing conditions, and without wishing to be bound by theory, in some embodiments, the DIANA wash conditions are dependent on, as a minimum, the binding strength of the DIANA probe to the target DNA. As such, parameters such as temperature, electrolytes, pH, other additives, play a significant role in establishing the optimal condition.

By way of example, but not by way of limitation, in some embodiments, the DIANA invasion process includes using DIANA oligomers that are larger than 18 bases, wherein the lower invasion temperature is defined as about: $T_M$(DNA)+ 0.7° C. x (number of bases) and the upper invasion temperature is 99° C.

By way of example, but not by way of limitation, in some embodiments, the DIANA invasion process includes using DIANA oligomers that are smaller/shorter than 14 bases, wherein the lower invasion temperature is defined as about: $T_M$(DNA)+1.1° C. x (number of bases) and the upper invasion temperature is 99° C.

By way of example, but not by way of limitation, in some embodiments, the washing step comprises washing DIANA oligomers that are larger than 18 bases, wherein the lower wash temperature is defined as about: $T_M$(DNA)+0.9° C. x (number of bases) and the upper wash temperature is 99° C.

By way of example, but not by way of limitation, in some embodiments, the washing step comprises washing DIANA oligomers that are smaller/shorter than 14 bases, wherein the lower wash temperature is defined as about: $T_M$(DNA)+ 1.25° C. x (number of bases) and the upper wash temperature is 99° C.

Low Temperature DIANA Invasion and Wash

Without wishing to be bound by theory, the process of invasion is similar to that of hybridization wherein binding is chiefly due to, but not limited to, Watson-Crick base-pairing rules. By indicating this, the intent is to highlight that a pre-requisite for invasion is 'access' to the nucleobases, which in the case of duplex DNA (either locally or universally, and discussed below) is 'hidden' in most cases.

Without wishing to be bound by theory, the rate limiting step for DIANA invasion is the ability to open the duplex DNA thus making available the nucleobases for invasion. 'Open' does not necessarily mean that the DNA is denatured, but rather that what is known as DNA breathing is increased, where local, transient, bubbles are formed within the duplex DNA. As breathing increases these bubbles become (1) more frequent, (2) more common, (3) longer lived i.e. stable, and (4) larger. DNA breathing is a natural, physical, process depicting the competeting energetics of the negative sugar-phosphate backbone and the hydrogen bonds between the nucleobases and base-pair stacking interactions. DNA breathing may be unrelated to the presence or absence of DIANAs in the system.

Art known methods for DIANA invasion commonly described the use of temperatures at or below 37° C. At such temperatures, invasion was extremely slow—on the scale of hours. At even lower temperatures, moving towards ambient temperatures, DNA invasion becomes even slower. Cleary, a need exists for more rapid invasion in the field of rapid diagnostic technology.

Reaction conditions which enable rapid and highly efficient DNA invasion, in the 1-10-minute timeframe have recently been described. These methods are disclosed in WO 2016/044621A1. The methods disclosed in WO 2016/044621A1 can be useful at temperatures above about 65° C. (see section starting at para. [0248]).

Disclosed herein are methods for further reducing the invasion temperature to 65° C., in certain conditions, while still meeting the sub-10 min (indeed the sub 5 min) timeframe. These methods employ the use of DIANA technology with predominantly single stranded DNA or RNA. This has not been previously described.

In some embodiments, a target DNA or RNA that is predominantly single-stranded. In some embodiments, a double-stranded structure is induced locally to create the preferred conditions. While RNA is naturally single-stranded, DNA is naturally double-stranded. In some embodiments, double stranded DNA is processed to generate single stranded DNA. Processing steps include, but are not limited to enzymatic, chemical, or mechanical processing. Other processing methods are well known within the art.

Upon having in place single stranded DNA or RNA target molecules, local duplex, or hairpin, structures can be stabilized. This can be accomplished by increasing the electrolyte concentrations in the reaction mixture. In some embodiments, electrolytes are added to the invasion solution.

In some embodiments, monovalent salts are added to the invasion solution. In some embodiments, the monovalent salt is added at a concentration of above 50 mM. In some embodiments, the monovalent salt is added at a concentration of 100 mM or above. In some embodiments, the monovalent salt is added at a concentration of 200 mM or above. In some embodiments, the monovalent salt is added at a concentration of about 50 mM, 51 mM, 55 mM, 60 mM, 70 mM, 80 mM, 90 mM, 100 mM, 110 mM, 120 mM 125 mM, 130 mM, 140 mM, 150 mM, 160 mM, 170 mM, 175 mM, 180 mM, 190 mM, 200 mM, 225 mM, 250 mM, 275 mM, 300 mM, 325 mM, 350 mM, 375 mM, 400 mM, 450 mM, or 500 mM. In some embodiments, the monovalent salt is added at a concentration of from 51 mM-500 mM, from 51 mM-250 mM, from 51 mM-100 mM, or from 100 mM-200 mM.

In some embodiments, divalent salts are added to the invasion solution. In some embodiments, the monovalent salt is added at a concentration of above 5 mM. In some embodiments, the monovalent salt is added at a concentration of 7 mM or above. In some embodiments, the monovalent salt is added at a concentration of 10 mM or above. In some embodiments, the monovalent salt is added at a concentration of about 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, or 25 mM. In some embodiments, the monovalent salt is added at a concentration of from 6 mM-50 mM, from 6 mM-25 mM, from 6 mM-10 mM, or from 10 mM-20 mM.

In some embodiments, trivalent salts are added to the invasion solution. In some embodiments, the monovalent salt is added at a concentration of above 0.1 mM. In some embodiments, the monovalent salt is added at a concentration of 0.3 mM or above. In some embodiments, the monovalent salt is added at a concentration of 0.5 mM or above. In some embodiments, the monovalent salt is added at a concentration of about 0.1 mM, 0.2 mM, 0.3 mM, 0.4 mM, 0.5 mM, 0.6 mM, 0.7 mM, 0.8 mM, 0.9 mM, 1.0 mM, 1.1 mM, 1.2 mM, 1.3 mM, 1.4 mM, 1.5 mM, 2.0 mM, or 2.5 mM. In some embodiments, the monovalent salt is added at a concentration of from 0.2 mM-1.0 mM, from 0.2 mM-0.7 mM, from 0.2 mM-0.5 mM, or from 0.5 mM-1.0 mM.

In other embodiments, the invasion can be accomplished at high speed at a reduced temperature in inherently duplex nucleic acid molecules in destabilizing conditions. Without wishing to be bound by theory, the conditions described herein are not meant to enable complete denaturization of the DNA template, but rather sufficient destabilization to enable a reduce temperature for invasion. The exact nature of these conditions are dependent on the reaction solution used with regards to denaturants and electrolyte concentrations as identified in WO 2016/044621A1 and described herein, in addition to the length of the duplex target. In some embodiments, the invasion solution has a pH (either buffered or unbuffered) of about 10.2-12.2. In some embodiments, the pH is about 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, or 12.2. In some embodiments, the pH is between 10.2 and 11.0. In some embodiments, the pH is between 10.5 and 11.5. In some embodiments, the pH is between 11.0 and 12.0. In some embodiments, the pH is 10.2 or above. In some embodiments, the pH is 10.5 or above. In some embodiments, the pH is 11.0 or above. In some embodiments, the pH is 11.5 or above. In some embodiments, the preferred pH is optimized for the specific data target, reaction additives, target length and GC composition, and preferred temperature range.

In some embodiments, a wash solution, used to remove non-specific binding of DIANAs to DNA, may likewise be used at temperatures between 25° C.-65° C. In some embodiments, the aforementioned wash solution has a pH (either buffered or unbuffered) of about 10.7-12.7. In some embodiments, the pH is about 10.7, 10.8, 10.9, 11.0, 11.1, 11.2, 11.3, 11.4, 11.5, 11.6, 11.7, 11.8, 11.9, 12.0, 12.1, 12.2, 12.4, 12.4, 12.5, 12.6, or 12.7. In some embodiments, the pH is between 10.7 and 11.5. In some embodiments, the pH is between 11.0 and 11.8. In some embodiments, the pH is between 11.3 and 12.0. In some embodiments, the pH is between 11.7 and 12.7. In some embodiments, the pH is 10.7 or above. In some embodiments, the pH is 11.0 or above. In some embodiments, the pH is 11.5 or above. In some embodiments, the pH is 12.0 or above. In some embodiments, the preferred pH is optimized for the specific data target, reaction additives, target length and GC composition, DIANA length and preferred temperature range.

Detection

In some embodiments, detection of the binding of DIANAs to their respective target is through optical, chemical, electrical, or mechanical detection methods in a detection region. Method utilized for detection of the DIANAs to their respective target is depicted in WO 2016/044621A1.

In some embodiments, optical detection is through the use of fluorescence or luminescence.

In some embodiments, one or more detectable markers are positioned on the invading DIANAs. In some embodiments, the one or more detectable markers are positioned on the DNA amplicon captured via the immobilized oligomer. In some embodiments, one or more detectable markers are positioned on a second oligomer, which is universal to some or all potential targets. By way of example, but not by way of limitation, in some embodiments, the detectable markers include, but are not limited to fluorescent dyes, horseradish peroxidase (HRP), luciferase, methoxycoumarin, dansyl, pyrene, Alexa Fluor 350, AMCA, Marina Blue dye, dapoxyl dye, dialkylaminocoumarin, bimane, hydroxycoumarin, cascade blue dye, Pacific Orange dye, Alexa Fluor 405, Cascade Yellow dye, Pacific Blue dye, PyMPO, Alexa Fluor 430, Fluorescein, Alexa Fluor 488, Oregon Green 488, BODIPY 493/503, Oregon Green 514, Alexa Fluor 514, Alexa Fluor 532, BODIPY TMR, Alexa Fluor 555, Alexa Fluor 546, BODIPY 558/568, Rhodamine Red dye, Alexa Fluor 568, BODIPY 581/591, Alexa Fluor 594, Texas Red dye, Alexa Fluor 610, Alexa Fluor 633, Alexa Fluor 635, Alexa Fluor 647, Alexa Fluor 660, Alexa Fluor 680, Alexa Fluor 700, Alexa Fluor 750, and Alexa Fluor 790.

By way of example, but not by way of limitation, detectable markers enabling indirect detection include, but are not limited to, digoxigenin (DIG), biotin, or dinitrophenyl.

In some embodiments, identification of the microbial species is through DNA amplicon labeling.

In some embodiments, the primers used in the amplification are labeled during with a detectable marker prior to beginning the amplification process.

In some embodiments, modified nucleotides that either contain a tag or are modified to enable the downstream conjugation of tags are used in the amplification process. By way of example, but not by way of limitation, tag-modified nucleotides include, but are not limited to, a nucleotide modified with a diethylaminocoumarin (DEAC), Cyanine 3 (Cy3), Cyanine 5 (Cy5), Fluorescein (FITC), Lissamine, R110, R6G, Tetramethylrhodamine (TAMRA), or Texas Red dye. Examples of a modified nucleotides enabling subsequent tagging would be, but are not limited to, a nucleotide modified with an Amino-digoxigenin (DIG), Biotin, or Dinitrophenyl (DNP).

In some embodiments, the labeling of the DNA amplicon is achieved through subsequent incubation with an intercalating dye. By way of example, but not by way of limitation, intercalating dyes include, but are not limited to, PicoGreen, OliGreen, RiboGreen, SYBR Gold, SYBR Green I, SYBR Green II, SYBR Safe, TOTO-1, YOYO-1, YOYO-3, POPO-1, BOBO-1, JOJO-1, POPO-3, LOLO-1, BOBO-3, YOYO-3, TOTO-3, SYTOX-Blue, SYTOX-Green, SYTOX-Orange, SYTOX-Red, and EtBr.

In some embodiments, the DNA amplicon is first tagged with one or more DIANAs and then the hybrid complex is captured onto the solid-phase surface.

In some embodiments, the DIANA is incubated with a solid surface prior to capturing the amplicon.

In some embodiments, the solid-phase surface is a bead, nanoparticle, microparticle or flat substrate. In some embodiments, the solid-phase surface is further chemically modified to facilitate binding of the DIANA to it.

In some embodiments, the detection region is the same region, e.g., in the same well, tube, or chamber, or in the same region on a fluidic cassette, where DIANA invasion/washing processes were conducted. In other embodiments, the detection region is a different same region from where DIANA invasion/washing processes were conducted.

In some embodiments, the methods described herein have a limit of detection (LOD) of between 1-100 CFU/ml. In some embodiments, the methods described herein have a LOD of between 1-50 CFU/ml. In some embodiments, the methods described herein have a LOD of between 1-10 CFU/ml. In some embodiments, the LOD is less than 1 CFU/ml.

In some embodiments, the volume of the sample affects the LOD of the method. By way of example, but not by way of limitation, an increase in the inputted sample-volume will allow for the detection of rarer microorganisms, increasing the sensitivity of the LOD measurement.

In some embodiments, all types of microorganisms have a similar LOD, whereas in other embodiments, individual LODs may vary.

In some embodiments, the limit of detection of microorganisms may not be measurable using the standard of CFU or Colony Forming Units per unit volume, as the microorganism may (1) not form colonies, or (2) may be unculture-able.

Bloodstream Infections

In some embodiments, the methods disclosed herein allowing for identification and evaluation microbial species using DIANAs are optimized for detection of bloodstream infections (BSIs). As is discussed herein, detecting microorganisms in the context of BSIs faces unique challenges because of the blood components which may hinder downstream processing, e.g., PCR, which is magnified by the large volume of blood often necessary to detect BSIs because of the low frequency of microorganisms in the blood.

The methods described herein include several innovative steps in blood processing to allow for the efficient isolation and amplification of microbial DNA, allowing for optimal detection using DIANAs. These include (i) increasing the length of extracted microbial DNA; (ii) use of ion-exchange technology; and (iii) efficient separation of human DNA from whole-blood samples. In some embodiments, the length of the extracted microbial DNA is increased relative to art known methods. Without wishing to be bound by theory, this is because high molecular weight microbial DNA (gDNA) boosts PCR sensitivity. In some embodiments, ion exchange technology is used. In some embodiments, high molecular weight gDNA is separated from low molecular weight gDNA by ion exchange. By utilizing the inherently highly-charged backbone of DNA as the exclusion criterion, ion-exchangers not only enable the separation of gDNA from non-DNA components, but likewise enable the discrimination of high molecular weight gDNA from shorter DNA fragments. In some embodiments, greater than 95%, greater than 96%, greater than 97%, greater than 98%, greater than 99%, greater than 99.5% or greater than 99.9% of human DNA is removed from whole blood. A simple, yet efficient process for removing hDNA from a whole-blood sample, without the need for centrifugation, has been developed. In combination, these processes are effective in overcoming issues of PCR inhibition when using undiluted extracts, while simultaneously reducing background amplification from low molecular weight, contaminating DNA. The entire process is effective, robust and reproducible in yielding pure, PCR-ready, gDNA directly from whole blood yet can be simple enough to be easily transitioned to automation.

Quantification of Microbial Load

In some embodiments, the methods described herein comprise monitoring microbial, e.g., pathogen, load. This is useful, for example, in the context of measuring the load of a microbe or microbes in a subject over time, to monitor the course of infection, or to observe the response of the microbe to therapeutic intervention, e.g., antibiotics or antifungals. In some embodiments, the methods described herein provide is the ability to measure microbial load quantitatively, i.e., the methods provide a direct correlation between inputted pathogen load and signal output. In some embodiments, the methods described herein provide the ability to measure microbial load semi-quantitatively.

In some embodiments, the ability to measure microbial load is useful clinically, medically, or scientifically.

In some embodiments, the microbial load is measured over time, e.g., at multiple time points, e.g., at a first and second time point. In some embodiments, measuring microbial load at a first and second time point can allow the course of infection or response to treatment to be monitored in a subject. In some embodiments, an increase in microbial, e.g., pathogen, load indicates that the subject has an infection that is worsening. In some embodiments, an increase in microbial, e.g., pathogen, load indicates that the subject has an infection that is not improving. In some embodiments, no change in microbial, e.g., pathogen, load indicates that the subject has an infection that is not resolving. In some embodiments, if the subject is receiving treatment, e.g., with an antimicrobial, an increase in the microbial, e.g., pathogen, load indicates that the microbial species is not susceptible to the antimicrobial. In some embodiments, if the subject is receiving treatment, e.g., with an antimicrobial, a decrease in the microbial, e.g., pathogen, load indicates that the microbial species is susceptible to the antimicrobial. The specific response with regards to microbial load is dependant on the compound—host— microbe relationship. In some embodiments, the second time point is at least about 1, 2, 3, 4, 5, 6, 7, 8, 9, 10, 11, or 12 hours after the first time point.

In some embodiments, measuring microbial load can be used to measure the susceptibility of microbial species to therapeutic agents, e.g., antimicrobials, ex-vivo. In some embodiments, a sample is acquired, e.g., obtained, from a subject as described herein. In some embodiments, the microbial load is measured in a sample, and the microbial load is then measured at a second time point in the same sample, after exposure to an antimicrobial.

In some embodiments, the sample can be divided into multiple samples, e.g., aliquots. In some embodiments, the sample is divided into 1, 2, 3, 4, 5, 6, or more aliquots. In some embodiments, the sample is divided into multiple aliquots and the microbial load is measured in an untreated sample. In some embodiments, the sample is divided into multiple aliquots and one or more aliquots are treated with antimicrobials, after which the microbial load is measured.

In some embodiments, the microbial load in a sample treated with an antimicrobial is measured 10 minutes, 20 minutes, 30 minutes, 40 minutes, 50 minutes, 1 hour, 1 hour 10 minutes, 1 hour 20 minutes, 1 hour 30 minutes, 2 hours, 2 hours 30 minutes, 3 hours, 4 hours, 5 hours, 6 hours, or 7 hours, after treatment with the antimicrobial.

The microbial load of a sample treated with an antimicrobial can be compared with the microbial load of the same sample pre-treatment or with a different sample from the same source pre-treatment or untreated to assess the effect of the antimicrobial on the microbial species. In some embodiments, a decrease in microbial load after exposure to the antimicrobial load indicates that the microbial species is susceptible to the antimicrobial. In some embodiments, an increase in the microbial load, or no change in the microbial load, after exposure to the antimicrobial indicates that the microbial species is not susceptible, or is resistant, to the antimicrobial.

Antimicrobials include, for example, ampicillin, amoxycillin, aureomicin, bacitracin, ceftazidime, ceftriaxone, cefotaxime, cephachlor, cephalexin, cephradine, ciprofloxacin, clavulanic acid, cloxacillin, dicloxacillan, erythromycin, flucloxacillan, gentamicin, gramicidin, methicillan, neomycin, oxacillan, penicillin, vancomycin, capsofungin, flucytosine, fluconazole, itraconazole, ketoconazole, and miconazole.

In some embodiments, the antimicrobial is an antibiotic. In some embodiments, the antibiotic may be a compound relating to the following antibiotic classes:penicillins, tetracyclines, cephalosporins, quinolones, lincomycins, macroslides, sulfomides, glycopeptides, aminoglycosides, and/or carapenems. In some embodiments, the antibiotic may be from an alternative class of antibiotics.

In some embodiments, the antimicrobial is an antifungal. In some embodiments, the antifungal may be a compound relating to the following antifungal classes from azoles, allylamines, echinocandins, nucleoside analogs, and/or polyenes. In some embodiments, the antifungal selected may be selected from an alternative class of antifungals.

In some embodiments, the amount, concentration, or number of microorganisms present in the initial sample is determined through a calibration process. This is in contrast to methods which require culturing, and other molecular methods with a non-integrated approach.

In some embodiments, the calibration process comprises one or more calibration steps. In some embodiments, calibration for quantitative or semi-quantitative load assessment for a given load input range (i.e. 1-100 CFU/ml) comprises comparing the results of a DIANA invasion assay using the methods described herein to the results of colony counts using the same input, e.g., the same input amount or a known relative input amount. In some embodiments, calibration for the quantitative or semi-quantitative load assessment for a given load input range comprises inputting predetermined quantities of cells. In some embodiments, calibration for the quantitative or semi-quantitative load assessment may be accomplished for a given load input range comprises inputting predetermined quantities of gDNA.

In some embodiments, quantitation or semi-quantitative is accurate within a particular input load dynamic range, e.g., between 1 and 100 to 3,000, between 2 and 100 to 3,000, between 3 and 100 to 3,000, between 4 and 100 to 3,000, between 5 and 100 to 3,000, between 6 and 100 to 3,000, between 7 and 100 to 3,000, between 8 and 100 to 3,000, between 9 and 100 to 3,000, between 10 and 100 to 3,000, between 11 and 100 to 3,000, between 12 and 100 to 3,000, between 13 and 100 to 3,000, between 14 and 100 to 3,000, between 15 and 100 to 3,000, between 16 and 100 to 3,000, between 17 and 100 to 3,000, between 18 and 100 to 3,000, between 19 and 100 to 3,000, between 20 and 100 to 3,000, between 21 and 100 to 3,000, between 22 and 100 to 3,000, between 23 and 100 to 3,000, between 24 and 100 to 3,000, between 25 and 100 to 3,000, between 26 and 100 to 3,000, between 27 and 100 to 3,000, between 28 and 100 to 3,000, between 29 and 100 to 3,000, or between 30 and 100 to 3,000 CFU input. In some embodiments, the output or signal dynamic range is between about 10× and 50×, between about 20× and 100×, between about 30× and 300×, between about 40× and 400×, between about 50× and 500×, between about 60× and 600×, between about 70× and 700×, between about 80× and 800×, between about 90× and 900×, between about 100× and 1000×, between about 100× and 1250×, between about 100 and 1500×, between about 100 and 1750×, or between about 100× and 2000×.

In some embodiments, the input load dynamic range is adjusted by varying the input volume and/or increasing or decreasing the output or yield of the enzymatic amplification step. By way of example, but not by way of limitation, should an input of 1-100 CFU, with a recalibrated optimal number of PCR cycles under the current conditions be 30, assuming a PCR cycle efficiency of 85%, a similar dynamic range of 100× could be achieved for an input of 250-2,500 CFU by using roughly 20-22 PCR cycles.

In some embodiments, the output or yield of the enzymatic amplification step is increased or decreased to accommodate fewer or more DIANA probes in the detection step.

In some embodiments, 1, 2, 3, 4, 5, 6, 7, 8, 9, 10, 11, 12, 13, 14, 15, 16, 17, 18, 19, or 20 DIANA probes are used in the detection step. In some embodiments, more than 20 DIANA probes are used in the detection step. In some embodiments, more than 40 DIANA probes are used in the detection step. In some embodiments, more than 80 DIANA probes are used in the detection step. In some embodiments, more than 150 DIANA probes are used in the detection step. In some embodiments, more than 500 DIANA probes are used in the detection step. In some embodiments, the processes defined here facilitate the ability to utilize 15-25 DIANA probes, as a system, while achieving a dynamic range detection of 500-1,000×.

In some embodiments, one calibration for load assessment is performed for all organisms to be tested. In some embodiments, one calibration for load assessment is performed for all Gram positive microorganisms to be tested. In some embodiments, one calibration for load assessment is performed for all Gram negative microorganisms to be tested. In some embodiments, one calibration for load assessment is performed for all fungi to be tested. In some embodiments, one calibration for load assessment is performed for each genus to be tested. In some embodiments, a calibration for quantitative load assessment is performed for each organism to be quantified.

In some embodiments, separate calibrations for quantitative or semi-quantitative load assessment are not done for different sample types. In some embodiments, separate calibrations for quantitative load assessment are done for different sample types, e.g., blood, urine, ect. In some embodiments, separate calibrations for quantitative load assessment are done for samples having compounds that may affect the readout of the assay, e.g., antibiotics, anticoagulants, drug compounds, etc.

In some embodiments, calibration for quantitative or semi-quantitative load assessment may yield a results range. By way of example, without limitation, a given input load may yield a signal of 100±9.

In some embodiments, there may be one or more mathematical relationships between load input and signal output, for example linear, polynomial, exponential, etc.

In some embodiments, more than one microbial species will be measured and calibration for load assessment will take into account one or more of the following factors: relative lysis yields, relative amplification yields, genomic copies of the target region for amplification, DIANA capture/detection efficiency. In some embodiments, none of these factors are taken into account. In some embodiments, a subset of these factors are taken into account. In some embodiments, all of these factors are taken into account. A non-limiting example would be a case where two pathogens are present in a sample, for example two Gram-negative bacterial species. Given the ease with which these bacteria are lysed, and the single primer pair used to amplify both species, it is likely that only target genomic copies and DIANA capture/detection efficiency need to be accounted for.

In some embodiments, the ability to determine change in pathogen load, may be of use in multiple applications, by way of example but not by way of limitation, during drug/compound development processes, enrichment of clinical trials, monitoring performance of a treatment in-vitro, monitoring performance of a treatment in-vivo, determining if to alter treatment or care, establishing compound-pathogen-host relationships.

Microbial Spectra

In some embodiments, the growth-bias free detection of polymicrobial infected/inoculated samples, in combination with load assessment, is defined herein as "microbial spectrum." In some embodiments, a microbial spectrum includes a semi-quantitative or quantitative assay comprising two or more DIANA probes which can differentiate among two or more microorganisms.

In some embodiments, the assay can differentiate among 2 or more, 5 or more, 10 or more, 20 or more, 50 or more, or 100 or more microorganisms, e.g., about 2, about 3, about 4, about 5, about 6, about 7, about 8, about 9, about 10, about 15, about 20, about 25, about 50, about 75, about 100, about 150, about 225, about 250, about 350, about 500, about 750, about 1,000, about 1,500, about 2,000, or about 2,500 microorganisms. In some embodiments, the assay can differentiate among 2-2,250, about 5-250, about 10-225, or about 10-750 microorganisms.

In some embodiments, the ability to assess a microbial spectrum includes the ability to assess the relative microbial load of one or more of the microorganisms in the specimen (load of microorganism 1 vs load of microorganism 2, etc).

In some embodiments, the ability to assess a microbial spectrum includes the ability to assess the absolute microbial load of one or more of the microorganisms in the specimen (load of microorganism 1 vs load of microorganism 2, etc).

In some embodiments, the ability to assess a microbial spectrum includes the ability to assess the both the relative and the absolute microbial load of one or more of the microorganisms in the specimen (load of microorganism 1 vs load of microorganism 2, etc).

In some embodiments, the ability to assess the microbial spectrum, may be of utility clinically, medically, or scientifically.

In some embodiments, the ability to determine changes or lack thereof in the microbial spectrum, as a result of treatment, non-treatment, time, drug compounds, etc. may be of utility clinically, medically, or scientifically.

In some embodiments, the ability to determine changes in microbial spectrum, may be of use in multiple applications, by way of example but not by way of limitation, during drug/compound development processes, enrichment of clinical trials, monitoring performance of a treatment in-vitro, monitoring performance of a treatment in-vivo, determining if to alter treatment or care, establishing compound-pathogen-host relationships.

Fluidic Device

In certain embodiments, the fluidic device described herein involve a unique approach to interfacing relatively large volumes (e.g., milliliters) of fluid with micro- or millimeter-scale fluidic channels. For instance, in some embodiments, a device described herein includes a series of fluidic reservoirs, which may be adapted and arranged to contain relatively large amounts (e.g., milliliters) of fluid such as reagents. Each fluidic reservoir may be connected to one or more fluidic channels. The device may also include one or more gas chambers in fluidic communication with a fluidic reservoir. The gas chambers may be used, for example, to pressurize the fluid in the reservoirs to promote fluid flow into and/or out of the fluidic channels. The fluidic channels may be connected to a fluidic hub, which may facilitate the flow of one or more fluids between two or more fluidic reservoirs. For instance, the fluidic hub may include a series of valves and/or channels that direct fluid flow to a particular reservoir for a particular operation (e.g., lysing, reaction, isolation, amplification, detection) to take place. A subsequent operation can then be performed by transporting the fluid back to the fluidic hub, via the fluidic channels, and into a different reservoir. In some cases, the fluidic hub may facilitate the transport of a gas to one or more reservoirs and, subsequently, to one or more gas chambers.

The use of a fluidic device as described herein may facilitate the transport of a fluid between two or more reservoirs, without the use of multiple pumps and/or pressure sources. For example, in some cases, a constant pressure may be applied to the fluidic device and the plurality of valves may be opened in sequence such that the fluid is transported between two or more fluidic reservoirs (e.g., without the need to adjust, change, or redirect the pressure).

Advantageously, the devices described herein may be useful for conducting particular combinations of reactions and/or steps without the need for user intervention (e.g., automatically or semi-automatically), pipetting of individual reagents, or large-scale laboratory processes (e.g., centrifugation). As compared to fluidic devices for sample detection and analysis, the devices described herein may be, in some cases, stand-alone (e.g., do not require dedicated instrumentation).

In some embodiments, the fluidic device comprises a fluidic hub and a plurality of fluidic reservoirs. In some embodiments, the fluidic device comprises a plurality of fluidic hubs and a plurality of fluidic reservoirs. In certain embodiments, each fluidic reservoir is connected to a branching channel branching from the fluidic hub. For example, as illustrated in FIG. 1, fluidic device 100 comprises a fluidic hub 110 and a fluidic reservoir 120 connected to a branching channel 125 branching from, and in fluidic communication with, fluidic hub 110. In certain embodiments, a valve 122 may be positioned between branching channel 125 and fluidic hub 110. In alternative embodiments, however, no valve may be present between a branching channel and the fluidic hub.

In some cases, fluidic device 100 comprises fluidic reservoir 115 (e.g., a sample inlet reservoir) in fluidic communication with fluidic hub 110 via branching channel 105. In some such embodiments, a fluid may be introduced into the sample inlet reservoir and transported, via the fluidic hub, to a fluidic reservoir. For example, the fluid may be introduced to fluidic reservoir 115 and transported to the fluidic hub and subsequently, via opening of valve 122, to branching channel 125 and to fluidic reservoir 120. In some embodiments, a particular operation (e.g., lysing, reaction, isolation, amplification, detection) may be conducted in fluidic reservoir 120.

Figure 2:
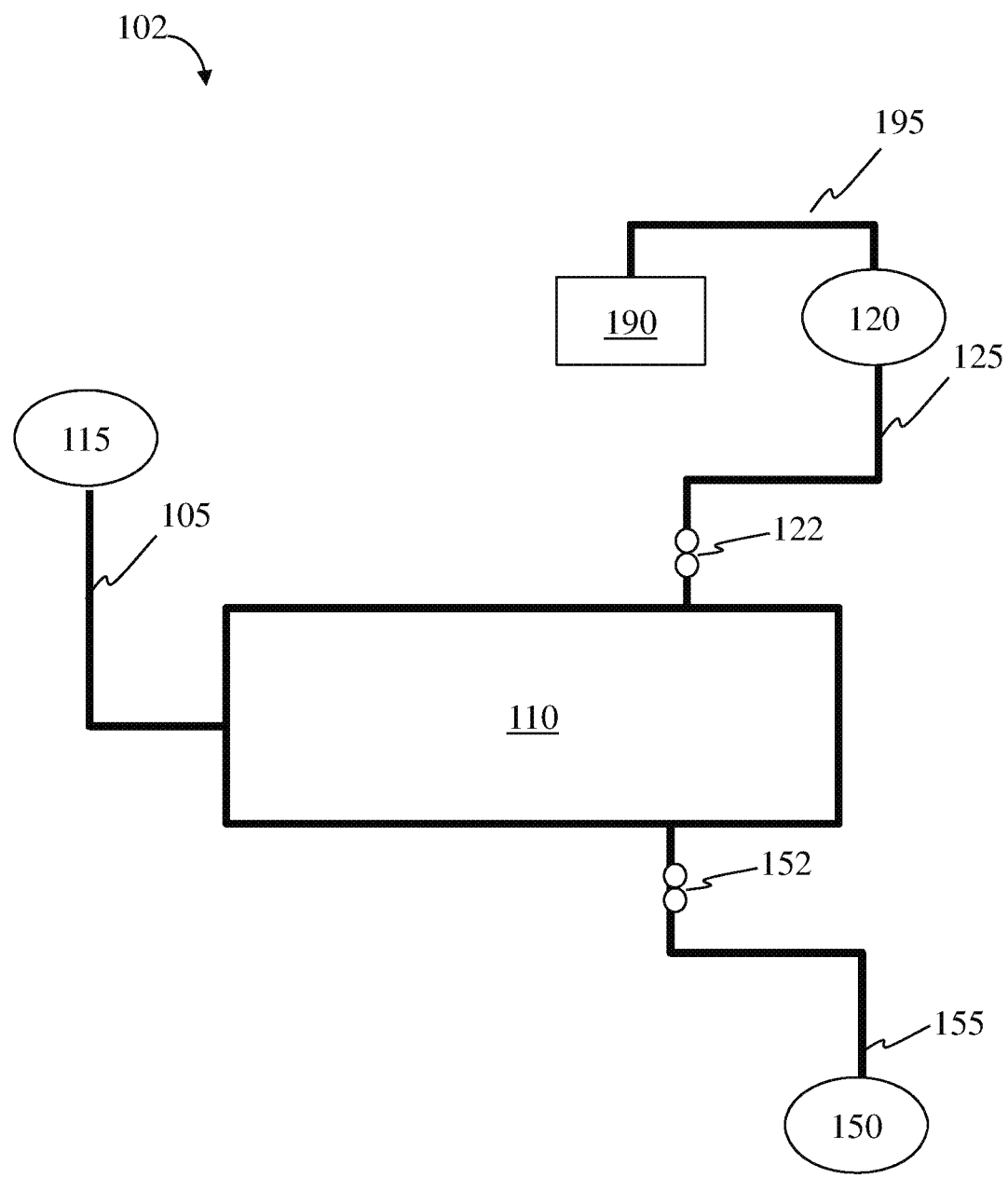
FIG. 2 is a schematic illustration of a fluidic device, according to one set of embodiments.

In some embodiments, a gas chamber may be in fluidic communication with the fluidic reservoir. For example, as illustrated in FIG. 2, fluidic device 102 comprises fluidic reservoir 120 in fluidic communication with a gas chamber 190. In some embodiments, a fluidic conduit (e.g., a fluidic channel) 195 facilitates the fluidic communication between gas chamber 190 and fluidic reservoir 120. In some embodiments, a gas may be flowed from gas chamber 190 to fluidic reservoir 120. In other embodiments, the gas may be flowed from fluidic reservoir 120 to gas chamber 190. In an exemplary embodiment, a gas may be introduced into fluidic hub 110 and transported to branching channel 125 via opening of valve 122, and subsequently transported to fluidic reservoir 120. In some such embodiments, the gas may then be transported from fluidic reservoir 120 to gas chamber 190. As described in more detail below, introducing a gas into the fluidic reservoir may aid in mixing of reagents in the fluidic reservoir.

Figure 3:
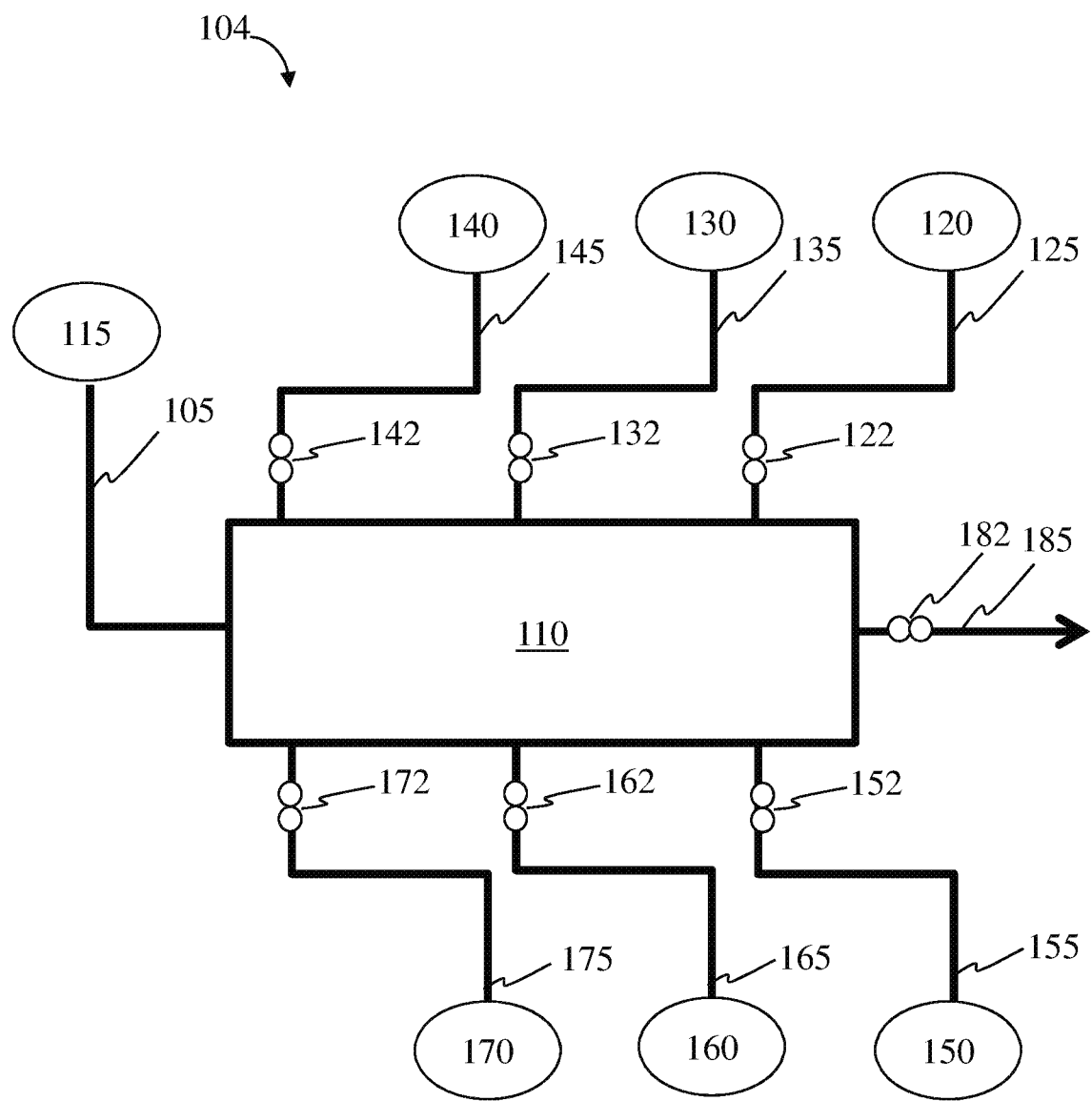
FIG. 3 is a schematic illustration of a fluidic device, according to one set of embodiments.

In certain embodiments, the fluidic device comprises a plurality of fluidic reservoirs and a plurality of branching channels branching from the fluidic hub. In some such embodiments, each fluidic reservoir may be in fluidic communication with the fluidic hub. In some embodiments, a branching channel may be in direct fluidic communication with the fluidic hub. In certain embodiments, one or more valves may be positioned between each branching channel and the fluidic hub. In an exemplary embodiment, as illustrated in FIG. 3, fluidic device 104 comprises a plurality of fluidic reservoirs including fluidic reservoir 115 (e.g., a sample inlet reservoir), fluidic reservoir 120, fluidic reservoir 130, fluidic reservoir 140, fluidic reservoir 150, fluidic reservoir 160, and fluidic reservoir 170. Each fluidic reservoir may be connected to fluidic hub 110 via branching channels 105, 125, 135, 145, 155, 165, and 175, respectively. In some cases, one or more fluidic reservoirs may contain a fluid (e.g., a reactant, a buffer). In certain embodiments, one or more fluidic reservoirs may be utilized for conducting a particular operation (e.g., lysing, isolation, amplification, and/or reacting). In some cases, a valve (e.g., valve 122, valve 132, valve 142, valve 152, valve 162, valve 172) may be positioned between a branching channel and the fluidic hub. In an exemplary embodiment, a fluid may be introduced into fluidic reservoir 115 and transported to fluidic hub 110 (via branching channel 105). In such embodiments, valve 122 may be opened (and several or all other valves closed) such that the fluid is transported from fluidic hub 110 to fluidic reservoir 120 (via branching channel 125). In certain embodiments, valve 132 may then be opened such that the fluid is transported from fluidic reservoir 120 (via branching channel 125) to fluidic hub 110 and into fluidic reservoir 130 (via branching channel 135).

The fluidic device may comprise any suitable number of branching channels. For example, in certain embodiments, the fluidic device comprises at least 2, at least 4, at least 5, at least 10, at least 20, at least 30, or at least 40 branching channels, each channel branching (e.g., extending) from the fluidic hub. In some embodiments, the fluidic device comprises less than or equal to 50, less than or equal to 40, less than or equal to 30, less than or equal to 20, less than or equal to 10, less than or equal to 5, or less than or equal to 4 branching channels, each channel branching from the fluidic hub. Combinations of the above-referenced ranges are also possible (e.g., at least 2 and less than or equal to 50). Other ranges are also possible.

In certain embodiments, the fluidic device comprises a plurality of fluidic reservoirs, each reservoir connected to a branching channel in fluidic communication with the fluidic hub. For example, in certain embodiments, the fluidic device comprises at least 2, at least 4, at least 5, at least 10, at least 20, at least 30, or at least 40 fluidic reservoirs, each reservoir in fluidic communication (e.g., connected to) a branching channel. In some embodiments, the fluidic device comprises less than or equal to 50, less than or equal to 40, less than or equal to 30, less than or equal to 20, less than or equal to 10, less than or equal to 5, or less than or equal to 4 fluidic reservoirs, each reservoir in fluidic communication (e.g., connected to) a branching channel. Combinations of the above-referenced ranges are also possible (e.g., at least 2 and less than or equal to 50). Other ranges are also possible.

In some cases, the fluidic device may comprise one or more additional chambers and/or regions in fluidic communication with the fluidic hub. For example, referring again to FIG. 3, in some embodiments (e.g., after conducting a series of operations in the plurality of fluidic reservoirs), a fluid may be transported from fluidic hub 110 to fluidic channel 185 (e.g., via opening of valve 182). Fluidic channel 185 may be in fluidic communication with, for example, one or more processing chambers and/or one or more detection regions, as described in more detail below.

In some cases, the gas chamber may be open to atmosphere (e.g., for venting of a gas). In certain embodiments, the gas chamber may be in fluidic communication with a pressure source, such that a pressure can be applied to a second fluid (e.g., a gas) within the gas chamber such that the second fluid pushes a first fluid contained within a fluidic reservoir in fluidic communication with the gas chamber.

As described above, in some embodiments, the fluidic device comprises a gas chamber in fluidic communication with a fluidic reservoir. In some embodiments, the gas chamber may have a particular volume. In certain embodiments, the gas chamber has a volume of at least 0.1 mL, at least 0.2 mL, at least 0.5 mL, at least 1 mL, at least 2 mL, or at least 5 mL. In certain embodiments, the gas chamber have a volume of less than or equal to 10 mL, less than or equal to 5 mL, less than or equal to 2 mL, less than or equal to 1 mL, less than or equal to 0.5 mL, or less than or equal to 0.2 mL. Combinations of the above referenced ranges are also possible (e.g., at least 0.1 mL and less than or equal to 10 mL). Other ranges are also possible.

As described above, in some embodiments, a fluid may be transported between the fluidic hub and one or more fluidic reservoirs. In some embodiments, the fluid may be reacted with a reagent present in the fluidic reservoir to form a reacted fluid in the fluidic reservoir. In some such embodiments, a pressure may be applied to the reacted fluid such that the reacted fluid flows into the fluidic hub. For example, in some embodiments, a pressure may be applied to a gas chamber in fluidic communication with the fluidic reservoirs such that the reacted fluid flows into the fluidic hub. In certain embodiments, the fluid may then be transported (e.g., by continuing to apply pressure) to one or more additional branching channels. For example, as illustrated in FIG. 2, a fluid may be flowed from fluidic hub 110 into fluidic reservoir 120 (via branching channel 125 upon opening of valve 122) and reacted with a reagent to form a reacted fluid. In some embodiments, a pressure may be applied to the reacted fluid via gas chamber 190 such that the reacted fluid flows from fluidic reservoir 120 and into fluidic hub 110. Upon opening of valve 152, the reacted fluid may flow from fluidic hub 110 and into branching channel 155. In some embodiments, the fluid may undergo a series of additional reactions and/or operations by flowing between one or more additional fluidic reservoirs. In an exemplary embodiment, the reacted fluid may be flowed from the second fluidic reservoir into the fluidic hub and subsequently flowed into a third fluidic reservoir (e.g., for reacting with one or more additional reagents).

In some embodiments, a constant differential pressure is applied to the various components (e.g., gas chambers, fluidic reservoirs, fluidic hub, and/or fluids contained therein) of the fluidic device. In certain embodiments, the opening and/or closing of one or more valves facilitates the flow of a fluid between one or more fluidic reservoirs and the fluidic hub. In some cases, the different pressure prohibits flow between one or more fluidic reservoirs. In some embodiments, the constant differential pressure is a positive pressure. In certain embodiments, the constant differential pressure is a negative pressure. In some cases, the constant differential pressure may be at least 0.1 psig, at least 0.2 psig, at least 0.3 psig, at least 0.5 psig, at least 0.8 psig, at least 1 psig, at least 2 psig, at least 5 psig, at least 10 psig, or at least 15 psig. In certain embodiments, the constant different pressure is less than or equal to 20 psig, less than or equal to psig, less than or equal to 10 psig, less than or equal to 5 psig, 2 psig, less than or equal to 1 psig, less than or equal to 0.8 psig, less than or equal to 0.5 psig, less than or equal to 0.3 psig, or less than or equal to 0.2 psig. Combinations of the above-referenced ranges are also possible (e.g., at least 0.1 psig and less than or equal to 20 psig). Other ranges are also possible.

In some embodiments, a first fluid (e.g., a liquid) may be transported by pushing (i.e., displacing) the first fluid with a second fluid, immiscible with the first fluid. In certain embodiments, the second fluid is a gas. For example, in some embodiments, a fluidic reservoir may comprise the first fluid (e.g., a stored reagent) and a second fluid may be introduced into the fluidic reservoir, displacing the first fluid from the fluidic reservoir (e.g, into the fluidic hub via a branching channel). In certain embodiments, a fluidic channel (e.g., a branching channel) may comprise the first fluid and the second fluid may be introduced into the fluidic channel, displacing the first fluid from the branching channel (e.g., into a fluidic reservoir, into the fluidic hub). In some embodiments, a constant differential pressure may be applied to the second fluid such that the second fluid contacts and pushes the first fluid.

In an exemplary embodiment, a first fluid may be introduced into a first branching channel, and a second fluid in the first branching channel, while the first branching channel is in in fluidic communication with the fluidic hub. Referring again to FIG. 2, in some embodiments, branching channel 125 may be in fluidic communication with fluidic hub 110 (e.g., via opening of valve 122) and branching channel 155 may not be in fluidic communication with the fluidic hub (e.g., via closing of valve 152). In some such embodiments, a fluid present in branching channel 125 may be pushed by a second fluid introduced into branching channel 125 (e.g., from gas chamber 190 via fluidic conduit 195), and the fluid is pushed into fluidic hub 110. In some embodiments, the second fluid enters the fluidic hub.

In some embodiments, the first fluid (e.g. the first fluid pushed by the second fluid) may have a particular volume. For example, in some embodiments, the first fluid has a volume of at least 0.1 mL, at least 0.2 mL, at least 0.5 mL, at least 1 mL, at least 2 mL, or at least 5 mL. In certain embodiments, the first fluid may have a volume of less than or equal to 10 mL, less than or equal to 5 mL, less than or equal to 2 mL, less than or equal to 1 mL, less than or equal to 0.5 mL, or less than or equal to 0.2 mL. Combinations of the above referenced ranges are also possible (e.g., at least 0.1 mL and less than or equal to 10 mL). Other ranges are also possible.

In some embodiments, the second fluid is immiscible with the first fluid. In certain embodiments, the second fluid comprises a gas (e.g., a sterilized gas). In certain traditional fluidic (e.g., microfluidic) devices it is generally undesirable to flow gases in the system since they can introduce air bubbles that can inhibit flow of liquids. Advantageously, the use of gases in the fluidic devices described herein may be useful for facilitating the flow of one or more fluids within the system and/or to promote mixing of fluids as described in more detail herein.

As described above, in some embodiments, the fluidic device comprises at least one fluidic channel in fluidic communication with a fluidic reservoir. A fluidic channel described herein (e.g., a branching channel, a hub channel) can have a particular average cross-sectional dimension. The "cross-sectional dimension" (e.g., a diameter, a width) of the channel is measured perpendicular to the direction of fluid flow. In some embodiments, the average cross-sectional dimension of the at least one channel is less than or equal to about 3 mm, less than or equal to about 2 mm, less than or equal to about 1 mm, less than or equal to about 800 microns, less than or equal to about 600 microns, less than or equal to about 500 microns, less than or equal to about 400 microns, less than or equal to about 300 microns, less than or equal to about 200 microns, less than or equal to about 175 microns, less than or equal to about 150 microns, or less than or equal to about 125 microns. In certain embodiments, the average cross-sectional dimension of the at least one channel is greater than or equal to about 100 microns, greater than or equal to about 125 microns, greater than or equal to about 150 microns, greater than or equal to about 175 microns, greater than or equal to about 200 microns, greater than or equal to about 250 microns, greater than or equal to about 300 microns, greater than or equal to about 400 microns, greater than or equal to about 500 microns, greater than or equal to about 600 microns, greater than or equal to about 800 microns, greater than or equal to about 1 mm, or greater than or equal to about 2 mm. Combinations of the above-referenced ranges are also possible (e.g., between about 250 microns and about 2 mm, between about 400 microns and about 1 mm, between about 300 microns and about 600 microns). Other ranges are also possible. The dimensions of the channel may also be chosen, for example, to allow a certain volumetric or linear flowrate of fluid in the channel and/or to hold a certain volume of fluid in the channel. Of course, the number of channels and the shape of the channels can be varied by any method known to those of ordinary skill in the art. The fluidic channel can have any cross-sectional shape (circular, oval, triangular, irregular, trapezoidal, square or rectangular, or the like).

One or more fluidic channels may also have a channel length-to-width ratio (length to average cross sectional dimension) of at least 5:1, at least 6:1, at least 8:1, at least 10:1, at least 20:1, at least 50:1, or at least 100:1.

A fluidic channel can have any suitable volume. In some embodiments, the volume of a fluidic channel (e.g., a branching channel, a hub channel) may be at least 0.1 microliters, at least 0.5 microliters, at least 1 microliter, at least 2 microliters, at least 5 microliters, at least 10 microliters, at least 25 microliters, at least 50 microliters, at least 100 microliters, at least 200 microliters, at least 500 microliters, or at least 1000 microliters. In certain embodiments, the volume of one or more fluidic channels may be less than or equal to 2000 microliters, less than or equal to 1000 microliters, less than or equal to 500 microliters, less than or equal to 200 microliters, less than or equal to 100 microliters, less than or equal to 50 microliters, less than or equal to 25 microliters, less than or equal to 10 microliters, less than or equal to 5 microliters, less than or equal to 2 microliters, less than or equal to 1 microliter, or less than or equal to 0.5 microliters. Combinations of the above referenced ranges are also possible (e.g., at least 0.1 microliters and less than or equal to 2000 microliters, at least 0.1 microliters and less than or equal to 1000 microliters). Other ranges are also possible.

A fluidic channel (e.g., a branching channel, a hub channel) may also have any suitable length. In some embodiments, one or more fluidic channels have a length of at least 1 cm, at least 2 cm, at least 5 cm, at least 10 cm, or at least 20 cm. In certain embodiments, one or more fluidic channels may have a length of less than or equal to 30 cm, less than or equal to 10 cm, less than or equal to 5 cm, or less than or equal to 2 cm. Combinations of the above-referenced ranges are possible (e.g., at least 1 cm and less than or equal to 30 cm). Other ranges are also possible.

Figure 4:
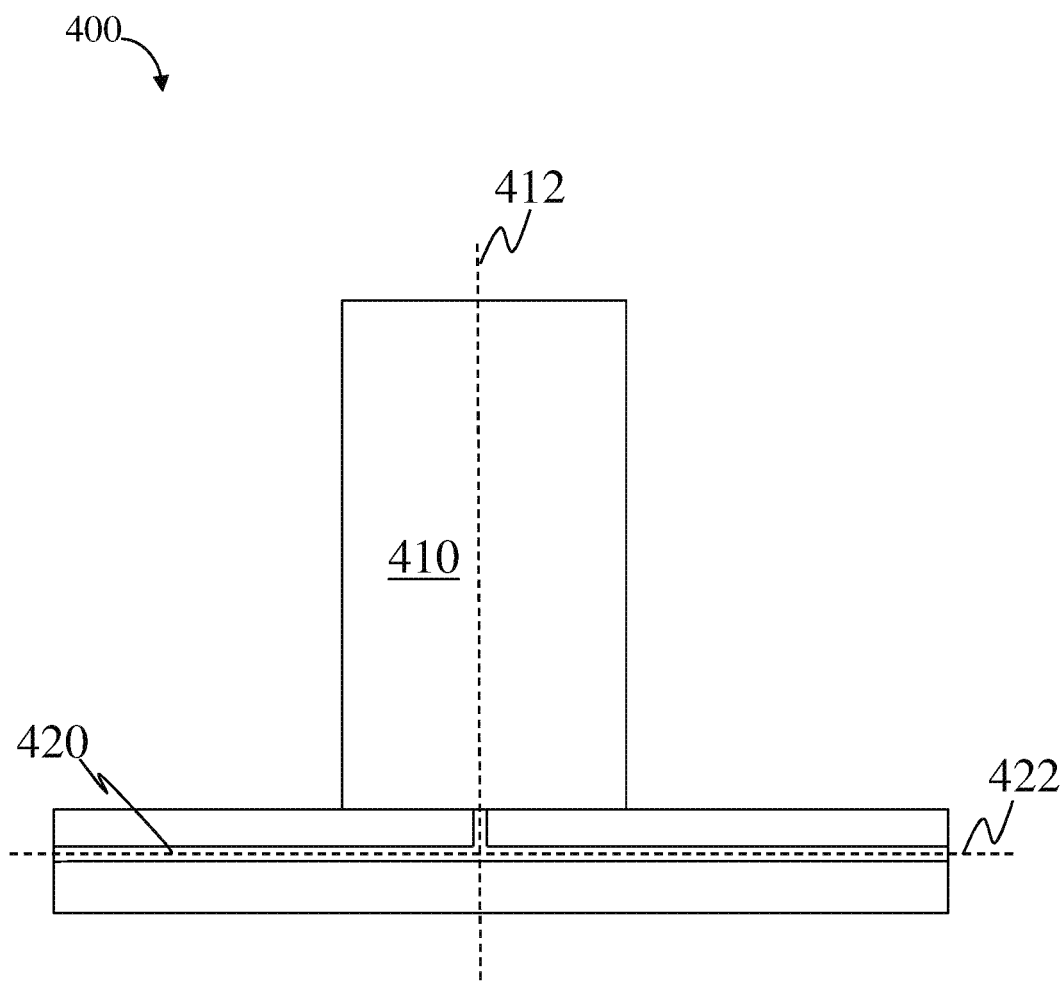
FIG. 4 is a schematic illustration of a fluidic device, according to one set of embodiments.

In some embodiments, a longitudinal axis of at least one fluidic channel is substantially perpendicular to a longitudinal axis (e.g., height) of at least one fluidic reservoir. For example, as illustrated in FIG. 4, fluidic device 400 comprises fluidic reservoir 410 and fluidic channel 420.

In some embodiments, longitudinal axis 412 of fluidic reservoir 412 is substantially perpendicular to longitudinal axis 422 of fluidic channel 420. As shown illustratively in this figure, the longitudinal axis 412 of fluidic reservoir 412 lies on a different plane than longitudinal axis 422 of fluidic channel 420. By extending the longitudinal axis (e.g., height) of the reservoir, this configuration may allow the fluidic reservoir to hold a greater amount of volume compared to a configuration in which the longitudinal axes of the fluidic reservoir and the fluidic channel (connected to the fluidic reservoir) are on the same plane or are parallel to one another.

In some embodiments, at least one fluidic channel described above is a branching channel. In certain embodiments, the fluidic hub is a fluidic channel, as described herein (e.g., having a length of at least 1 cm).

In some embodiments, each fluidic reservoir may have a particular volume. For example, in some embodiments, each fluidic reservoir may have a volume of at least 0.1 mL, at least 0.2 mL, at least 0.5 mL, at least 1 mL, at least 2 mL, at least 5 mL, at least 10 mL, at least 25 mL, or at least 50 mL. In certain embodiments, each fluidic reservoir may have a volume of less than or equal to 100 mL, less than or equal to 50 mL, less than or equal to 25 mL, less than or equal to 10 mL, less than or equal to 5 mL, less than or equal to 2 mL, less than or equal to 1 mL, less than or equal to 0.5 mL, or less than or equal to 0.2 mL. Combinations of the above referenced ranges are also possible (e.g., at least 0.1 mL and less than or equal to 100 mL). Other ranges are also possible.

In some embodiments, a fluidic reservoir may be a storage reservoir (e.g., for storing one or more reagents for conducting a particular operation). The reagent may be stored and sealed in the fluidic reservoir, e.g., prior to use of the fluidic device by the user and/or prior to insertion of a sample into the device. In some embodiments, one or more reagents contained within a fluidic reservoir may be a liquid reagent (e.g., a wash buffer, a lysis reagent, an isolation reagent). In certain embodiments, one or more reagents contained within a fluidic reservoir may be a dry, lyophilized, and/or pelleted reagent. In some such embodiments, the stored reagent may be suspended (e.g., upon introduction of a fluid into the fluidic reservoir containing the stored reagent).

In some cases, a fluidic reservoir may define a region for conducting a particular operation. In some embodiments, a fluidic reservoir may be reused and define a region for conducting more than one operation. In some cases, one or more operations may be conducted in parallel (e.g., in one or more fluidic reservoirs).

In some cases, a fluidic reservoir may be reused for two or more operations. In certain embodiments, a first fluidic reservoir may be used for a first reaction and, after the fluid has been flowed to one or more additional fluidic reservoirs, the fluid may be flowed again to the first fluidic reservoir for conducting a second reaction, the same or different than the first reaction. In an exemplary embodiment, a first operation such as lysing may be conducted in the first fluidic reservoir, and after the fluid has been flowed to one or more additional fluidic reservoirs (e.g., for conducting one or more particular operations), the fluid may be flowed to the first fluidic reservoir for a second operation such as mixing. Those skilled in the art would understand that using the fluidic reservoir for lysing and mixing operations are by way of example only, and that one or more operations described herein may be conducted in the same or different reservoirs. In some cases, the fluidic reservoir may be reused as a waste reservoir (e.g., for storing waste fluids remaining after a particular operation conducted in a different reservoir). Advantageously, the ability to reuse one or more fluidic reservoirs as a waste reservoir may, for example, reduce the size and cost of the fluidic device as compared to other fluidic devices for sample detection and analysis, and/or may remove the need to removal of waste products and/or fluids during operation of the fluidic device.

It should be appreciated although detection is primarily described herein, in some embodiments, the fluidic devices and methods described herein may be used for monitoring various processes, events or conditions such as microbial load. For example, a device or method may be used for monitoring changes in microbial loads from samples originating from multiple sources (e.g., bodily locations) and/or for monitoring changes in microbial load over time and/or in response to an applied treatment. The fluidic devices and methods described herein may be used for determining quantitative effects of microbial load (e.g., as well as qualitative ones) in some embodiments. Monitoring may occur in a single detection event, periodically or continuously.

In certain embodiments, one or more fluidic reservoirs and/or one or more fluidic channels may be heated. In some embodiments, the fluidic reservoirs and/or one or more fluidic channels may be heated by one or more heating elements proximate the fluidic reservoir including, for example, resistance heaters, thermo-electric heaters, optical heaters, or the like. In some embodiments, one or more fluidic reservoirs (or one or more fluids contained and/or stored therein) may be heated to a particular temperature (e.g., for a given operation such as lysing, isolation, amplification, detection). For example, in certain embodiments, one or more fluidic reservoirs and/or one or more fluidic channels may be heated to at least 5° C., at least 10° C., at least 15° C., at least 20° C., at least 25° C., at least 30° C., at least 35° C., at least 37° C., at least 40° C., at least 50° C., at least 60° C., at least 70° C., at least 75° C., at least 80° C., at least 85° C., at least 90° C., at least 95° C., at least 100° C., or at least 110° C. In certain embodiments, one or more fluidic reservoirs and/or one or more fluidic channels may be heated to a temperature of less than or equal to 120° C., less than or equal to 110° C., less than or equal to 100° C., less than or equal to 95° C., less than or equal to 90° C., less than or equal to 85° C., less than or equal to 80° C., less than or equal to 75° C., less than or equal to 70° C., less than or equal to 60° C., less than or equal to 50° C., less than or equal to 40° C., less than or equal to 37° C., less than or equal to 35° C., less than or equal to 30° C., less than or equal to 25° C., less than or equal to 20° C., less than or equal to 15° C., or less than or equal to 10° C. Combinations of the above-referenced ranges are possible (e.g., at least 5° C. and less than or equal to 100° C.). Other ranges are also possible. In some cases, the temperature may be cycled (e.g., during an amplification operation). For example, in some embodiments, the temperature may be cycled between 50° C. and 120° C., or between 70° C. and 120° C. or between about 25° C. and 75° C.

In some embodiments, a valve may be positioned between a branching channel and the fluidic hub. For example, referring again to FIG. 1, in certain embodiments, a valve 122 may be positioned between branching channel 125 and fluidic hub 110. In some embodiments, the valve is a flow-gate. In certain embodiments, the valve may be a membrane-based valve. For example, a piston may be disposed on the membrane-based valve such that the valve is closed. In certain embodiments, the piston may be raised such that the valve is opened. Other flow-restricting valves are also possible including, but not limited to, miniature solenoids, manifolds, deformable gels, and/or membranes to control the passage or flow of fluid from the fluidic hub to one or more branching channels. In some embodiments, the fluidic devices and/or methods described herein may comprise one or more valves (e.g., flow-gates) described in U.S. Pat. No. 9,132,426, issued Sep. 15, 2015, and entitled "Simplified gating method for sealing and flow control in micro and nano devices", which is incorporated herein by reference in its entirety for all purposes. Other valves are also possible.

In some cases, the fluidic conduit positioned between a gas chamber and a fluidic reservoir comprises a valve (e.g., a flow-gate).

In some embodiments, the fluidic device comprises one or more lysis regions. In some embodiments, one or more lysis regions are in fluidic communication with a fluidic channel (e.g., a fluidic hub). In certain embodiments, one or more lysis regions are in fluidic communication with an isolation region, as described herein. In some cases, one or more lysis regions may be in fluidic communication with one or more additional regions comprising one or more fluidic reservoirs described herein. In some embodiments, one or more lysis regions may be in fluidic communication with the fluidic hub. In certain embodiments, the lysing operation comprises chemical lysing, including, for example, exposing a patient's sample to a chemical lysing reagent that results in the opening or rupturing of a cell membrane of the select eukaryotic cell. In certain embodiments, the fluidic reservoir contains one or more lysing reagents (e.g., stored lysing reagents) prior to the flow of the sample to the fluidic reservoir. In other embodiments, one or more lysing reagents may be added to the fluidic reservoir after the flow of the sample to the fluidic reservoir. Referring again to FIG. 3, in an exemplary embodiment, fluidic device 104 comprises a first lysis region comprising fluidic reservoir 120 for conducting a first lysing operation and a second lysis region comprising fluidic reservoir 130 for conducting a second lysing operation. In some embodiments, the first lysis region comprises one or more stored lysing reagents. In certain embodiments, the second lysis region comprises one or more stored lysing reagents, which may be the same or different from the lysing reagents in the first lysis region. In some cases, the fluid (e.g., the sample) may be flowed to the first lysis region and one or more lysing reagents may be added to the first lysis region (e.g., a lysing reagent(s) flowed from one or more additional fluidic reservoirs including the lysing reagent(s)). In some cases, the fluid (e.g., the sample) may be flowed to the second lysis region and one or more lysing reagents may be added to the second lysis region (e.g., lysing reagent(s) flowed from one or more additional fluidic reservoirs including the lysing reagent(s)).

In some embodiments, one or more lysing operations comprises the lysing of select eukaryote cells (e.g., select eukaryote cells present in a patient's sample). In some embodiments, the lysing operation releases mammalian DNA from the sample (e.g., such that it may be isolated and/or removed from the sample). In certain embodiments released select eukaryote DNA may be isolated and/or removed from the sample after lysing thus depleting the select eukaryote genomic material from the sample.

In some embodiments, the lysing operation comprises the lysing of one or more microbial cells. In some embodiments, the lysing operation releases microbial genomic material from the microbial cells into the fluid (e.g., such that it may be isolated, amplified, and/or detected). In some cases, lysing of one or more microbial cells occurs after the lysing of select eukaryote cells. In some such embodiments, prior to lysing of one or more microbial cells, the sample has been substantially depleted of select eukaryote DNA. In alternative embodiments, lysing of one or more microbial cells is conducted without the lysing of select eukaryote cells. In certain embodiments, after lysing of select eukaryote cells, but prior to lysing of the microbial cells, at least a portion of the microbial cells may be intact (e.g., unlysed).

Lysing solutions, lysing reagents and lysing conditions are as described herein.

In some embodiments, the fluidic device comprises one or more isolation regions. In certain embodiments, one or more isolation regions are in fluidic communication with one or more lysis regions. In some embodiments, one or more isolation regions may be in fluidic communication with the fluidic hub. In some cases, one or more isolation regions may be in fluidic communication with one or more additional regions comprising one or more fluidic reservoirs described herein. In certain embodiments, after one or more lysing operations, lysed genomic material (e.g., select eukaryotic genomic material, microbial genomic material) may be isolated and/or separated from the fluid. In some cases, the genomic material is isolated by binding with a support substrate and separating the support substrate and genomic material from the fluid. Referring again to FIG. 3, in an exemplary embodiment, after the first lysing operation is performed, the fluid (e.g., containing the lysed material) is flowed to a first isolation region comprising fluidic reservoir 140 for conducting a first isolation operation (e.g., to remove/deplete select eukaryote genomic material from the fluid). In some such embodiments, the fluid (e.g., substantially depleted of select eukaryote genomic material) may then be transported to fluidic reservoir 130 for a second lysis operation. After the second lysing operation is performed, the fluid may be flowed to a second isolation region comprising fluidic reservoir 150 for conducting a second isolation operation (e.g., to remove/deplete select eukaryote genomic material from the fluid, to isolate microbial genomic material from the fluid). Those skilled in the art would understand, based upon the teachings of this specification, that two or more, three or more, four or more, or five or more lysing operations may be performed (e.g., in two or more fluidic reservoirs) prior to an isolation operation.

The microbial genetic material may be isolated via anion exchange within the fluidic device using the methods described herein. A support substrate may be added to, or contained within, one or more fluidic reservoirs (e.g., within one or more isolation regions) for performing an isolation operation. In certain embodiments, the genomic material (e.g., lysed genomic material) binds to at least a portion of a support substrate. The genomic material may attach or bind to a support substrate in any suitable manner.

In some embodiments, at least one anion exchanger bound to the support substrate, is contacted and/or incubated with the fluid (e.g., the lysed fluid). In some embodiments, after contacting and/or incubation with the fluid, the anion exchanger is removed from the fluid. In another embodiment, after contacting and/or incubation with the fluid, the anion exchanger is immobilized and the fluid is removed.

Genomic material may be isolated from a fluid by, for example, applying a magnetic field to a fluidic reservoir containing the genomic material bound to the support substrate, such that the support substrate is attracted to the magnetic field source, and the fluid can be removed (e.g., flowed) out of the fluidic reservoir. The removed fluid can be flowed to, for example, a waste fluidic reservoir.

In certain embodiments, during and/or after the isolation operation, the isolated genomic material may be eluted. For example, in some embodiments, competition of the isolation process is facilitated by eluting or removing the genomic material off of the anion-exchanger and/or support substrates. In some embodiments, the elution of the genomic material comprises adding an elution buffer (e.g., stored within a fluidic reservoir in fluidic communication with the fluidic hub, and transported to the isolation region). In certain embodiments, during and/or after the isolation operation, the isolated genomic material bound to the anion exchanger may be washed prior to elution.

In some embodiments, the fluidic device comprises an amplification region. In certain embodiments, the amplification region is in fluidic communication with at least one reaction region. In some cases, the amplification region may be in fluidic communication with one or more additional regions comprising one or more fluidic reservoirs described herein. In some embodiments, the amplification region is in fluidic communication with the fluidic hub. In certain embodiments, after one or more lysing and/or isolation operations, microbial genomic material may be amplified. Referring again to FIG. 3, in an exemplary embodiment, fluidic device 104 may comprise an amplification region comprising fluidic reservoir 170. In some such embodiments, fluidic reservoir 170 may comprise one or more reagents for amplification of genomic material. In certain embodiments, one or more reagents (e.g., stored in one or more additional fluidic reservoirs) may be flowed to fluidic reservoir 170 to perform the amplification operation. In some embodiments, the genomic material amplified is RNA or DNA. In some embodiments, the DNA is single stranded DNA (ssDNA) and/or double stranded DNA (dDNA). In some embodiments, the DNA is ribosomal DNA (rDNA).

In some embodiments, the amplicon generated during the amplification operation may be diluted. In certain embodiments, an invasion buffer may be added to the fluid comprising the amplicon generated during the amplification operation. For example, in certain embodiments, referring again to FIG. 3, fluidic reservoir 170 may comprise the product of an amplification operation and an invasion buffer (e.g., an invasion buffer stored in one or more additional fluidic reservoirs) may be flowed into fluidic reservoir 170. Invasion buffers are described in more detail, below.

In some embodiments, the fluidic device comprises one or more reaction regions (e.g., comprising one or more fluidic reservoirs). In certain embodiments, one or more reaction regions are in fluidic communication with one or more isolation regions. In some cases, one or more lysis regions may be in fluidic communication with one or more additional regions comprising one or more fluidic reservoirs described herein. In some embodiments, one or more reaction regions may be in fluidic communication with the fluidic hub. In some embodiments, the reaction region comprises a washing operation. Referring again to FIG. 3, in an exemplary embodiment, fluidic reservoir 160 may comprise a washing region for conducting a washing operation. In some embodiments, the washing region comprises one or more wash buffers. The wash buffers may be stored and sealed in the fluidic reservoir, e.g., prior to use of the fluidic device by the user and/or prior to insertion of a sample into the device. In some cases, the fluid (e.g., the sample) may be flowed to the washing region and one or more wash buffers may be added to the washing region (e.g., a wash buffer(s) flowed from one or more additional fluidic reservoirs storing the wash buffer(s)). In certain embodiments, a fluidic reservoir comprises of an isolation region and a washing region. That is to say, in some embodiments, a fluid (e.g., a sample) may be present in a fluidic reservoir in which a particular operation has been performed (e.g., lysing, isolation) and a wash buffer may be added to the fluidic reservoir (e.g., a wash buffer(s) flowed from one or more additional fluidic reservoirs) to wash any unbound components and/or waste reagents.

In some embodiments, after binding the microbial genomic material to the anion-exchanger bound to the support substrate, the support substrates are washed using a wash buffer. In some such embodiments, and prior to the washing operation, the anion exchanger bound to microbial genomic material is immobilized such that and unbound material can be removed without the substantial loss of microbial genomic material.

In some embodiments, one or more reaction regions comprises neutralization (e.g., with a base or an acid) of the fluid. For example, in some embodiments, an acid may be added to the fluid in one or more fluidic reservoirs to alter the pH of the fluid. Acids and bases may be stored in one or more reservoirs as described herein.

In certain embodiments, one or more reaction regions comprises or contains stored duplex DNA Invading Artificial Nucleic Acids (DIANAs) (e.g., for detection of one or more microbial pathogens.)

In some embodiments, one or more fluids contained within a fluidic reservoir may be mixed. In certain embodiments, mixing comprises agitation such as mechanical agitation (e.g., ultrasonic agitation).

In some embodiments, the devices and methods described herein may facilitate the mixing of two or more fluids (e.g., a sample and a reagent) without the use of a mixing component (e.g., propeller, etc.). In some cases, mixing may be performed by flowing a stream of gas (e.g., a sterilized gas) into a fluidic reservoir before, during, and/or after a particular operation. The stream of gas may be flowed for any suitable time (e.g., at least 1 s, 3s, 5s, 7s, 10s, 15s, 20s, 30s, 45s, 60s; and/or less than 120s, 60s). In some such embodiments, the stream of gas need not be continuous, but can be pulsed. In some such embodiments, the stream of gas may cause mixing and/or homogenization of the one or more fluids and/or reagents within a fluidic reservoir. The gas may be flowed from, for example, the fluidic hub into the fluidic reservoir and, from the fluidic reservoir, to the gas chamber in fluidic communication with the fluidic reservoir. The flow of gas through the fluidic reservoir containing one or more fluids (and one or more reagents) and into the gas chamber may cause the one or more fluids and the one or more reagents to mix. In some embodiments, the flow of gas through the fluid contained within the fluidic reservoir results in turbulent flow within the fluid. Without wishing to be bound by theory, turbulent flow may result in mixing of the fluid(s) and/or reagent(s) within the fluidic reservoir.

For example, referring again to FIG. 2, a fluid may be introduced into fluidic reservoir 120. In some embodiments, a gas may be flowed from fluidic hub 110 into fluidic reservoir 120 (via valve 122 and branching channel 125) such that the gas flows into the fluidic reservoir through the fluid. In some such embodiments, the gas (but not the fluid) may flow into fluidic conduit 195 in fluidic communication gas chamber 190. In some embodiments, the gas chamber may be open to atmosphere and the gas vents to atmosphere.

In certain embodiments, the first fluid and/or reagents are substantially inhibited from flowing into the gas chamber. For example, in some embodiments, a valve (or flow-gate) positioned between the fluidic reservoir and the gas chamber may inhibit one or more fluids and/or reagents from flowing into the gas chamber, while selectively permitting the gas to flow into the gas chamber.

In certain embodiments, the fluidic reservoirs are constructed, arranged, and operated in order to perform a set of particular operations. In an exemplary embodiment, the set of operations includes selective depletion of select eukaryote DNA from a sample (e.g., via lysing of select eukaryote cells and/or isolating extracting their genomic material), lysing of one or more microbial cells in the same, isolation of microbial genomic material (e.g, DNA and/or RNA), amplification of the microbial genomic material, reaction with duplex DNA Invading Artificial Nucleic Acids (DIANAs), and detection of one or more microbial pathogen. In some such embodiments, one or more additional washing, isolation, reaction, mixing, or other operations may also be conducted.

Figure 5:
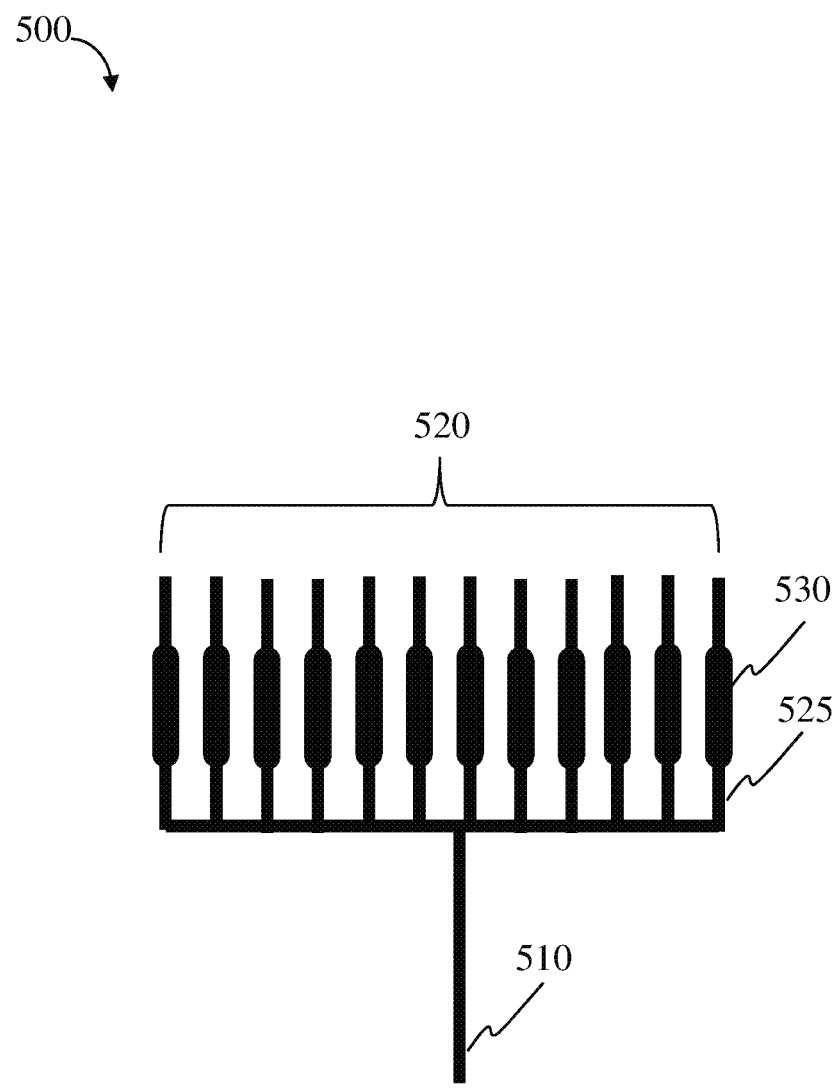
FIG. 5 is a schematic illustration of a fluidic device, according to one set of embodiments.

In some embodiments, after one or more operations described above, the fluid (e.g., the fluid including the amplicon(s) and/or an invasion buffer) may be divided into one or more processing chambers for metering, (e.g., in metering channels) DIANA binding/invasion, and/or detection (e.g., a detection region). In some embodiments, one or more processing chambers are each in fluidic communication with at least one reaction region and/or the amplification region. In some cases, one or more processing chambers may be in fluidic communication with one or more additional regions comprising one or more fluidic reservoirs described herein. In some embodiments, one or more processing chambers may be in fluidic communication with the fluidic hub. In some embodiments, the fluidic device comprises two or more, three or more, four or more, six or more, eight or more, ten or more, twelve or more, fourteen or more, or sixteen or more processing chambers. For example, as illustrated in FIG. 5, fluidic device 500 comprises fluidic channel 510 in fluidic communication with plurality of processing chambers 520 each comprising a metering channel 525. In certain embodiments, each metering channel has the same length, volume, length-to-width ratio, and or cross-sectional dimension as one another. In some cases, the use of metering channels divides a fluid flowing into each metering channel substantially equally. Advantageously, the use of metering channels may produce two or more volumes of fluid that are substantially equal (e.g., such that detection of one or more pathogens contained within the fluid are conducted at equal volumes and substantially simultaneously).

In certain embodiments, the processing chamber comprises a detection region. For example, referring again to FIG. 5, each processing chamber comprises detection region 530 in fluidic communication with metering channel 525. In some embodiments, each detection region may be in fluidic communication with one or more additional regions comprising one or more fluidic reservoirs described herein. In certain embodiments, each detection region is in fluidic communication with each processing chamber. In some cases, one or more detection regions may be in fluidic communication with the fluidic hub. In some embodiments, one or more probes targeting desired pathogens are contained within each detection region. In some such embodiments, the presence of one or more microbial pathogens may be detected by the binding of one or more probes with the pathogen and generating a signal. In some embodiments, the signal is detectable through optical, chemical, electrical, or mechanical detection methods.

In some embodiments, after an amplification operation, the amplicon which were developed/created during enzymatic amplification may be detected and/or identified (e.g., within a metering channel).

In some embodiments, DNA Invading Artificial Nucleic Acids (DIANAs) may be used detect and identify microbial genomic materials. For example, in some embodiments, DIANAs may be added to a fluidic reservoir containing the amplicons produced during the amplification operation. In certain embodiments, one or more DIANAs may be present in the detection region of one or more metering channels.

Figure 6A:
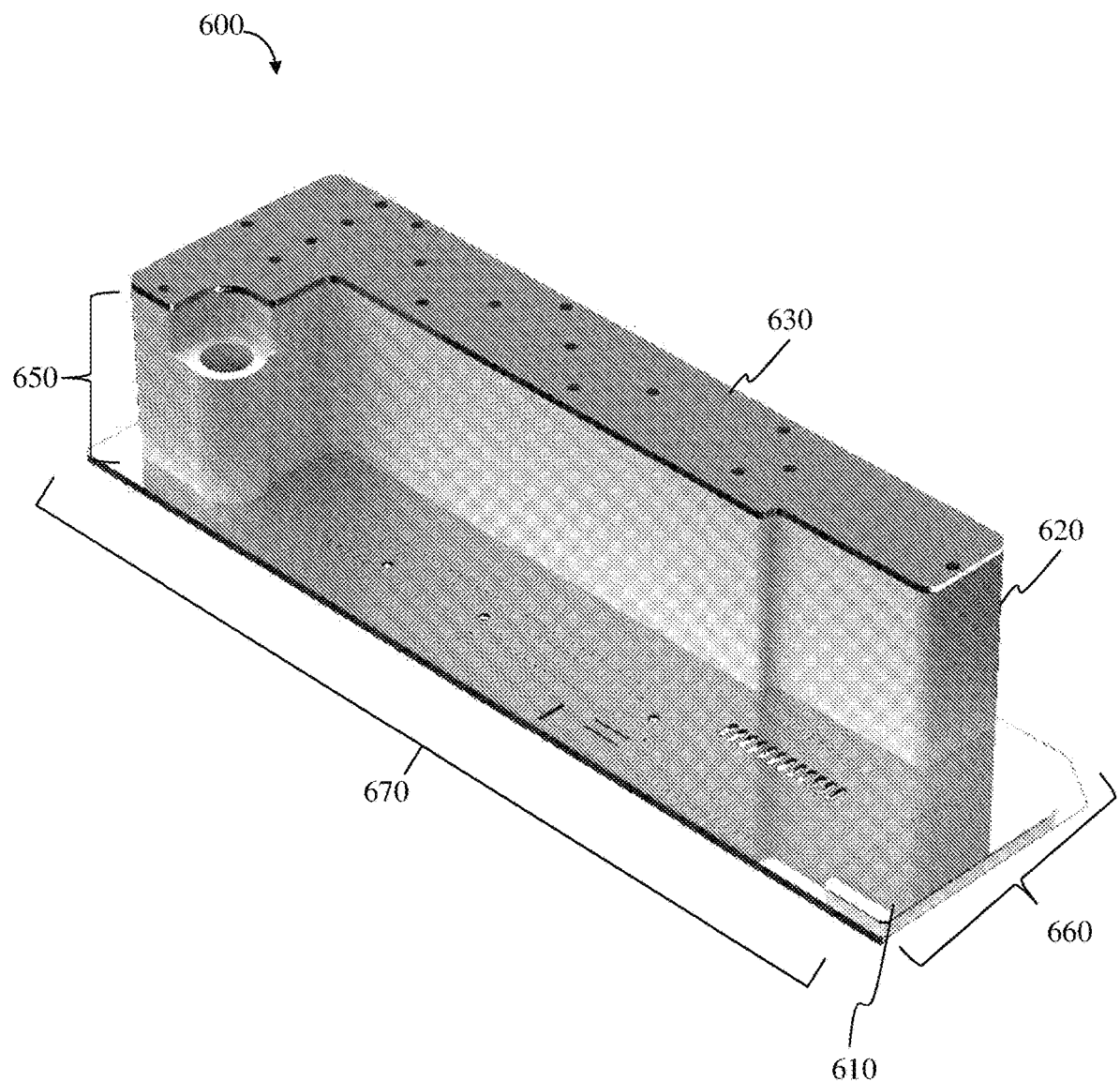
FIG. 6A is a schematic illustration of an exemplary fluidic device, according to one set of embodiments.
Figure 6B:
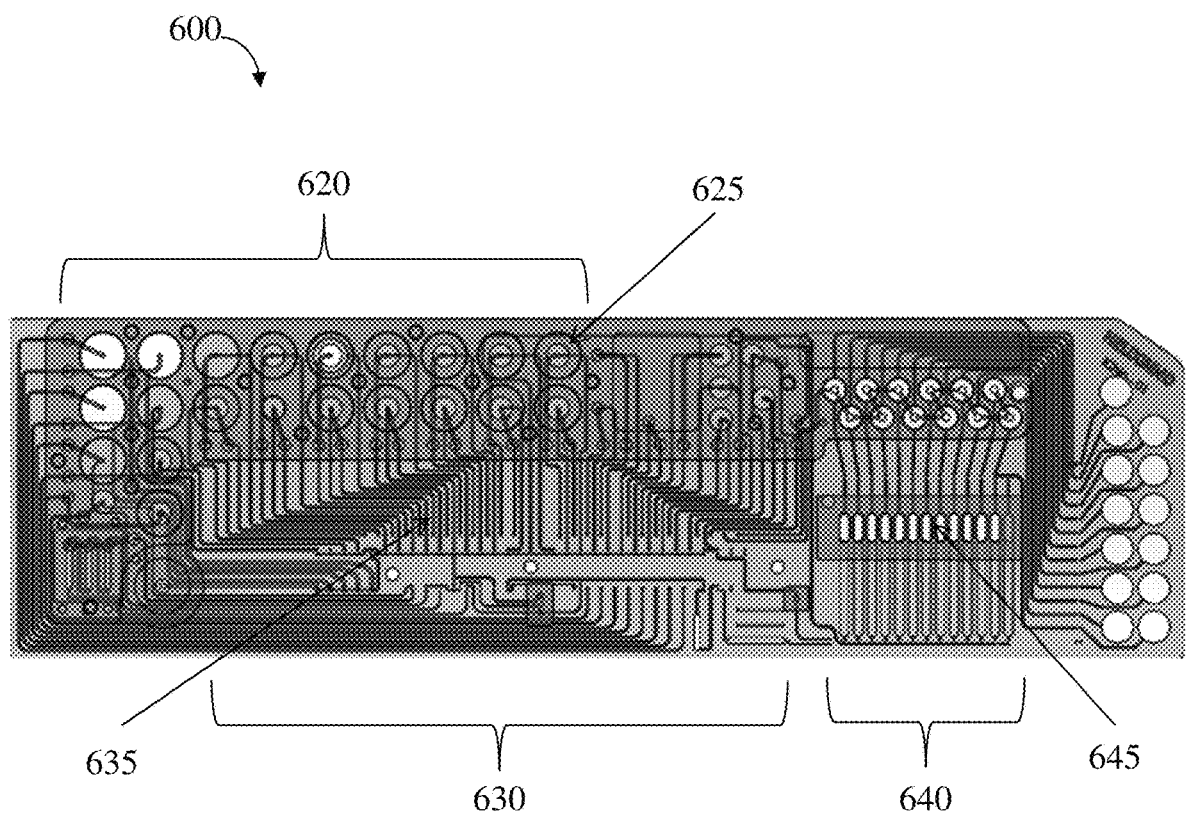
FIG. 6B is a schematic illustration of an exemplary fluidic device, according to one set of embodiments.

An exemplary perspective view of a fluidic device is shown in FIG. 6A. In some embodiments, fluidic device 600 comprises a first region 610 comprising a plurality of fluidic channels and a second region 620 comprising a plurality of fluidic reservoirs. In some cases, the fluidic device comprises cover 630 comprising a plurality of fluidic conduits (e.g., fluidic conduits positioned between one or more gas chambers and one or more fluidic reservoirs). FIG. 6B is a top-down view of fluidic device 600. In some embodiments, second region 620 comprises one or more fluidic reservoirs including, for example, exemplary fluidic reservoir 625. In certain embodiments, first region 610 comprises a plurality of fluidic channels including, for example, exemplary fluidic channels 635. As illustrated in FIG. 6B, the fluidic device further comprises a plurality of metering channels 640 (each metering channel comprising detection region 645).

In some embodiments, first region 610 comprising the plurality of fluidic channels further comprises a thin-film (e.g., a thin film polymer) attached to the bottom of the fluidic device (e.g., to enclose the fluidic channels). In some cases, the thin-film attached to the bottom of the device has relatively high optical transparency (e.g., to facilitate efficient detection of any optical signal emitted from one or more detection regions).

In some embodiments, the fluidic device has an overall width, an overall height, and an overall length. For example, referring again to FIG. 6B, fluidic device 600 has an overall height 650, and overall width 660, and an overall length 670.

In certain embodiments, the fluidic device has a ratio of overall height to overall width of at least 1:1, at least 2:1, at least 3:1, at least 5:1, or at least 10:1. In some embodiments, the fluidic device has a ratio of overall height to overall length of at least 1:1, at least 2:1, at least 3:1, at least 5:1, or at least 10:1.

In certain embodiments, the fluidic device has a particular overall width. In some embodiments, the fluidic device has a width of about 2-5 inches, about 2.5-5 inches, 3-6 inches.

In certain embodiments, the fluidic device has a particular overall length. In some embodiments, the fluidic device has a length of about 5-12 inches, about 6-16 inches, or 8-20 inches.

In some embodiments, the fluidic device occupies a particular surface area. In some embodiments, the fluidic device occupies a surface area of about 10-63 inches squared, about 17-85 inches squared, about 23-115 inches squares, or about 28-120 inches squared. The surface area as described herein is measured on the largest cross-section of the fluidic device parallel to the plurality of fluidic channels (and perpendicular to at least one fluidic reservoir).

In some embodiments, the fluidic device includes an opening for adding the sample, e.g., injecting the sample into the sample inlet reservoir. In some embodiments, the opening has a re-sealable cover. In some embodiments, opening the cover requires mechanical force, wherein without mechanical force the cover remains closed. In some embodiments, the opening is covered with a membrane through which the sample is inserted.

In some embodiments, the fluid sample or specimen is flowed to the fluidic device via a receptacle in the fluidic device constructed and arranged to receive and extract a fluid samples from a vacuette or similar specimen tube or vial.

In some embodiments, the fluidic device comprises a receptacle constructed and arranged to receive a Monovette. By applying force/pressure on the plunger of the Monovette, the fluid specimen from the Monovette is flowed to the fluidic device via the receptacle. In some embodiments, the fluidic device comprises a receptacle constructed and arranged to receive a Vacuette. In some embodiments, the fluidic device comprises a receptacle constructed and arranged to receive any container capable and/or storing and/or transporting a fluid.

In some embodiments, the fluidic device is constructed and arranged to incorporate one or more tubes designed to flow the sample from a specimen vial or receptacle. In some embodiments, such tubes, each and individually, may provide positive pressure, negative pressure, and/or ambient pressure to facilitate the flow of the sample into the device. In some embodiments one or more tubes are designed to work in tandem, and/or in parallel, and or serially, to enable efficient flow of the sample into the device. In some embodiments, only a single tube is required.

In some embodiments, and in cases where more than a single tube may be used to flow the sample from the vial to the fluidic device may be placed in in close proximity, a non-limiting example would be 'side-by-side'. In another non-limiting example, one tube may be placed inside another tube.

In some embodiments, these tubes may serve to puncture the seal of the vial prior to enabling flow of the sample to the fluidic device.

In some embodiments, the sample is flowed from the vial to the fluidic device through pneumatic force, whereas in other cases it might be mechanical or electrical.

In some embodiments, the methods and/or devices described herein may be utilized for the analysis (e.g., identification, and/or detection, and/or screening, and/or qualification) of more than 10 individual microbial pathogens from a single whole-blood sample. In some embodiments, the whole-blood sample introduced into the fluidic device has a volume of at least 1 mL. In some cases, the methods and/or fluidic devices described herein may be utilized for the analysis (e.g., identification, and/or detection, and/or screening, and/or quantification, and/or monitoring) of bacteria and/or fungi. In some embodiments, the analysis comprises high sensitivity chemiluminescent detection.

In some embodiments, the methods and/or devices lyse both bacteria and fungi in a single reaction, in parallel, though chemical reactions (e.g., without the use of mechanical or electrical forces). In certain embodiments, the methods and/or devices described herein comprise depletion of select eukaryote DNA from a whole-blood sample without the use of a centrifuge.

In certain embodiments, the methods and/or devices described herein does not shear genomic material during the lysis process (e.g., thereby enabling the extraction and/or isolation of high molecular weight genomic material of which is typically over 5 kbp in length). In certain embodiments, the methods and/or devices described herein comprise enzymatically producing amplicons greater than 1000 bp in length. In some cases, the method and/or devices described herein comprise immobilizing DNA to a solid substrate in under 30 minutes wherein the DNA length is greater than 1 kbp.

In some embodiments, the methods and/or devices described herein do not require the use of any chaotropic salt for any of its processes.

In some embodiments, one or more operations, or set of operations, described herein may be conducted semiautomatic or automatically.

In certain embodiments, one or more fluidic reservoirs may store one or more reagents and/or may be configured to receive a waste fluid.

In some embodiments, the methods and/or devices comprise the transfer (e.g., flow) of one or more fluids along three planes (X,Y, and Z) in both positive and negative directionality (e.g., through the use of flow restriction structures). In certain embodiments, the plurality of fluidic channels used for transferring fluids from a first fluidic reservoir to a second fluidic reservoir are located within a single plane. In certain embodiments, one or more fluids flowed in the fluidic device may have a relatively large volume (e.g., 0.5-10 ml) or a relatively reduced volume (e.g., 0.01 µl-500 µl).

In some cases, the methods and/or devices comprises mixing, agitation, and/or homogenization of a fluid (e.g., and one or more reagents) via the addition, either as a stream or as a pulsation, of a sterile gas to a chamber.

Combinatorics Microbial Detection

In certain embodiments, the methods and/or devices described herein comprise DIANA probes to capture and immobilize DNA to a solid surface or substrate with sequence high sequence specificity. In some cases, the methods and/or devices described herein comprise combining a plurality of DIANA probes within one or more processing chambers such that a combination of one or more signals elucidates the identification of the pathogen (e.g., thereby reducing the number of processing chambers needed to elucidate the identification of the pathogen).

In some embodiments, the location of the detection region will yield the information as to which target was captured (e.g., due to the presence of a DIANA probe). In some embodiments, a combination of detected color (e.g., when fluorescence is used as the optical detection modality) and location can be used to decipher which target was captured.

In some embodiments, the presence of a signal (e.g., an optical signal) in one or more of the detection regions indicates the presence of the genomic material of a particular microbial pathogen. In some embodiments, the detection of a particular analyte (e.g., microorganism or pathogen) is provided through a combinatorics (e.g., multiplexing) method. In such an approach, the number of analytes detected may be larger than the number of active detection regions used for detection. In some embodiments, the fluidic device comprises two or more detection regions. In some embodiments, the particular combination of detection regions that detect one or more amplicons (e.g., by producing a detectable signal such as an optical signal) may indicate the presence of one or more particular pathogen.

In one, non-limiting, example, a signal detected in a first detection region and a second detection region, but not a third detection region, indicates the presence of a first pathogen in the patient sample. A signal detected in the first detection region and the third detection region, but not the second detection region, indicates the presence of a second pathogen in the patient sample, different than the first pathogen.

The use of a combinatorics approach to detection may provide several advantages over traditional 1-to-1 detection methods (e.g., detection of a pathogen in a single well, and/or single pathogen detection across multiple wells) including, for example, simplified fluidic channel design, reduced footprint, reduced processing times, increased accuracy, and/or simplified detection.

In some embodiments, a single type of optical signal (e.g., an optical signal at a particular wavelength) may be used for the detection of a plurality of pathogens. For example, a single fluorescent tag may be used in the fluidic device and, in the presence of a pathogen, one or more detection regions produce a detectable optical signal from the fluorescent tag indicating the presence of the genomic material of a particular microbial pathogen.

In the case of pathogen-specific genomic material, one could identify the different pathogenic genomic material (PGM) associated with a particular pathogen as $PGM_n$ wherein n=1, 2, 3, . . . , n. For example, in some embodiments, in a fluidic device design to identify one of fifteen potential pathogens, the fluidic device could identify $PGM_n$ wherein n=1, 2, 3, . . . , 15, where the fifteen potential pathogens could be detected using 8 detection regions. In an exemplary embodiment, shown in Table 6, the presence of particular capture oligomers in one or more detection regions would indicate the presence of a particular pathogen in the patient sample.

TABLE 6

| Detection Region | DIANA Capture Oligomers |
|---|---|
| 1 | $PGM_1 + PGM_2 + PGM_3 + PGM_4 + PGM_5$ |
| 2 | $PGM_6 + PGM_7 + PGM_8 + PGM_9 + PGM_{10}$ |
| 3 | $PGM_{11} + PGM_{12} + PGM_{13} + PGM_{14} + PGM_{15}$ |
| 4 | $PGM_1 + PGM_6 + PGM_{11}$ |
| 5 | $PGM_2 + PGM_7 + PGM_{12}$ |
| 6 | $PGM_3 + PGM_8 + PGM_{13}$ |
| 7 | $PGM_4 + PGM_9 + PGM_{14}$ |
| 8 | $PGM_5 + PGM_{10} + PGM_{15}$ |

For example, in a particular embodiment, if a detectable signal is generated in detection regions 1 and 4, the only common PGM is $PGM_1$, indicating the particular pathogen present in the patient sample corresponding to $PGM_1$. As another example, in another embodiment, if a detectable signal is generated in detection regions 1 and 7, the only common PGM is $PGM_4$, indicating the particular pathogen present in the patient sample corresponding to $PGM_4$.

The terms "panel" or "menu", as are used herein, refer to the microorganisms that any given assay is designed to detect. For example, if an assay is designed to detect $PGM_n$ microorganisms, then there will be n distinct microorganisms in the panel.

Those skilled in the art would understand, based upon the teachings of this specification, that such a combinatorics approach is not limited to 15 potential pathogens and/or 8 detection regions, but that the combinatorial method could be used to detect two or more, four or more, six or more, eight or more, ten or more, twelve or more, fifteen or more, or twenty or more, fifty or more, one-hundred or more, two hundred or more, five-hundred or more pathogens using two or more (e.g., four or more, six or more, eight or more, ten or more, twelve or more, fifteen or more, twenty-five or more, fifty or more) detection regions.

In some embodiments, the detection of one or more pathogens does not use a combinatorics approach. For example, each detection region, in certain embodiments, corresponds to a single pathogen.

Culture-Free Microbial Diagnosis of Infective Endocarditis

Infective Endocarditis (IE) affects >45,000 patients in the US annually, predominantly those with preexisting conditions such as heart valve damage or invasive procedures, and is characterized by high morbidity and mortality (20-40%). IE is now considered one of the most life-threatening infections in the US. IE can occur when bacteria or fungi adhere to the endocardial surface and form small lesions or 'vegetations'. These vegetations contain high pathogen concentrations, and are not only difficult to eradicate, but induce 'persistent septicemia' as the microorganisms are continuously released into the bloodstream.

The inconsistent and non-specific clinical presentation of IE presents a significant challenge to accurate and timely diagnosis. Currently, IE is diagnosed through a diverse set of criteria (Duke criteria) which include patient medical history, febrile response, echocardiograms and, crucially, microbiological evidence based on positive blood cultures. Poor outcomes, in turn, have been directly linked to the inability to correctly diagnose IE early enough in the disease's time course. As prognosis deteriorates rapidly in the absence of proper antimicrobial intervention, it is well accepted that time to confirmation of the bloodstream infection (BSI) with the corresponding ID of the microorganism is one of the key determinants of outcome. However, current diagnostic standards to detect microorganisms rely on blood cultures, which are not only time-consuming, but also ineffective in detecting fastidious pathogens or an infection from patients pre-treated with antibiotics, resulting in a significant numbers of culture-negative IE cases. Although current molecular methods have the potential to overcome some of these problems, they have significant shortcomings with respect to panel size, sensitivity, level of detail, and time requirements, and therefore, clinical acceptance is low. Given that timely BSI confirmation with the corresponding ID is a prerequisite to proper disease management, the current microbiological diagnostic protocol is clearly outdated.

Among diagnostic criteria to establish IE, culturing results are indispensable. The use of blood cultures to identify the etiologic agent of IE has, however, two major weaknesses which delay the administration of the proper antimicrobial therapy: (1) long turnaround time of days or even weeks and (2) high prevalence of false-negatives due to either pre-treatment with antibiotics or the presence of difficult to culture pathogens. As is described herein, the methods described herein excel at detecting a large panel of pathogens at very low loads.

Pathogens prevalent in cases of IE include, for example, *Staphylococcus aureus*, Coagulase Negative Staphylococci (CoNS), *Enterococcus faecalis, Streptococcus pneumoniae, Streptococcus agalactiae, Streptococcus pyogenes, Candida albicans, Candida parapsilosis*, viridans group streptococci (VGS; specifically, *Streptococcus mitis, Streptococcus oralis, Streptococcus mutans, Streptococcus sanguinis, Streptococcus anginosis*, and *Streptococcus salivarius*), *Streptococcus galloyticus*, and the HACEK group, comprising of *Haemophilus parainfluenzae, Aggregatibacter actinomycetemcomitans, Cardiobacterium hominis*, Eikenella corrodens, Kingella spp., *Coxiella burnetii*, and *Bartonella* spp. In some embodiments, a test panel or test menu comprises all of the preceding pathogens. In some embodiments, a test panel or test menu comprises a subset of the preceding pathogens. In some embodiments, a test panel or test menu comprises only one of the preceding pathogens. In some embodiments, a test panel or test menu comprises some or all of the preceding pathogens and additional microorganisms not listed.

DIANAs that bind to the single species or group of microbes associated with endocarditis and/or sepsis are listed in Table 7. In some embodiments, one of the DIANA probes listed in Table 7 is used in the methods, devices, and kits described herein, e.g., in a method of identifying a single species or group of microbes which is associated with endocarditis and/or sepsis. In some embodiments, some of the DIANA probes listed in Table 7 are used in the methods, devices, and kits described herein, e.g., in a method of identifying a single species or group of microbes which is associated with endocarditis and/or sepsis. In some embodiments, all of the DIANA probes listed in Table 7 are used in the methods, devices, and kits described herein, e.g., in a method of identifying a single species or group of microbes which is associated with endocarditis and/or sepsis. In some embodiments, some or all of the DIANA probes listed in Table 7 are used in combination with DIANA probes not listed in Table 7 in the methods, devices, and kits described herein, e.g., in a method of identifying a single species or group of microbes which is associated with endocarditis and/or sepsis.

TABLE 7

| DIANAs and microorganisms commonly associated with infective endocarditis | | | |
|---|---|---|---|
| Microorganism | Seq ID | Microorganism | Seq ID |
| Staphylococcus Aureus | 001 | Eikenella corrodens | 032-038 |
| Coagulase Negative Staphylococci | 002, 003, and 020-031 | Kingella kingae | 039-045 |
| Enterococcus Faecalis | 004 | Aggregatibacter actinomycetemcomitans | 046-050 |
| Streptococcus pneumoniae | 005 | Haemophilus parainfluenzae | 051, and 052 |
| Streptococcus agalactiae | 006 | Haemophilus influenzae | 053-058 |
| Streptococcus Pyogenes | 007 | Cardiobacterium hominis | 125-131 |
| Candida Albicans | 015 | Coxiella burnetii | 068-124 |
| Candida parapsilosis | 016 | Bartonella spp. X | 064-067 X |
| Viridans streptococci | 059-063 | | |

In some embodiments, DIANAs that bind to the single species or group of microbes associated with endocarditis and/or sepsis comprise SEQ ID NOs: 1-7, 15, 16, and 20-131. In some embodiments, one of the DIANA probes having the sequence of SEQ ID NOs: 1-7, 15, 16, and 20-131 is used in the methods, devices, and kits described herein, e.g., in a method of identifying a single species or group of microbes which is associated with endocarditis and/or sepsis. In some embodiments, some of the DIANA probes having the sequence of SEQ ID NOs: 1-7, 15, 16, and 20-131 are used in the methods, devices, and kits described herein, e.g., in a method of identifying a single species or group of microbes which is associated with endocarditis and/or sepsis. In some embodiments, all of the DIANA probes having the sequence of SEQ ID NOs: 1-7, 15, 16, and 20-131 are used in the methods, devices, and kits described herein, e.g., in a method of identifying a single species or group of microbes which is associated with endocarditis and/or sepsis. In some embodiments, some or all of the DIANA probes having the sequence of SEQ ID NOs: 1-7, 15, 16, and 20-131 are used in combination with DIANA probes not having the sequence of SEQ ID NOs: 1-7, 15, 16, and 20-131 in the methods, devices, and kits described herein, e.g., in a method of identifying a single species or group of microbes which is associated with endocarditis and/or sepsis.

Exemplary DIANA probe sequences for *Staphylococcus aureus*, Coagulase Negative Staphylococci, *Enterococcus faecalis*, *Streptococcus pneumoniae*, *Streptococcus agalactiae*, *Streptococcus pyogenes*, *Candida albicans*, and *Candida parapsilosis* are shown in Table 1.

Exemplary DIANA probe sequences for Coagulase Negative Staphylococci, *Viridans* streptococci, Eikenella corrodens, Kingella kingae, *Aggregatibacter actinomycetemcomitans*, *Haemophilus parainfluenzae*, *Haemophilus influenzae*, *Cardiobacterium hominis*, *Coxiella burnetii*, and *Bartonella* spp. are shown in Table 2. Additional DIANA probe sequences for *Staphylococcus aureus*, Coagulase Negative Staphylococci (CoNS), *Enterococcus faecalis*, *Streptococcus pneumoniae*, *Streptococcus agalactiae*, *Streptococcus pyogenes*, *Candida albicans*, and *Candida parapsilosis* have been identified in WO2013176992A2.

A non-limiting example of 8-well detection system for the fluidic device described herein incorporating the microorganisms or pathogens listed in Table 7 is shown in Table 8. In the example illustrated in Table 8, pathogen ID can be determined based on an optical signature from two detection wells, rather than just one. For example, a *S. aureus* infection would be identified by signals from wells #2 and #5, and would be discriminated from an *E. faecalis* infection, which would be identified by wells #2 and #7.

TABLE 8

| Well | DIANA Probe 1 | | DIANA Probe 2 | | DIANA Probe 3 | | DIANA Probe 4 | | DIANA Probe 5 |
|---|---|---|---|---|---|---|---|---|---|
| 1 | H. parainfluenzae | + | A. actinomycetem-comitans | + | C. hominis | + | E. corrodens | + | Kingella spp. |
| 2 | S. aureus | + | CoNS | + | E. faecalis | + | Viridans group | + | |
| 3 | S. pneumoniae | + | S. agalactiae | + | S. pyogenes | + | S. gallolyticus | + | |
| 4 | C. albicans | + | C. parapsilosis | + | C. burnetii | + | Bartonella spp. | + | |
| 5 | H. parainfluenzae | + | S. aureus | + | S. pneumoniae | + | C. albicans | + | |

TABLE 8-continued

| Well | DIANA Probe 1 | | DIANA Probe 2 | | DIANA Probe 3 | | DIANA Probe 4 | | DIANA Probe 5 |
|---|---|---|---|---|---|---|---|---|---|
| 6 | *A. actinomycetemcomitans* | + | CoNS | + | *S. agalactiae* | + | *C. parapsilosis* | + | |
| 7 | *C. hominis* | + | *E. faecalis* | + | *S. pyogenes* | + | *C. burnetii* | + | |
| 8 | *E. corrodens* | + | *Kingella* spp. | + | Viridans group | + | *S. gallolyticus* | + | *Bartonella* spp. |

Culture-Free Microbial Identification of Pathogens Prevalent in Neonatal Septicemia Neonatal sepsis is a significant health risk for newborns. While advances in patient care have helped to reduce its incidence, an estimated 9,100 newborns are afflicted with this disease in the US annually, and over 3,000 will not survive. It is well documented that the prognosis for these vulnerable patients deteriorates every hour an infection is not appropriately counteracted. Early confirmation of a BSI with the corresponding ID of the microorganism can be the key determinant of outcome as this minimizes the time-lag for targeted antimicrobial intervention. Unfortunately, blood cultures, the current diagnostic standard for detection of BSIs, typically requires several days for results. Moreover, culturing is particularly problematic in newborns as reduced blood-draw volumes often lead to false-negative results, and the prevalence of maternal antibiotics can significantly reduce sensitivity. Faced with this reality, clinicians routinely initiate treatment on a purely empirical basis in the absence of diagnostic confirmation. Although a necessary risk, these approaches are inefficient, expensive, potentially miss the target, and increase the likelihood of complications including adverse responses and drug-drug interactions. For newborns with a BSI, appropriate antimicrobial intervention is critically delayed, while newborns without a BSI are exposed to unnecessary antimicrobials, potentially jeopardizing healthy microbiome development. Thus, the current use of blood culturing is the only method to detect the etiologic agent of a BSI and is a crucial impediment to improved patient care.

The use of cultures to identify the etiologic agent of neonatal BSIs has two major weaknesses which delay the administration of the proper antimicrobial: (1) Long turn-around time of days, and (2) high prevalence of false-negative results, often due to pre-treatment with antibiotics (often from the mother), combined with a reduced blood draw volume lowering sensitivity. While molecular methods, in principle, are capable of tackling these issues, they have been unable to consistently reach the required sensitivity, cover a sufficient number of pathogens simultaneously, or reach the level of detail required to provide actionable information. In contrast to blood culturing, the claimed methods, devices and kits allow the rapid and accurate identification of low levels of microorganisms in small volumes of blood.

Pathogens prevalent in cases of neonatal sepsis include, for example, *Staphylococcus aureus*, Coagulase Negative Staphylococci (CoNS), *Enterococcus faecalis*, *Enterococcus faecium*, *Streptococcus pneumoniae*, *Streptococcus agalactiae*, *Streptococcus pyogenes*, *Candida albicans*, *Candida parapsilosis*, viridans group streptococci (VGS; specifically, *Streptococcus mitis*, *Streptococcus oralis*, *Streptococcus mutans*, *Streptococcus sanguinis*, *Streptococcus anginosis*, and *Streptococcus salivarius*), *Listeria monocytogenes*, *Escherichia coli*, *Enterobacter* spp., *Klebsiella* spp., *Pseudomonas aeruginosa*, *Acinetobacter baumannii*, *Haemophilus influenza*, *Neisseria meningitides*, *Candida albicans*, and *Candida parapsilosis*. In some embodiments, a test panel or test menu comprises all of the preceding pathogens. In some embodiments, a test panel or test menu comprises a subset of the preceding pathogens. In some embodiments, a test panel or test menu comprises only one of the preceding pathogens. In some embodiments, a test panel or test menu comprises some or all of the preceding pathogens and additional microorganisms not listed.

DIANAs that bind to the single species or group of microbes associated with neonatal sepsis are listed in Table 9. In some embodiments, one of the DIANA probes listed in Table 9 are used in the methods, devices, and kits described herein, e.g., in method of identifying a single species or group of microbes which is associated with neonatal sepsis. In some embodiments, some of the DIANA probes listed in Table 9 are used in the methods, devices, and kits described herein, e.g., in method of identifying a single species or group of microbes which is associated with neonatal sepsis. In some embodiments, all of the DIANA probes listed in Table 9 are used in the methods, devices, and kits described herein, e.g., in method of identifying a single species or group of microbes which is associated with neonatal sepsis. In some embodiments, some or all of the DIANA probes listed in Table 9 are used in combination with DIANA probes not listed in Table 9 in the methods, devices, and kits described herein, e.g., in method of identifying a single species or group of microbes which are commonly associated with neonatal sepsis.

TABLE 9

DIANAs and microorganisms commonly associated with neonatal sepsis

| Microorganism | Seq ID | Microorganism | Seq ID |
|---|---|---|---|
| *Staphylococcus Aureus* | 001 | *Enterococcus Faecium* | 008 |
| Coagulase Negative *Staphylococci* | 002, 003, and 020-031 | *Escherichia coli* | 140 |
| *Enterococcus Faecalis* | 004 | *Enterobacter* spp./ *Klebsiella* spp. | 009 |
| *Streptococcus Pneumoniae* | 005 | *Pseudomonas Aeruginosa* | 010, and 011 |
| *Streptococcus Agalactiae* | 006 | *Serratia Marcescens* | 013, and 014 |
| *Streptococcus Pyogenes* | 007 | *Acinetobacter Baumannii* | 012 |
| *Candida Albicans* | 015 | *Listeria monocytogenes* | 132-137 |
| *Candida Parapsilosis* | 016 | *Neisseria Meningitides* | 138, and 139 |
| Viridans Streptococci | 059-063 | *Haemophilus Influenza* | 053-058 |

DIANAs that bind to the single species or group of microbes commonly associated with neonatal sepsis have the sequence of SEQ ID NOs: 1-16, 20-31, 53-63, and 132-140. In some embodiments, one of the DIANA probes having the sequence of SEQ ID NOs: 1-16, 20-31, 53-63, and 132-140 is used in the methods, devices, and kits described herein, e.g., in method of identifying a single species or group of microbes which are commonly associated with neonatal sepsis. In some embodiments, some of the DIANA probes having the sequence of SEQ ID NOs: 1-16, 20-31, 53-63, and 132-140 are used in the methods, devices, and kits described herein, e.g., in method of identifying a single species or group of microbes which are commonly associated with neonatal sepsis. In some embodiments, all of the DIANA probes having the sequence of SEQ ID NOs: 1-16, 20-31, 53-63, and 132-140 are used in the methods, devices, and kits described herein, e.g., in method of identifying a single species or group of microbes which are commonly associated with neonatal sepsis. In some embodiments, some or all of the DIANA probes having the sequence of SEQ ID NOs: 1-16, 20-31, 53-63, and 132-140 are used in combination with DIANA probes not having the sequence of SEQ ID NOs: 1-16, 20-31, 53-63, and 132-140 in the methods, devices, and kits described herein, e.g., in method of identifying a single species or group of microbes which are commonly associated with neonatal sepsis.

Exemplary DIANA probe sequences for *Staphylococcus aureus*, Coagulase Negative Staphylococci, *Enterococcus faecalis*, *Streptococcus pneumoniae*, *Streptococcus agalactiae*, *Streptococcus pyogenes*, *Candida albicans*, *Candida parapsilosis*, *Pseudomonas aeruginosa*, *Serratia marcescens*, and *Acinetobacter baumannii* are listed in Table 1. Exemplary DIANA probe sequences for Coagulase Negative Staphylococci, *Viridans* streptococci, and *Haemophilus influenzae* are listed in Table 2. Exemplary DIANA probe sequences for *Listeria monocytogenes* and *Neisseria meningitides* are listed in Table 3. Additional DIANA probe sequences for *Staphylococcus aureus*, Coagulase Negative Staphylococci (CoNS), *Enterococcus faecalis*, *Enterococcus faecium*, *Streptococcus pneumoniae*, *Streptococcus agalactiae*, *Streptococcus pyogenes*, *Escherichia coli*, *Enterobacter* spp./*Klebsiella* spp., *Pseudomonas aeruginosa*, *Acinetobacter baumannii*, *Candida albicans*, and *Candida parapsilosis* have been identified in WO2013176992A2.

A non-limiting example of 9-well detection system for the fluidic device described herein incorporating the microorganisms or pathogen listed in Table 9 is shown in Table 10. In the example illustrated in Table 10, pathogen ID will be determined based on an optical signature from two detection wells, rather than just one. For example, a *S. aureus* infection would be identified by signals from wells #2 and #6, and would be discriminated from an *E. faecalis* infection, which would be identified by wells #3 and #6.

TABLE 10

|  | DIANA Probe 1 |  | DIANA Probe 2 |  | DIANA Probe 3 |  | DIANA Probe 4 |
|---|---|---|---|---|---|---|---|
| Well 1 | S. aureus | + | S. agalactiae | + | Enterobacter spp./Klebsiella spp. | + | C. albicans |
| Well 2 | CoNS | + | S. pyogenes | + | P. aeruginosa | + | C. parapsilosis |
| Well 3 | E. faecalis | + | Viridans group | + | A. baumannii | + | N. meningitides |
| Well 4 | E. faecium | + | L. monocytogenes | + | H. influenza | + | E. coli |
| Well 5 | S. pneumoniae | + | E. coli | + | N. meningitides | + |  |
| Well 6 | S. aureus | + | CoNS | + | E. faecalis | + | E. faecium |
| Well 7 | S. agalactiae | + | S. pyogenes | + | Viridans group | + | L. monocytogenes |
| Well 8 | Enterobacter spp./Klebsiella spp. | + | P. aeruginosa | + | A. baumannii | + | H. influenza |
| Well 9 | C. albicans |  | C. parapsilosis |  | S. pneumoniae |  | + |

Culture-Free Microbial Detection of Gram-Positive Pathogens Prevalent in Bloodstream Infections and their Resistance Conferring Mechanisms Bacteremia, i.e., sepsis, continues to be a significant healthcare burden in the US. As prognosis deteriorates by the hour, early diagnosis has long been established as vital for providing the best patient care. Current diagnostic standards using blood culturing are ill-fitted for timely diagnosis as they take days to deliver results. Moreover, culturing tends to be inhibited by antimicrobials, adding uncertainty to negative results. Considering the rapid decline of survival rates if proper antibiotics are not administered within a few hours, clinicians routinely initiate treatment on a purely empirical basis in the absence of diagnostic confirmation. These empirical interventions rely on 'best-guess' approaches which are inefficient, expensive, potentially miss the target and increase the likelihood of complications including adverse responses and drug-drug interactions. However, this is a necessary risk given the lack of timely information. Thus, a key advance critical to reducing the mortality rate is the early identification of bacterial pathogens and their resistance traits directly from clinical specimens, without culturing, enabling a hypothesis driven first-line intervention.

The 'need-to-culture' has been repeatedly identified as the most significant barrier to a targeted therapeutic intervention. The methods, devices, and kits described herein provide a culture-free approach to rapidly and accurately identifying pathogens in the blood.

The methods, devices, and kits described herein are directed to detecting infection with a subset of pathogens prevalent in sepsis, specifically Gram-positive bacteria and to detecting their resistance mechanisms. Pathogens prevalent in cases of sepsis include, for example, *Staphylococcus aureus*, Coagulase Negative Staphylococci (CoNS), *Enterococcus faecalis*, *Enterococcus faecium*, *Streptococcus pneumoniae*, *Streptococcus agalactiae*, *Streptococcus pyogenes*, and *viridans* group streptococci (VGS; specifically, *Streptococcus mitis, Streptococcus oralis, Streptococcus mutans, Streptococcus sanguinis, Streptococcus anginosis,* and *Streptococcus salivarius*). In some embodiments, a test panel or test menu comprises all of the preceding pathogens. In some embodiments, a test panel or test menu comprises a subset of the preceding pathogens. In some embodiments, a test panel or test menu comprises only one of the preceding pathogens. In some embodiments, a test panel or test menu comprises some or all of the preceding pathogens and additional microorganisms not listed.

In some embodiments, a panel or menu comprises some or all of the preceding pathogens and marker for antimicrobial resistance conferring genetic material, or antimicrobial resistance conferring gene. In some embodiments, a panel or menu comprises some or all of the preceding pathogens and one or more markers for antimicrobial resistance conferring genetic material. In some embodiments, a panel or menu comprises one or more markers for antimicrobial resistance conferring genetic material. Antimicrobial resistance conferring genetic material include, for example, MecA, MecC and VanA and/or VanB.

DIANAs that bind to genetic material which may confer reduced susceptibility or resistance to antimicrobials are shown in Table 11, e.g., SEQ ID NOs: 141-372. In some embodiments, one of the DIANA probes listed in Table 11, e.g., SEQ ID NOs: 1-8, 20-31, 59-63, and 141-372, is used in the methods, devices, and kits described herein, e.g., methods for identifying genetic material which may confer reduced susceptibility or resistance to antimicrobials. In some embodiments, some of the DIANA probes listed in Table 11, e.g., SEQ ID NOs: 1-8, 20-31, 59-63, and 141-372, are used in the methods, devices, and kits described herein, e.g., methods for identifying genetic material which may confer reduced susceptibility or resistance to antimicrobials. In some embodiments, all of the DIANA probes listed in Table 11, e.g., SEQ ID NOs: 1-8, 20-31, 59-63, and 141-372, are used in the methods, devices, and kits described herein, e.g., methods for identifying genetic material which may confer reduced susceptibility or resistance to antimicrobials. In some embodiments, some or all of the DIANA probes listed in Table 11, e.g., SEQ ID NOs: 1-8, 20-31, 59-63, and 141-372, are used in combination with DIANA probes not listed in Table 11 in the methods, devices, and kits described herein, e.g., methods for identifying genetic material which may confer reduced susceptibility or resistance to antimicrobials.

TABLE 11

DIANAs and microorganisms associated with Gram positive bloodstream infections and antimicrobial resistance or reduced antimicrobial susceptibility.

| Target | Seq ID |
|---|---|
| *Staphylococcus aureus* | 001 |
| Coagulase Negative *Staphylococci* | 002, 003, and 020-031 |
| *Enterococcus faecalis* | 004 |
| *Enterococcus faecium* | 008 |
| *Streptococcus pneumoniae* | 005 |
| *Streptococcus agalactiae* | 006 |
| *Streptococcus pyogenes* | 007 |
| *Viridans streptococci* | 059-063 |
| Gene(s) conferring resistance to antistaphylococcal penicillins | 141-372 |
| Gene(s) conferring resistance to vancomycin | 373-493 |

Exemplary DIANA probe sequence for *Staphylococcus aureus*, Coagulase Negative Staphylococci, *Enterococcus faecalis, Enterococcus faecium, Streptococcus pneumoniae, Streptococcus agalactiae,* and *Streptococcus pyogenes* are shown in Table 1. Exemplary DIANA probe sequence for Coagulase Negative Staphylococci and *Viridans* streptococci are shown in Table 2. Exemplary DIANA probe sequence for antistaphylococcal penicillins and vancomycin antimicrobial resistance genes are shown in Table 4. Additional DIANA probe sequences for *Staphylococcus aureus*, Coagulase Negative Staphylococci (CoNS), *Enterococcus faecalis, Enterococcus faecium, Streptococcus pneumoniae, Streptococcus agalactiae,* and *Streptococcus pyogenes* have been identified in WO2013176992A2.

In some embodiments, the following primers are used in the amplification reaction of the methods described herein:

```
                                  (SEQ ID NO: 582)
        CGG CTA CCT TGT TAC GAC TT;

(SEQ ID NO: 583)
        GAG TTT GAT CCT GGC TCA G;

(SEQ ID NO: 584)
        GGC TGC GAT ATT CAA AGC TC;

(SEQ ID NO: 585)
        GGC TGT GAT ATT CAA AGC TC;

(SEQ ID NO: 586)
        GCC TTT TTC CGG CTC G;

(SEQ ID NO: 587)
        ACT TGT TGA GCA GAG GTT CT;

(SEQ ID NO: 588)
        GTA ACA TTG ATC GCA ACG TTC.
```

In some embodiments primers are used which preferentially amplify only Gram-positive bacteria.

Detection of Multiple Microorganisms and Deconvolving Complex Infections

In some embodiments, using the methods, devices, and kits for detecting microorganisms described herein, more than a single type of microorganism is detected. In a non-limiting example, should both *S. aureus, E. coli,* and *C. albicans* be detected in a single patient blood sample, in some embodiments it is of clinical utility to indicate that all three pathogens may be the source of the disease and all three pathogens need to be treated as such. By way of example but not by way of limitation, treatment might include administering three antimicrobials each specific to the three different pathogens. In some embodiments, using the methods described herein, it might be of clinical utility to indicate the relative loads of each of the three pathogens. In some embodiments, this can be achieved by correlating the output signal to a calibration curve as described previously. In other embodiments, no calibration curve is required as the relationship might be internal to a given test while taking into account the copy-number of the targeted gene prior to enzymatic amplification.

Methods described herein are useful for associating a particular microorganism with an identified antimicrobial resistance or susceptibility gene. By way of example, but not by way of limitation, should be *S. aureus* and CoNS be identified combined with the mecA resistance conferring genetic material, in some embodiments it is of clinical utility to understand the source of the mecA gene given that, often, CoNS may be considered an artifact (i.e. a contaminant) of the blood-draw.

In some embodiments, none of the microorganisms detected have antimicrobial resistance or susceptibility conferring genetic material, e.g., antimicrobial resistance conferring genetic materiallisted in Table 11, which can be targeted by one or more DIANAs listed in Table 4, e.g., SEQ ID NOs: 141-493. In some embodiments, antimicrobial resistance or susceptibility conferring genetic material is detected, e.g., antimicrobial resistance conferring genetic material listed in Table 11, which can be targeted by one or more DIANAs listed in Table 4, e.g., SEQ ID NOs: 141-493. In some embodiments, one of the microorganisms detected have antimicrobial resistance or susceptibility conferring genetic material, e.g., antimicrobial resistance conferring genetic material listed in Table 11, which can be targeted by one or more DIANAs listed in Table 4, e.g., SEQ ID NOs: 141-493. In some embodiments, some of the microorganisms detected have antimicrobial resistance or susceptibility conferring genetic material, e.g., antimicrobial resistance conferring genetic material listed in Table 11, which can be targeted by one or more DIANAs listed in Table 4, e.g., SEQ ID NOs: 141-493. In some embodiments, all microorganisms detected have antimicrobial resistance or susceptibility conferring genetic material, e.g., antimicrobial resistance conferring gene listed in Table 11, which can be targeted by one or more DIANAs listed in Table 4, e.g., SEQ ID NOs: 141-493. In some embodiments, all of the microorganisms detected have antimicrobial resistance or susceptibility conferring genetic material, e.g., antimicrobial resistance conferring genetic material listed in Table 11, which can be targeted by one or more DIANAs listed in Table 4, e.g., SEQ ID NOs: 141-493, and they all have the same antimicrobial resistance or susceptibility conferring genetic material. In some embodiments, all microorganisms detected have antimicrobial resistance or susceptibility conferring genetic material, e.g., antimicrobial resistance conferring genetic material listed in Table 11, which can be targeted by one or more DIANAs listed in Table 4, e.g., SEQ ID NOs: 141-493, and they have different antimicrobial or susceptibility conferring genetic material In some embodiments, one or some of the microorganisms detected have an antimicrobial resistance or susceptibility conferring genetic material, e.g., antimicrobial resistance conferring genetic material listed in Table 11, which can be targeted by one or more DIANAs listed in Table 4, e.g., SEQ ID NOs: 141-493, and the microorganisms are identified as having antimicrobial resistance or susceptibility conferring genetic material. In some embodiments, treatment with an antimicrobial is initiated. In some embodiments, treatment with an antimicrobial is altered, e.g., the antimicrobial is changed.

In some embodiments, one or more of the microorganisms detected are pathogenic microorganisms associated with infection, e.g., sepsis. In some embodiments, one or more of the microorganisms detected are contaminants, e.g., introduced into the sample during or after collection from the subject. In some embodiments, one or more of the microorganisms detected are commensal bacteria, i.e., non-pathogenic bacteria of the subject. In some embodiments, both pathogenic microorganisms associated with infection and contaminants are detected. In some embodiments, both pathogenic microorganisms associated with infection and commensal bacteria are detected.

In some embodiments, one, some, or all of the microorganisms detected have antimicrobial resistance or susceptibility conferring genetic material, e.g., antimicrobial resistance conferring genetic material listed in Table 11, which can be targeted by one or more DIANAs listed in Table 4, e.g., SEQ ID NOs: 141-493, and the antimicrobial resistance conferring genetic material is identified using the techniques described herein, e.g., by contacting the microbial genetic material with one or more DIANAs targeting the antimicrobial resistance or susceptibility conferring genetic material, e.g., a DIANA having a sequence shown in Table 4, e.g., SEQ ID NOs: 141-493.

In some embodiments, one DIANA targeting antimicrobial resistance or susceptibility conferring genetic material is used. In some embodiments, more than one DIANA targeting antimicrobial resistance or susceptibility conferring genetic material is used. In some embodiments, two or more DIANAs, both targeting the same antimicrobial resistance or susceptibility conferring genetic material, are used.

In some embodiments, the two or more DIANAs target the same amplicon. In some embodiments, the two or more DIANAs target different amplicons.

In some embodiments, the DIANA targeting antimicrobial resistance or susceptibility conferring genetic material is universal, e.g., to bacteria or fungi, to a genus, or to a species. In some embodiments, the DIANA targeting antimicrobial resistance or susceptibility conferring genetic material is pathogen specific.

A non-limiting example utilizing two DIANA probes for this purpose include, in some embodiments, one single DIANA probe may be utilized as a more general probe, targeting resistance conferring genetic material in a universal manner, whereas a second DIANA probe may be utilized as a more specific probe, targeting resistance conferring genetic material in a pathogen specific manner. In other embodiments, both DIANA probes target the resistance conferring genetic material in a pathogen specific manner.

In some embodiments, pathogen specific detection of resistance conferring genetic material is accomplished on the same amplicon, whereas in other embodiments, it is accomplished on differing amplicons.

Stoichiometrics, i.e., the relative signal between targets detected, can be used in a variety of ways, for example, to associate a detected genetic material, e.g., an antibiotic resistance gene, with a particular microorganism in a mixed population. These methods employ the procedures for absolute and/or semi-quantitation of microorganisms described herein.

In some embodiments, the methods described herein comprise:
(i) contacting amplified microbial genetic materials with a plurality of DNA Invading Artificial Nucleic Acids (DIANAs) that bind to a single species or group of microbes;
(ii) contacting amplified microbial genetic materials with a plurality of DNA Invading Artificial Nucleic Acids (DIANAs) that bind to microbial genetic material which confers resistance or reduced susceptibility to antimicrobials; and
(iii) determining the stoichiometry between the signal obtained from the detected single species or group of microbes and the signal obtained from the detected genetic material which confers resistance or reduced susceptibility to antimicrobials;
wherein stoichiometry is used to determine which microbial species contains the genetic material which confers resistance or reduced susceptibility to antimicrobials.

In some embodiments, the use of stoichiometrics is preferred when there are minimal biases in detection, or if biases do occur, they can be accounted for.

In some embodiments, the use of stoichiometrics is preferred when the genomic copy number relationship between the genomic sequence utilized for pathogen ID and resistance conferring marker ID is known. In some embodiments, the use of stoichiometrics is preferred when the genomic copy number relationship between the genomic sequence utilized for pathogen ID and resistance conferring marker ID is, while not know, can be measured, or if not measure, accounted for. In some embodiments, the use of stoichiometrics is preferred when the genomic copy number relationship between the genomic sequence utilized for pathogen ID and resistance conferring marker ID is constant. In some embodiments, the use of stoichiometrics is preferred when the genomic copy number relationship between the genomic sequence utilized for pathogen ID and resistance conferring marker ID is, while not constant, is constant within a given range, e.g., 5%, 10%, 15%, 20% or 25%.

In some embodiments, the use of stoichiometrics is preferred when it is feasible to attain either semi-quantitative or quantitative measurements from the assay.

In some embodiments, the use of stoichiometrics cannot deduce the required information with perfect confidence, but rather, only within a confidence level.

In some embodiments, the detection of the single species or group of microbes is semi-quantitative or quantitative. In some embodiments, the detection of the microbial genetic material which confers resistance or reduced susceptibility to antimicrobials is semi-quantitative or quantitative.

In some embodiments, the genomic copy number ratio between the target sequence used for detection of the single species or group of microbes and the microbial genetic material which confers resistance or reduced susceptibility to antimicrobials is known. In some embodiments, the genomic copy number ratio between the target sequence used for detection of the single species or group of microbes and the microbial genetic material which confers resistance or reduced susceptibility to antimicrobials is capable of being determined. In some embodiments, the genomic copy number ratio between the target sequence used for detection of the single species or group of microbes and the microbial genetic material which confers resistance or reduced susceptibility to antimicrobials is capable of being determined. In some embodiments, the genomic copy number ratio between the target sequence used for detection of the single species or group of microbes and the microbial genetic material which confers resistance or reduced susceptibility to antimicrobials is constant. In some embodiments, the genomic copy number ratio between the target sequence used for detection of the single species or group of microbes and the microbial genetic material which confers resistance or reduced susceptibility to antimicrobials does not vary by more than 5%, 10%, 15%, 20%, or 25%.

In some embodiments, determining the stoichiometry between the signal obtained from the detected single species or group of microbes and the signal obtained from the detected genetic material which confers resistance or reduced susceptibility to antimicrobials comprises determining the ratio between the signal obtained from the detected single species or group of microbes and the signal obtained from the detected genetic material which confers resistance or reduced susceptibility to antimicrobials.

In some embodiments, more than one species of microbe is detected and a stoichiometry is determined for each species of microbe. In some embodiments, a microbial species contains the genetic material which confers resistance or reduced susceptibility to antimicrobials if the stoichiometry, e.g., the ratio between the signal obtained for the microbial species and the signal obtained for the detected genetic material which confers resistance or reduced susceptibility to antimicrobials, is the same as the copy number ratio between the target sequence for identifying the microbial species and the genetic material which confers resistance or reduced susceptibility to antimicrobials, or does not vary by more than 5%, 10%, 15%, 20%, or 25%

For the case of illustration only, without limitation, consider two pathogens detected simultaneously, P-1 and P-2 combined with a single resistance conferring gene (for the purposes of illustration, termed R-1), one might attempt to deduce if R-1 originated from P-1 or P-2, or potentially, both.

For illustration purposes, assume that the detection signal attained in the test equated to 1,000 units and 50 units, for P-1 and P-2, respectively, and that the detection signal attained in the test equated to 100 units for R-1. Assuming no biases or noise in the system, and knowing that the genomic copy ratio for both P-1 and R-1, and P-2 and R-1 of 10:1 (10 copies of the sequence utilized for pathogen ID in relation to a single copy of the sequence utilized for pathogen resistance conferring gene detection), we can deduce that R-1 originated from P-1 and not P-2 due to stoichiometrics. Similarly, had the signal attained for R-1 been 5, one would deduce that R-1 originated from P-2 and not P-1. Similarly, had the signal attained for R-1 been 105, one would deduce that R-1 originated from both P-1 and P-2.

In some embodiments, determining the stoichiometry between the signal obtained from the detected single species or group of microbes and the signal obtained from the detected genetic material which confers resistance or reduced susceptibility to antimicrobials comprises accounting, e.g., mathematically and/or statistically, for assay-related biases. Assay-related biases include, but are not limited to, differing efficiencies in microbial lysis, differing likelihood of maintaining high molecular weight DNA, differing DNA isolation efficiencies, differing enzymatic amplification efficiencies, and differing DIANA detection efficiencies.

In some embodiments, calibration procedures are performed. In some embodiments, calibration procedures are performed during development of an assay, e.g., to account for assay-related biases. In other embodiments, calibration procedures are performed in a manner which closely approximates the expected conditions at the time of the assay.

In some embodiments, a step-wise manner of calibration is performed, wherein multiple calibrations are done at different levels. In some embodiments, a single calibration is performed, e.g., taking into account the entire sample-in/results-out process.

In some embodiments, calibration comprises calibration of DIANA probe capture/detection biases. In some embodiments, calibration comprises calibration of amplification biases. In some embodiments, calibration comprises calibration of lysis yield is required. In some embodiments, calibration comprises only one of the aforesaid calibrations. In some embodiments, calibration comprises more than one or all of the aforesaid calibrations. In other embodiments, calibration comprises a single calibration encompassing multiple parameters.

In some embodiments, a mixed assay result containing *S. aureus*, CoNS, and mecA is deconvolved. In some embodiments, the calibrations comprise one or more of: (1) DIANA signal output for each of the targets at various load input (amplicon copy number) and their mathematical relationships, (2) Enzymatic amplification output vs input to develop a mathematical relationship of *S. aureus* and mecA, as well as CoNS and, mecA, (3) Lysis yield vs load for *S. aureus* and CoNS. In some embodiments, by conducting some or all of the above calibrations, it is possible to develop a mathematical number, with confidence intervals, to deconvolve the origin of the mecA gene in cases where both *S. aureus* and CoNS were detected.

In some embodiments, stoichiometrics is used as a confirmatory step. By way of example, without limitation, should P-1 be identified as *S. aureus*, P-2 identified as *E. faecium*, and R-1 as the mecA gene; stoichiometrics may not be required to deconvolve the origin of R-1 as in the majority of cases (as defined by the user) mecA will have originated in *S. aureus*. However, in some embodiments, confirming this assumption is of utility.

In some embodiments, stoichiometrics can be used to indicate the potential for resistance conferring genetic material. By way of example, but not by way of limitation, stoichiometric might dictate that if a pathogen is detected at a load close to the limit of detection, the absence of a detected signal for R-1 implies that it is below its limit of detection and that no assumption may be made with regards to the resistance conferring genetic material.

In some embodiments, stoichiometrics can be used to rule-in an infection. By way of example, but not by way of limitation, if R-1 is detected and through calibration it was deduced that the detection of R-1 is more sensitive than the detection of P-1, the presence of a signal for R-1 indicates that an infection, with its corresponding resistance conferring gene is present, but the ID of the pathogen, in some embodiments, might remain unknown.

Culture-Free Identification of Fungal Pathogens

Fungal infections can be localized, as in the case of oral thrush, or systemic. Patients at significant risk for systemic fungal infection include immunocompromised patients, neutropaenic patients, and hospitalized patients with long-term intravascular lines. Systemic fungal infections cause ~25% of infection-related deaths in leukaemics. Infections due to *Candida* species are the fourth most important cause of nosocomial bloodstream infection. In certain other circumstances, fungal infections are also a major problem. Serious fungal infections may cause 5-10% of deaths in those undergoing lung, pancreas or liver transplantation. Acquired fungal sepsis occurs in up to 13% of very low birthweight infants. Fungi, for example, *Candida* yeast, can enter the bloodstream though a blood catheter.

Conventional diagnosis of systemic fungal infections is via blood culture. As with bacteria, blood culture diagnosis has the weakness that it delays administration of the proper antimicrobial. This is even more pronounced in the case of fungi, which often have a longer doubling time than bacteria. In contrast to blood culturing, the claimed methods, devices and kits allow the rapid and accurate identification of low levels of microorganisms in small volumes of blood.

Pathogens prevalent in fungal infections include, for example, *Candida parapsilosis, Candida tropicalis, Candida auris, Candida lusitaniae, Candida kefyr, Candida guilliermondii, Candida rugose, Candida famata, Candida norvegensis, Candida inconspicua, Candida albicans, Candida glabrata, Candida krusei, Cryptococcus neoformans, Aspergillus fumigatus, Aspergillus flavus*, and *Aspergillus clavatus*. In some embodiments, a test panel or test menu comprises all of the preceding pathogens. In some embodiments, a test panel or test menu comprises a subset of the preceding pathogens. In some embodiments, a test panel or test menu comprises only one of the preceding pathogens. In some embodiments, a test panel or test menu comprises some or all of the preceding pathogens and additional microorganisms not listed.

DIANAs, e.g., DIANAs for identifying fungi, e.g., DIANAs useful for identifying pathogens common in systemic fungal infections are listed in Table 12 and comprise SEQ ID NOs: 15-19 and 494-571. In some embodiments, one of the DIANA probes listed in Table 12, e.g., SEQ ID NOs: 15-19 and 494-571, is used in the methods, devices, and kits described herein, e.g., in a method for identifying a fungal species or groups of fungi. In some embodiments, some of the DIANA probes listed in Table 12, e.g., SEQ ID NOs: 15-19 and 494-571, are used in the methods, devices, and kits described herein, e.g., in a method for identifying a fungal species or groups of fungi. In some embodiments, all of the DIANA probes listed in Table 12, e.g., SEQ ID NOs: 15-19 and 494-571, are used in the methods, devices, and kits described herein, e.g., in a method for identifying a fungal species or groups of fungi. In some embodiments, some or all of the DIANA probes listed in Table 12, e.g., SEQ ID NOs: 15-19 and 494-571, are used in combination with DIANA probes not listed in Table 12, e.g., SEQ ID NOs: 15-19 and 494-571, in the methods, devices, and kits described herein e.g., in a method for identifying a fungal species or groups of fungi.

TABLE 12

DIANAs and microorganisms commonly associated with fungal bloodstream infections.

| Target | Seq ID |
|---|---|
| Candida albicans | 015 |
| Candida parapsilosis | 016 and 494-500 |
| Candida krusei | 017 |
| Candida glabrata | 018 |
| Candida tropicalis | 019 and 501-510 |
| Candida auris | 511-520 |
| Candida lusitaniae | 521-527 |
| Candida kefyr | 528-539 |
| Candida guilliermondii | 540-544 |
| Candida rugosa | 545-551 |
| Candida famata | 552-561 |
| Candida norvegensis | 562-566 |
| Candida inconspicua | 567-571 |

Kits

The present disclosure also provides kits for use of the DIANAs as described herein in the methods described herein. In some embodiments, the kit comprises reagents and protocols for detecting and/or identifying and/or evaluating one or more microorganisms from a sample without prior enrichment. In some embodiments, this kit contains reagents and protocols for the following processes:

(i) depleting eukaryotic DNA from the sample;
(ii) lysing one or more microbial cells in the sample, wherein the lysing of one or more microbial cells releases a plurality of microbial genetic materials;
(iii) isolating the plurality of microbial genetic materials;
(iv) amplifying the plurality of microbial genetic materials; and
(v) contacting the amplified microbial genetic materials with a plurality of DNA Invading Artificial Nucleic Acids (DIANAs) that bind to the single species or group of microbes associated with neonatal sepsis, wherein the plurality of DIANAs comprise one or more sequences selected from the group consisting of SEQ ID NOs: 20-571; and
(vi) detecting binding of the one or more of the plurality of DIANAs to the microbial genetic material of its respective single species or group of microbes, wherein the detection of binding indicates the presence of the one or more specific microbial species or groups of microbes associated with bloodstream infections in the sample.

In some embodiments, the comprises the fluidic device described herein. In some embodiments, the kit can additionally comprise instructions for use in any of the methods described herein. The included instructions may comprise a description of detecting microbial genetic material, e.g., by depleting eukaryotic DNA from a sample, lysing microbial cells, isolating genetic material, amplifying the genetic material, contacting the amplified genetic material with DIANAs, and detecting the binding. The kit may further comprise a description of obtaining a sample from a subject. In some embodiments, the instructions comprise selecting a subject for testing based on diagnostic criteria.

In some embodiments, the kit contains pre-calibrated reagents for load assessment, microbial spectrum analysis, and microbial detection.

In some embodiments, reagents are provided in suitable packaging. Suitable packaging includes, but is not limited to, vials, bottles, jars, flexible packaging, and the like.

In some embodiments, the kit may be utilized manually (human operation). In some embodiments, usage of the kit may be automated. Non-limiting examples for automating include robotic pipetting stations, and the fluidic devices described herein.

EXAMPLES

Example 1: Detection of Polymicrobial Infections

This example shows the detection of *E. coli* at 5 CFU/ml, *S. epidermidis* at 6 CFU/ml, *S. agalactiae* at 11 CFU/ml, *E. faecalis* at 19 CFU/ml and *C. parapsilosis* at 6 CFU/ml directly from human whole blood using the methods disclosed herein at two clinically relevant load levels.

Methods

Fresh human whole-blood drawn into a EDTA vacuette was inoculated with *E. coli* (ATCC #BAA-2469), *S. epidermidis* (ATCC #51625), *S. agalactiae* (ATCC #13813), *E. faecalis* (ATCC #29212), and *C. parapsilosis* (ATCC #14243) at the above loads (depicted in CFU/ml), simulating a complex of polymicrobial infection 1.5 ml of the contrived human blood was extracted and placed into a fresh vial. To the 1.5 ml blood sample, 1.5 ml of a lysis solution comprising of Tween-20 at 2% (v/v) and Triton-X100 at 1.3% (v/v) was added. After about 2 minutes, NaCl was added to the combined mixture to a final concentration of 150-300 mM and WAX conjugated magnetic particles were added. After about 2 minutes, a rare-earth magnet was used to immobilize the magnetic particles to the surface of the vial and about 3 ml of solution was removed and placed into a fresh vial.

A microbial lysis solution was added to the fresh vial. The microbial lysis solution contained the following: cross-linked and affinity purified lysozyme (2-13 mg), mutanolysin (10-350 U), zymolyase (18-200 U), and lysostaphin (65-250 U) in addition to a detergent based reagent containing a glucopyranoside, a cationic detergent, and a sulfobetaine (all of which were at concentrations above their individual CMCs (>10×)). The microbial lysis solution also included EDTA (at about 10 mM) and 2-Mercaptoethanol (—25 mM). The combined reaction mixture was incubated for about 10 to 15 minutes after which WAX conjugated magnetic particles were added to the solution. After about 2 minutes, a rare-earth magnet was used to immobilize the magnetic particles to the surface of the vial and the microbial lysis solution was removed and discarded.

The beads were washed repeatedly with a buffered wash solution containing 1 M NaCl. The microbial DNA was eluted off of the beads with an elution reagent at pH 12.5. Post-elution, the microbial DNA was subject to PCR of the 16S/18S rDNA with the following primer sequences (5'-3'):

Each primer contains a hapten moiety for subsequent labelling. Post-PCR, the sample was divided equally into 17 chambers, each loaded with biotinylated gamma-modified PNA probes with sequences identified in Table 1 and an invasion supporting reagent containing Tween-20, NaCl, and poly-EG-12,000. Each well was heated to 75-90° C. for 4 minutes with the addition of 5 ml of stock MyOne C1 Streptavidin coated beads. Post-immobilization of γPNA probes onto the beads, the beads were washed in a solution containing between 150-550 mM NaCl at a temperature at least 75-95° C. Post washing, to each chamber a solution containing a HRP-conjugate targeting the primer-hapten was added, which binds to the free hapten (if present) on the captured amplicon. After a number of wash steps with a neutral low salt wash, luminol was added to create a distinct optical signature only where the microbial DNA was captured. The optical signatures were read using a Promega GloMax plate reader with an integration time of 2.5 sec/well. Each reaction was completed in triplicate.

Results

Figure 7:
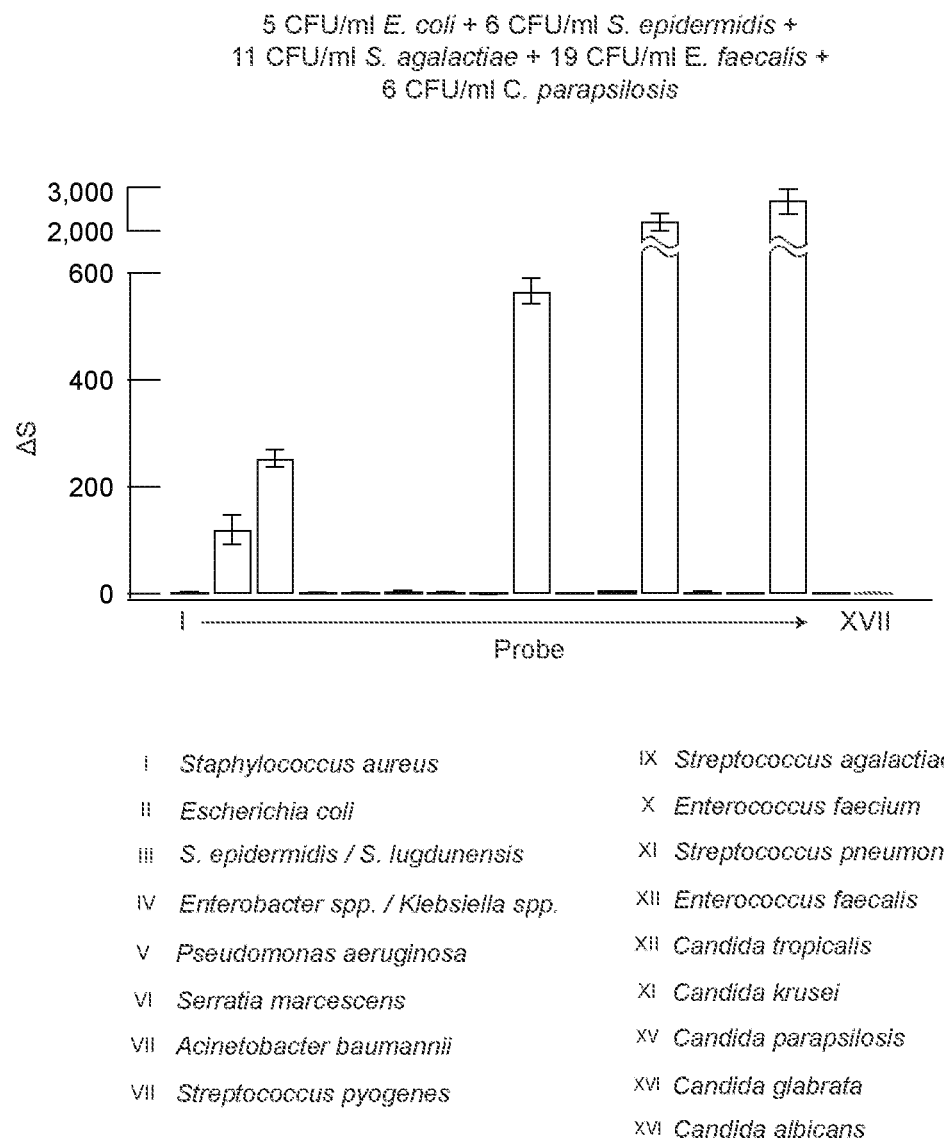
FIG. 7 is a graph showing signal as a function of pathogen load for deconvolving a complex polymicrobial infection.
Figure 8:
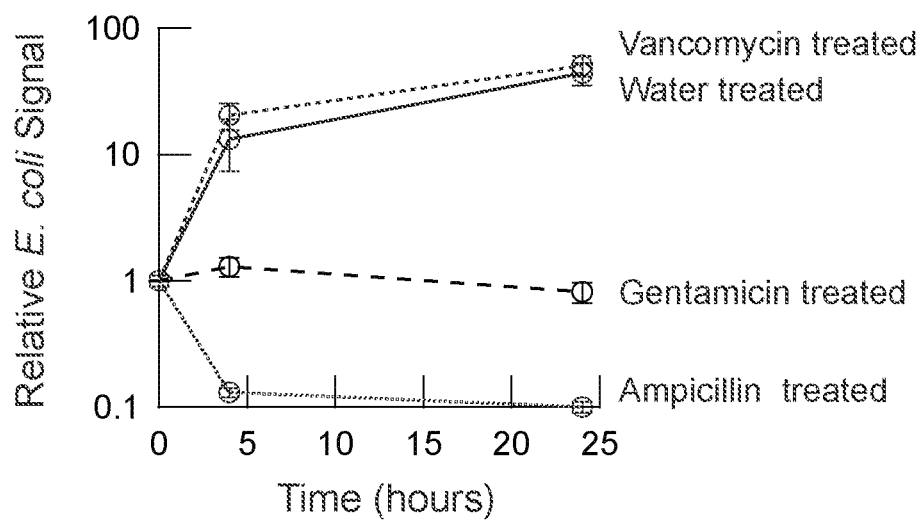
FIG. 8 is a graph showing signal over time for untreated E. coli (second from top) and E. coli treated with ampicillin (bottom), vancomycin (top), and gentamycin (second from bottom).
Figure 9:
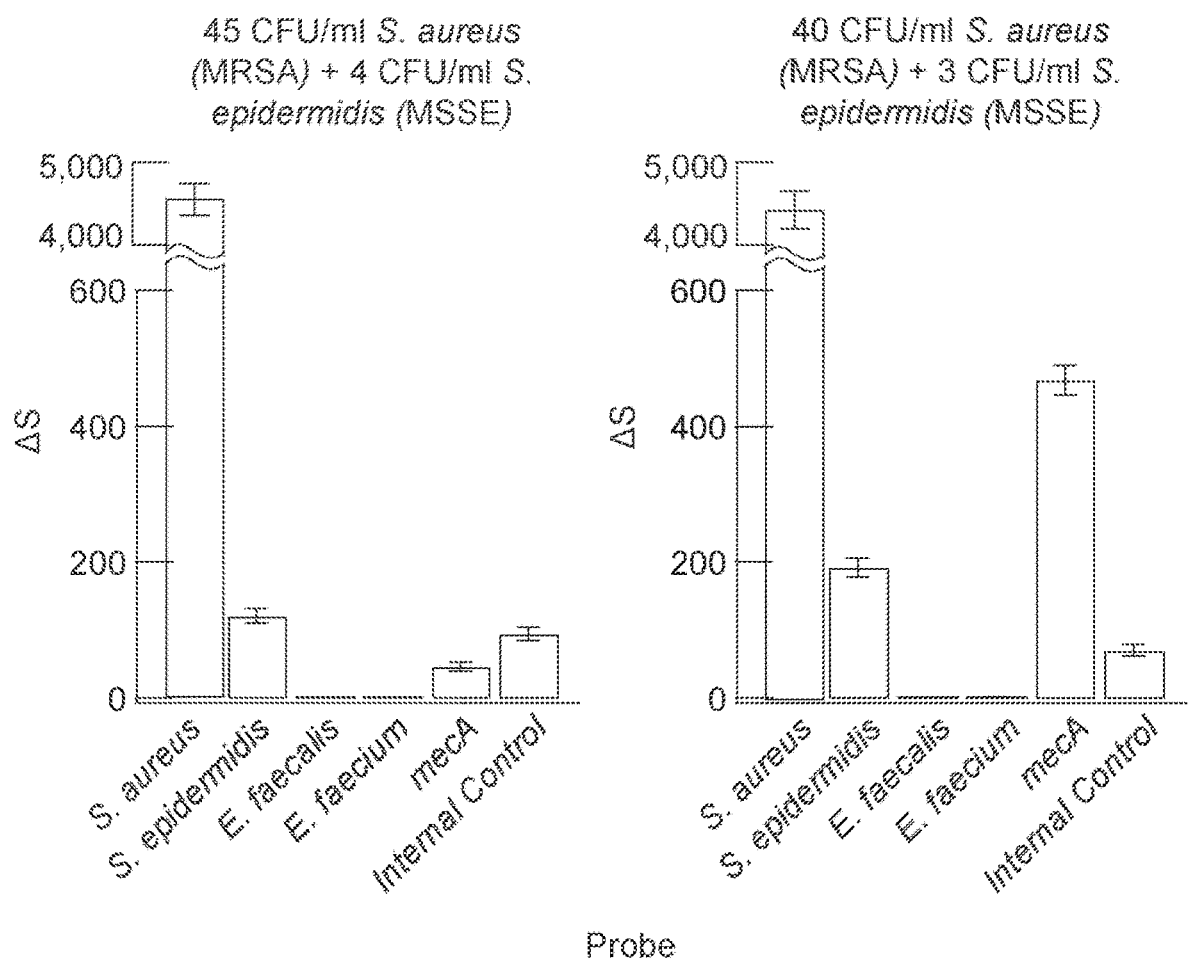
FIG. 9 are two graphs showing how a polymicrobial or mixed infection may be deconvolved to identify which of the two pathogens incorporated the genetic material that may confer resistance or reduced susceptibility to an antimicrobial. Deconvolving polymicrobial infections is further described in Example 1.

Clearly identifiable optical signatures were only seen in the *E. coli*, *S. epidermidis*, *S. agalactiae*, *E. faecalis* and *C. parapsilosis* channels (which came from the chambesr activated with a gamma-modified PNA probe specific to the above pathogens). See FIG. 7. Note also the ability to assess load based on a combination of microbial load input and rDNA copies.

These results show that the compositions and methods disclosed herein can de-convolve complex polymicrobial infections with at least two specific pathogen from a sample blood. Accordingly, the compositions and methods disclosed herein are useful for the detection and identification of microbes in a sample.

EQUIVALENTS

The foregoing written specification is considered to be sufficient to enable one ordinarily skilled in the art to practice the invention. The present invention is not to be limited in scope by examples provided, since the examples are intended as mere illustrations of one or more aspects of the invention. Other functionally equivalent embodiments are considered within the scope of the invention. Various modifications of the invention in addition to those shown and described herein will become apparent to those skilled in the art from the foregoing description. Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth or illustrated in the drawings. The invention is capable of other embodiments and of being practiced or of being carried out in various ways.

Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

All references, patents and patent applications that are recited in this application are incorporated by reference herein in their entirety.

The invention claimed is:

1. A method of identifying one or more specific microbial species in a sample from a subject, the method comprising:
  depleting eukaryotic DNA from the sample;
  lysing one or more microbial cells in the sample, wherein the lysing of one or more microbial cells releases a plurality of microbial genetic materials;
  isolating the plurality of microbial genetic materials;
  amplifying the plurality of microbial genetic materials;
  incubating the amplified microbial genetic materials with a plurality of DNA Invading Artificial Nucleic Acids (DIANAs) for less than 10 minutes at a temperature of below 65° C.; and
  detecting binding of one or more of the plurality of DIANAs to the amplified microbial genetic material of its respective single species or group of microbes, wherein the detection of binding indicates the presence of one or more specific microbial species or groups of microbes in the sample,
  wherein:
    the amplified microbial genetic materials are invaded by at least one of the DIANAs in the plurality of DIANAs during the incubation,
    one or more of the plurality of the DIANAs is a peptide nucleic acid, a locked nucleic acid, and/or a bridged nucleic acid, and
    the peptide nucleic acid, locked nucleic acid, and/or bridged nucleic acid:
      comprises a sequence that shares at least 60% identity with a sequence selected from the group consisting of SEQ ID NOS: 20-571,
      comprises the complement, reverse, or reverse complement of a sequence that shares at least 60% identity with a sequence selected from the group consisting of SEQ ID NOS: 20-571,
      comprises a sequence selected from the group consisting of SEQ ID NOS: 20-571 that lacks six or fewer bases at either or both ends, and/or
      comprises the complement, reverse, or reverse complement of a sequence selected from the group consisting of SEQ ID NOS: 20-571 that lacks six or fewer bases at either or both ends.

2. The method of claim 1, wherein incubating the amplified microbial genetic materials with a plurality of DNA Invading Artificial Nucleic Acids (DIANAs) is performed at a temperature that is greater than or equal to about 20° C.

3. The method of claim 1, wherein the amplified microbial genetic materials are incubated with a plurality of DNA Invading Artificial Nucleic Acids (DIANAs) in an incubation solution comprising a monovalent salt.

4. The method of claim 3, wherein the monovalent salt is present at a concentration above 50 mM.

5. The method of claim 1, wherein the amplified microbial genetic materials are incubated with a plurality of DNA Invading Artificial Nucleic Acids (DIANAs) in an incubation solution comprising a trivalent salt.

6. The method of claim 5, wherein the trivalent salt is present at a concentration above 0.1 mM.

7. The method of claim 1, wherein the amplified microbial genetic materials are incubated with a plurality of DNA Invading Artificial Nucleic Acids (DIANAs) in an incubation solution having a pH between about 10.2 and about 12.2.

8. The method of claim 1, wherein one or more of the plurality of DIANAs is modified to comprise a non-covalent binding moiety.

9. The method of claim 1, wherein one or more of the plurality of DIANAs is modified to comprise a covalent binding moiety.

10. The method of claim 1, wherein one or more of the plurality of DIANAs comprise a linker.

11. The method of claim 1, wherein one or more of the plurality of DIANAs further comprises a spacer.

12. The method of claim 1, wherein the sample is a blood sample.

13. The method of claim 12, wherein the blood sample is a whole blood sample.

14. A method as in claim 1, wherein the amplified microbial genetic materials are double stranded DNA.

15. A method as in claim 14, wherein a localized bubble is formed within the double stranded DNA during the incubation, and wherein the localized bubble allows the DIANA or DIANAs invading the double stranded DNA to bind to the double stranded DNA.

16. A method as in claim 1, wherein the incubation occurs in a solution comprising one or more crowding agents and one or more DNA denaturants.

17. A method as in claim 16, wherein the one or more crowding agents comprise poly-ethylene glycol, and wherein the poly-ethylene glycol has a molecular weight of greater than or equal to 200 Da and less than or equal to 20,000 Da.

18. A method as in claim 16, wherein the one or more DNA denaturants comprise DMSO, formamide, and/or a betaine.

19. A method as in claim 1, wherein the incubation is performed in a fluidic reservoir.

20. A method as in claim 19, wherein the fluidic reservoir is positioned in a fluidic device.

21. A method as in claim 1, wherein the incubation is performed in a processing chamber.

22. A method as in claim 21, wherein the processing chamber is positioned in a fluidic device.

23. A method as in claim 1, wherein incubating the amplified microbial genetic materials with a plurality of DNA Invading Artificial Nucleic Acids (DIANAs) is performed at a temperature that is less than or equal to about 64° C.

24. A method as in claim 1, wherein incubating the amplified microbial genetic materials with a plurality of DNA Invading Artificial Nucleic Acids (DIANAs) is performed at a temperature that is less than or equal to about 60° C.

25. A method as in claim 1, wherein the peptide nucleic acid, locked nucleic acid, and/or bridged nucleic acid comprises a sequence selected from the group consisting of SEQ ID NOs: 20-571, a sequence selected from the group consisting of SEQ ID NOs: 20-571 that lacks six or fewer bases at either or both ends, and/or the complement, reverse, or reverse complement of any of the foregoing sequences.

26. A method as in claim 1, wherein one or more of the plurality of DIANAs is a peptide nucleic acid, and wherein the peptide nucleic acid comprises a sequence that shares at least 60% identity with a sequence selected from the group consisting of SEQ ID NOs: 20-571 or the complement, reverse, or reverse complement of a sequence selected from the group consisting of SEQ ID NOs: 20-571.

27. A method as in claim 26, wherein the peptide nucleic acid is a γPNA.

* * * * *

UNITED STATES PATENT AND TRADEMARK OFFICE
CERTIFICATE OF CORRECTION

| | |
|---|---|
| PATENT NO. | : 11,840,721 B2 |
| APPLICATION NO. | : 16/499515 |
| DATED | : December 12, 2023 |
| INVENTOR(S) | : Alon Singer et al. |

It is certified that error appears in the above-identified patent and that said Letters Patent is hereby corrected as shown below:

In the Claims

At Column 261, Line 66 through Column 262, Line 23:
"2. The method of claim 1, wherein incubating the amplified microbial genetic materials with a plurality of DNA Invading Artificial Nucleic Acids (DIANAs) is performed at a temperature that is greater than or equal to about 20 °C."

Should read:
--2. The method of claim 1, wherein incubating the amplified microbial genetic materials with the plurality of DIANAs is performed at a temperature that is greater than or equal to about 20° C.--

At Column 262, Lines 24-27:
"3. The method of claim 1, wherein the amplified microbial genetic materials are incubated with a plurality of DNA Invading Artificial Nucleic Acids (DIANAs) in an incubation solution comprising a monovalent salt."

Should read:
--3. The method of claim 1, wherein the amplified microbial genetic materials are incubated with the plurality of DIANAs in an incubation solution comprising a monovalent salt.--

At Column 262, Lines 31-34:
"5. The method of claim 1, wherein the amplified microbial genetic materials are incubated with a plurality of DNA Invading Artificial Nucleic Acids (DIANAs) in an incubation solution comprising a trivalent salt."

Should read:
--5. The method of claim 1, wherein the amplified microbial genetic materials are incubated with the plurality of DIANAs in an incubation solution comprising a trivalent salt.--

Signed and Sealed this
Eighteenth Day of June, 2024

Katherine Kelly Vidal
*Director of the United States Patent and Trademark Office*

CERTIFICATE OF CORRECTION (continued)
U.S. Pat. No. 11,840,721 B2

At Column 262, Lines 37-41:

"7. The method of claim 1, wherein the amplified microbial genetic materials are incubated with a plurality of DNA Invading Artificial Nucleic Acids (DIANAs) in an incubation solution having a pH between about 10.2 and about 12.2."

Should read:

--7. The method of claim 1, wherein the amplified microbial genetic materials are incubated with the plurality of DIANAs in an incubation solution having a pH between about 10.2 and about 12.2.--

SEQUENCE LISTING

<160> NUMBER OF SEQ ID NOS: 588

<210> SEQ ID NO 1
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 1
aacggacgag aagct                                                          15

<210> SEQ ID NO 2
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 2
gtaaccattt ggagct                                                         16

<210> SEQ ID NO 3
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 3
gtaaccattt atggag                                                         16

<210> SEQ ID NO 4
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 4
ggacgttagt aactgaa                                                        17

<210> SEQ ID NO 5
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 5
ttaaccatag taggcc                                                         16

<210> SEQ ID NO 6
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 6
aagagtaatt aacacat                                                        17

<210> SEQ ID NO 7
<211> LENGTH: 16
<212> TYPE: DNA
<213> ORGANISM: Artificial Sequence

```
<220> FEATURE:
<223> OTHER INFORMATION: Synthetic Polynucleotide

<400> SEQUENCE: 7
ataagagaga ctaacg                                                      16

<210> SEQ ID NO 8
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 8
ggatgagagt aactgtt                                                     17

<210> SEQ ID NO 9
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 9
cacagagagc ttgctc                                                      16

<210> SEQ ID NO 10
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 10
tgagatcata gtggcgc                                                     17

<210> SEQ ID NO 11
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 11
tgagatctta gtggcgc                                                     17

<210> SEQ ID NO 12
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 12
tacctagaga tagtgg                                                      16

<210> SEQ ID NO 13
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 13
aaggtggtga acttaa                                                      16
```

<210> SEQ ID NO 14
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 14
aaggtggtga gcttaa                                                    16

<210> SEQ ID NO 15
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 15
gggtagccat ttatg                                                     15

<210> SEQ ID NO 16
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 16
acgcatcaaa aaagat                                                    16

<210> SEQ ID NO 17
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 17
ccgtggaaaa tctag                                                     15

<210> SEQ ID NO 18
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 18
cgtgtactgg aatgca                                                    16

<210> SEQ ID NO 19
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 19
caatgtcttc ggact                                                     15

<210> SEQ ID NO 20
<211> LENGTH: 20
<212> TYPE: DNA
<213> ORGANISM: Artificial Sequence
<220> FEATURE:
<223> OTHER INFORMATION: Synthetic Polynucleotide

```
<400> SEQUENCE: 20
agcgaacaga cgaggagctt                                           20

<210> SEQ ID NO 21
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 21
cgaggagctt gctcctctga                                           20

<210> SEQ ID NO 22
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 22
gctcctctga cgttagcggc                                           20

<210> SEQ ID NO 23
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 23
agcgaacaga taaggagctt                                           20

<210> SEQ ID NO 24
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 24
taaggagctt gctcctttga                                           20

<210> SEQ ID NO 25
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 25
gctcctttga cgttagcggc                                           20

<210> SEQ ID NO 26
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 26
aataccggat aatatattga                                           20

<210> SEQ ID NO 27
```

<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 27
ggataatata ttgaaccgca                                               20

<210> SEQ ID NO 28
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 28
tatattgaac cgcatggttc                                               20

<210> SEQ ID NO 29
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 29
aataccggat aatatgttga                                               20

<210> SEQ ID NO 30
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 30
ggataatatg ttgaaccgca                                               20

<210> SEQ ID NO 31
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 31
tatgttgaac cgcatggttc                                               20

<210> SEQ ID NO 32
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 32
ggtagtgctt gcactactgt                                               20

<210> SEQ ID NO 33
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 33

```
gcttgcacta ctgtccggcg                                          20

<210> SEQ ID NO 34
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 34
actactgtcc ggcgagtggc                                          20

<210> SEQ ID NO 35
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 35
tgtaaagtac ttttgttagg                                          20

<210> SEQ ID NO 36
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 36
ggaagaaaag ggaagtgcta                                          20

<210> SEQ ID NO 37
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 37
aaagggaagt gctaatacca                                          20

<210> SEQ ID NO 38
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 38
aagtgctaat accactttt                                           20

<210> SEQ ID NO 39
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 39
gttattcgag cggccaataa                                          20

<210> SEQ ID NO 40
<211> LENGTH: 20
<212> TYPE: DNA
```

```
<213> ORGANISM: Artificial Sequence
<220> FEATURE:
<223> OTHER INFORMATION: Synthetic Polynucleotide

<400> SEQUENCE: 40
cgagcggcca ataactgatt                                                    20

<210> SEQ ID NO 41
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 41
gccaataact gattagctag                                                    20

<210> SEQ ID NO 42
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 42
tttgttaggg aagaaaaggt                                                    20

<210> SEQ ID NO 43
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 43
agggaagaaa aggttgatgc                                                    20

<210> SEQ ID NO 44
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 44
gaaaaggttg atgctaatat                                                    20

<210> SEQ ID NO 45
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 45
cagacggtta gttaagcaag                                                    20

<210> SEQ ID NO 46
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 46
tagcaggtaa gtacttgtac                                                    20
```

<210> SEQ ID NO 47
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 47
ttcggtgatg aggaaggttg                                               20

<210> SEQ ID NO 48
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 48
tttagccctg gtgcccgaag                                               20

<210> SEQ ID NO 49
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 49
cttgacatcc gaagaagaac                                               20

<210> SEQ ID NO 50
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 50
agagggtaac caaccagcga                                               20

<210> SEQ ID NO 51
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 51
aaggcattta gtttaataga                                               20

<210> SEQ ID NO 52
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 52
gttgagcttt aagtttggcg                                               20

<210> SEQ ID NO 53
<211> LENGTH: 20
<212> TYPE: DNA
<213> ORGANISM: Artificial Sequence
<220> FEATURE:

<223> OTHER INFORMATION: Synthetic Polynucleotide

<400> SEQUENCE: 53
cggaagatga aagtgcggga                                              20

<210> SEQ ID NO 54
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 54
atgaaagtgc gggactgaga                                              20

<210> SEQ ID NO 55
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 55
gtgcgggact gagaggccgc                                              20

<210> SEQ ID NO 56
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 56
atgtgttaat agcacatcaa                                              20

<210> SEQ ID NO 57
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 57
taatagcaca tcaaattgac                                              20

<210> SEQ ID NO 58
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 58
cacatcaaat tgacgttaaa                                              20

<210> SEQ ID NO 59
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 59
catgttagat gcttgaaag                                               19

-continued

```
<210> SEQ ID NO 60
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 60
ctctgttgta agagaagaac                                                    20

<210> SEQ ID NO 61
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 61
tgtgagagtg gaaagttca                                                     19

<210> SEQ ID NO 62
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 62
tgtgagaatg gaaagttca                                                     19

<210> SEQ ID NO 63
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 63
aggtgttagg tcctttccgg                                                    20

<210> SEQ ID NO 64
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 64
cactctttta gagtgagcgg                                                    20

<210> SEQ ID NO 65
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 65
gatcgcggaa ggtggagaca                                                    20

<210> SEQ ID NO 66
<211> LENGTH: 20
<212> TYPE: DNA
<213> ORGANISM: Artificial Sequence
<220> FEATURE:
<223> OTHER INFORMATION: Synthetic Polynucleotide
```

```
<400> SEQUENCE: 66
ggaaggtgga gacaccctcc                                              20

<210> SEQ ID NO 67
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 67
tggagacacc ctccttcagt                                              20

<210> SEQ ID NO 68
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 68
aatgaaatgg acccacccct                                              20

<210> SEQ ID NO 69
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 69
acggcgtcat aatgcgccaa                                              20

<210> SEQ ID NO 70
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 70
aatttctatt ttcaaaaaaa                                              20

<210> SEQ ID NO 71
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 71
aggtccatga aagatattaa                                              20

<210> SEQ ID NO 72
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 72
tgggtgttga tattgcaaaa                                              20

<210> SEQ ID NO 73
<211> LENGTH: 20
```

```
<212> TYPE: DNA
<213> ORGANISM: Artificial Sequence
<220> FEATURE:
<223> OTHER INFORMATION: Synthetic Polynucleotide

<400> SEQUENCE: 73
ttttcaactg tgtggaattg                                              20

<210> SEQ ID NO 74
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 74
tggggtaaag tgatctacac                                              20

<210> SEQ ID NO 75
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 75
gggttaagcg tgctcagtat                                              20

<210> SEQ ID NO 76
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 76
caccgtagcc agtcttaagg                                              20

<210> SEQ ID NO 77
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 77
tgcgtggtga tggaagcgtg                                              20

<210> SEQ ID NO 78
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 78
gagcgaacca ttggtatcgg                                              20

<210> SEQ ID NO 79
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 79
```
tatggggatg ggtatcccaa                                                     20

<210> SEQ ID NO 80
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 80
ttgatcagtc cgcagcacgt                                                     20

<210> SEQ ID NO 81
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 81
cgtatgtcaa aagtaacaag                                                     20

<210> SEQ ID NO 82
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 82
tcgtaacgat gcgcaggcga                                                     20

<210> SEQ ID NO 83
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 83
gaagcggctt cccgcgcctc                                                     20

<210> SEQ ID NO 84
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 84
ggtttgtgcg gggtaaaacg                                                     20

<210> SEQ ID NO 85
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 85
acaacaagac gttcaagcgc                                                     20

<210> SEQ ID NO 86
<211> LENGTH: 20
<212> TYPE: DNA
<213> ORGANISM: Artificial Sequence

```
<220> FEATURE:
<223> OTHER INFORMATION: Synthetic Polynucleotide

<400> SEQUENCE: 86
aagatacgcg atcgtttagt                                          20

<210> SEQ ID NO 87
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 87
gccgcacggc gctgatcaat                                          20

<210> SEQ ID NO 88
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 88 tcggggttg ttgcaagaat                                           20

<210> SEQ ID NO 89
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 89
ctcacgatgg cgcgtggtgc                                          20

<210> SEQ ID NO 90
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 90
gattttatga agagctcccg                                          20

<210> SEQ ID NO 91
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 91
tttagcgagc gaagcggtgg                                          20

<210> SEQ ID NO 92
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 92
acaccgcgga tgaaacgggt                                          20
```

<210> SEQ ID NO 93
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 93
attgtttgta taccgaattg                                              20

<210> SEQ ID NO 94
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 94
ccgggacgaa gcgattggtg                                              20

<210> SEQ ID NO 95
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 95
gaggaggaat taaaagcggt                                              20

<210> SEQ ID NO 96
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 96
aagccaatga ggattgtcaa                                              20

<210> SEQ ID NO 97
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 97
acagagcatc ccgggggtgg                                              20

<210> SEQ ID NO 98
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 98
ttaacggcgc tctcggttta                                              20

<210> SEQ ID NO 99
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 99
gcgtgggtga cattcatcaa                                                   20

<210> SEQ ID NO 100
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 100
tcgttcccgg cagttgtcgg                                                   20

<210> SEQ ID NO 101
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 101
attgggttgg tccctcgaca                                                   20

<210> SEQ ID NO 102
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 102
cgagtgggaa taaggaggtg                                                   20

<210> SEQ ID NO 103
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 103
ggggattagt aaacgcggca                                                   20

<210> SEQ ID NO 104
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 104
atgttaagga cgttattgat                                                   20

<210> SEQ ID NO 105
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 105
gcgcccgtgc gctattgcgt                                                   20

<210> SEQ ID NO 106

<210> SEQ ID NO 106
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 106
aaaaaataaa acggataaaa                                               20

<210> SEQ ID NO 107
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 107
ctgtggttaa aagcactcat                                               20

<210> SEQ ID NO 108
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 108
gccgcggaat gaatcgcgct                                               20

<210> SEQ ID NO 109
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 109
ggcgttagcg aataaaaatg                                               20

<210> SEQ ID NO 110
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 110
atcatttggg cgcttttaac                                               20

<210> SEQ ID NO 111
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 111
aagaaacgta tcgctgtggc                                               20

<210> SEQ ID NO 112
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 112

-continued aacaccgccg tgggtaaaaa                                              20

<210> SEQ ID NO 113
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 113
attaacaaaa ggagacacac                                              20

<210> SEQ ID NO 114
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 114
gagttcgaaa caatgagggc                                              20

<210> SEQ ID NO 115
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 115
aaagtaaggt aaaacctgag                                              20

<210> SEQ ID NO 116
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 116
ttaagctgat tcatacggtg                                              20

<210> SEQ ID NO 117
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 117
gtgaagccga tagcccgata                                              20

<210> SEQ ID NO 118
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 118
caaccttgca taattcatca                                              20

<210> SEQ ID NO 119
<211> LENGTH: 20
<212> TYPE: DNA

<213> ORGANISM: Artificial Sequence
<220> FEATURE:
<223> OTHER INFORMATION: Synthetic Polynucleotide

<400> SEQUENCE: 119
ccaatggtgg ccaatttaaa                                          20

<210> SEQ ID NO 120
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 120
atgccggata tacgaatgca                                          20

<210> SEQ ID NO 121
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 121
tttcttttca tcaaaactga                                          20

<210> SEQ ID NO 122
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 122
gacaacaagg gtgggtccat                                          20

<210> SEQ ID NO 123
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 123
tatgcagcga agcggaatac                                          20

<210> SEQ ID NO 124
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 124
tgaaatcatt ttctccgtat                                          20

<210> SEQ ID NO 125
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 125
gaacggaaac gatggagctt                                          20

```
<210> SEQ ID NO 126
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 126
aaacgatgga gcttgctcca                                               20

<210> SEQ ID NO 127
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 127
tggagcttgc tccaggcgtc                                               20

<210> SEQ ID NO 128
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 128
ttgctccagg cgtcgagtgg                                               20

<210> SEQ ID NO 129
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 129
tgggaatctg cctttttgctg                                              20

<210> SEQ ID NO 130
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 130
tctgcctttt gctgggggat                                               20

<210> SEQ ID NO 131
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 131
ttttgctggg ggataacgta                                               20

<210> SEQ ID NO 132
<211> LENGTH: 20
<212> TYPE: DNA
<213> ORGANISM: Artificial Sequence
<220> FEATURE:
```

```
<223> OTHER INFORMATION: Synthetic Polynucleotide

<400> SEQUENCE: 132
taataccgaa tgataaagtg                                               20

<210> SEQ ID NO 133
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 133
cgaatgataa agtgtggcgc                                               20

<210> SEQ ID NO 134
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 134
ataaagtgtg gcgcatgcca                                               20

<210> SEQ ID NO 135
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 135
tgtggcgcat gccacgcttt                                               20

<210> SEQ ID NO 136
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 136
gcatgccacg cttttgaaag                                               20

<210> SEQ ID NO 137
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 137
cacgcttttg aaagatggtt                                               20

<210> SEQ ID NO 138
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 138
aggctgttgc taatatcagc                                               20
```

```
<210> SEQ ID NO 139
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 139
taatatcagc ggctgatgac                                              20

<210> SEQ ID NO 140
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 140
gcatctgata ctggca                                                  16

<210> SEQ ID NO 141
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 141
tgtcactttc aacatacaat                                              20

<210> SEQ ID NO 142
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 142
tgaagaaatt gtatttaagg                                              20

<210> SEQ ID NO 143
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 143
gtaacagcac ttattaataa                                              20

<210> SEQ ID NO 144
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 144
aataaaacag tgaagcaacc                                              20

<210> SEQ ID NO 145
<211> LENGTH: 20
<212> TYPE: DNA
<213> ORGANISM: Artificial Sequence
<220> FEATURE:
<223> OTHER INFORMATION: Synthetic Polynucleotide
```

<400> SEQUENCE: 145
tacggattgc ttcactgttt                                               20

<210> SEQ ID NO 146
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 146
ttcatctata tcgtattttt                                               20

<210> SEQ ID NO 147
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 147
ccgttctcat atagctcatc                                               20

<210> SEQ ID NO 148
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 148
ctttacctga gattttggca                                               20

<210> SEQ ID NO 149
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 149
gctagccatt cctttatctt                                               20

<210> SEQ ID NO 150
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 150
tctttaacat taatagccat                                               20

<210> SEQ ID NO 151
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 151
tgtttggatt atctttatca                                               20

<210> SEQ ID NO 152
<211> LENGTH: 20

```
<212> TYPE: DNA
<213> ORGANISM: Artificial Sequence
<220> FEATURE:
<223> OTHER INFORMATION: Synthetic Polynucleotide

<400> SEQUENCE: 152
tataaaccac ccaatttgtc                                              20

<210> SEQ ID NO 153
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 153
gtttctcctt gtttcatttt                                              20

<210> SEQ ID NO 154
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 154
ctgcagtacc ggatttgcca                                              20

<210> SEQ ID NO 155
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 155
gtttgcataa gatctataaa                                              20

<210> SEQ ID NO 156
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 156
tctttatgtg ttttatttac                                              20

<210> SEQ ID NO 157
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 157
tgtttggatt atctttatca                                              20

<210> SEQ ID NO 158
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 158
```
gttgcataac atcagttaat                                                    20

<210> SEQ ID NO 159
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 159
gatattttct ttggaaataa                                                    20

<210> SEQ ID NO 160
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 160
ttcttccaaa ctttgttttt                                                    20

<210> SEQ ID NO 161
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 161
cttttaataa gtgaggtgcg                                                    20

<210> SEQ ID NO 162
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 162
attgccatta ttttctaatg                                                    20

<210> SEQ ID NO 163
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 163
tagattgaaa ggatctgtac                                                    20

<210> SEQ ID NO 164
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 164
taatcagtat ttcaccttgt                                                    20

<210> SEQ ID NO 165
<211> LENGTH: 20
<212> TYPE: DNA
<213> ORGANISM: Artificial Sequence

```
<220> FEATURE:
<223> OTHER INFORMATION: Synthetic Polynucleotide

<400> SEQUENCE: 165
acctgaatca gctaataata                                              20

<210> SEQ ID NO 166
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 166
ttatctaaat ttttgtttga                                              20

<210> SEQ ID NO 167
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 167
gagcattata aaatggataa                                              20

<210> SEQ ID NO 168
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 168
tggtatatct tcaccaacac                                              20

<210> SEQ ID NO 169
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 169
tttttcatgc ctttttcaaa                                              20

<210> SEQ ID NO 170
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 170
tactgcctaa ttcgagtgct                                              20

<210> SEQ ID NO 171
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 171
agcaaagaaa atgttatctg                                              20
```

<210> SEQ ID NO 172
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 172
tctattgctt gttttaagtc                                                 20

<210> SEQ ID NO 173
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 173
taccatttac cacttcatat                                                 20

<210> SEQ ID NO 174
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 174
aacgttgtaa ccaccccaag                                                 20

<210> SEQ ID NO 175
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 175 tcttttgcc aacctttacc                                                  20

<210> SEQ ID NO 176
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 176
ttttataact tgttttatcg                                                 20

<210> SEQ ID NO 177
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 177
ctggtgaagt tgtaatctgg                                                 20

<210> SEQ ID NO 178
<211> LENGTH: 20
<212> TYPE: DNA
<213> ORGANISM: Artificial Sequence
<220> FEATURE:
<223> OTHER INFORMATION: Synthetic Polynucleotide

```
<400> SEQUENCE: 178
gttgagcaga ggttctttt                                              20

<210> SEQ ID NO 179
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 179
tcggttaatt tattatattc                                             20

<210> SEQ ID NO 180
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 180
tactcatgcc atacataaat                                             20

<210> SEQ ID NO 181
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 181
gacgtcatat gaaggtgtgc                                             20

<210> SEQ ID NO 182
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 182
agtgctaata attcacctgt                                             20

<210> SEQ ID NO 183
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 183
ggtggatagc agtacctgag                                             20

<210> SEQ ID NO 184
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 184
atcatttttc atgttgttat                                             20

<210> SEQ ID NO 185
```

```
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 185
ctcttttgaa ctttagcatc                                                20

<210> SEQ ID NO 186
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 186
ttagttgaat atctttgcca                                                20

<210> SEQ ID NO 187
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 187 tttcttttc tctattaatg                                                 20

<210> SEQ ID NO 188
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 188
gcgattgtat tgctattatc                                                20

<210> SEQ ID NO 189
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 189
cgattgtgac acgatagcca                                                20

<210> SEQ ID NO 190
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 190
atgttggagc tttttatcgt                                                20

<210> SEQ ID NO 191
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 191
```

-continued ttttcgagtc cctttttacc                                              20

<210> SEQ ID NO 192
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 192
ctgcatcatc tttatagcct                                              20

<210> SEQ ID NO 193
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 193
ttctttttgt tttaattctt                                              20

<210> SEQ ID NO 194
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 194
ttaatgggac caacataacc                                              20

<210> SEQ ID NO 195
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 195
gatgtgaagt cgcttttttct                                             20

<210> SEQ ID NO 196
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 196
gaagtcgctt ttcctagagg                                              20

<210> SEQ ID NO 197
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 197
atagttacga ctttctgttt                                              20

<210> SEQ ID NO 198
<211> LENGTH: 20
<212> TYPE: DNA

```
<213> ORGANISM: Artificial Sequence
<220> FEATURE:
<223> OTHER INFORMATION: Synthetic Polynucleotide

<400> SEQUENCE: 198
gttgtaagat gaaattttt                                                   20

<210> SEQ ID NO 199
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 199
aatcacttaa atattcatcc                                                  20

<210> SEQ ID NO 200
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 200
aatctcttaa atattcatcc                                                  20

<210> SEQ ID NO 201
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 201
tttaacggtt ttaagtggaa                                                  20

<210> SEQ ID NO 202
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 202
gtatcatctt gtacccaatt                                                  20

<210> SEQ ID NO 203
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 203
ccatttgttg tttgatatag                                                  20

<210> SEQ ID NO 204
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 204
agaaatactt agttctttag                                                  20
```

<210> SEQ ID NO 205
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 205
gctttataat cttttttaga                                             20

<210> SEQ ID NO 206
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 206
tctttggaac gatgcctatc                                             20

<210> SEQ ID NO 207
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 207
tgctgttcct gtattggcca                                             20

<210> SEQ ID NO 208
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 208
acattgtttc ggtctaaaat                                             20

<210> SEQ ID NO 209
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 209
cacgttctga ttttaaattt                                             20

<210> SEQ ID NO 210
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 210
atgtatgctt tggtctttct                                             20

<210> SEQ ID NO 211
<211> LENGTH: 20
<212> TYPE: DNA
<213> ORGANISM: Artificial Sequence
<220> FEATURE:

<223> OTHER INFORMATION: Synthetic Polynucleotide

<400> SEQUENCE: 211
cctggaataa tgacgctatg                                       20

<210> SEQ ID NO 212
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 212
aatctaactt ccacatacca                                       20

<210> SEQ ID NO 213
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 213
tttaacaaaa ttaaattgaa                                       20

<210> SEQ ID NO 214
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 214
cgatcaatgt taccgtagtt                                       20

<210> SEQ ID NO 215
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 215
taattttata ttgagcatct                                       20

<210> SEQ ID NO 216
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 216 tttttttattt ttagatactt                                      20

<210> SEQ ID NO 217
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 217
atgaaaaaaa tttatattag                                       20

```
<210> SEQ ID NO 218
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 218
gtgttctagt tcttttgcta                                                   20

<210> SEQ ID NO 219
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 219
tagttctttt actaattatg                                                   20

<210> SEQ ID NO 220
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 220
aataacttgg ttattcaaag                                                   20

<210> SEQ ID NO 221
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 221
ttattcagag ataacgatat                                                   20

<210> SEQ ID NO 222
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 222
gatattgaga aaacaattag                                                   20

<210> SEQ ID NO 223
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 223
gaaaacaatt aattctattg                                                   20

<210> SEQ ID NO 224
<211> LENGTH: 20
<212> TYPE: DNA
<213> ORGANISM: Artificial Sequence
<220> FEATURE:
<223> OTHER INFORMATION: Synthetic Polynucleotide
```

<400> SEQUENCE: 224
ttgaaaaagg aaactataac                                      20

<210> SEQ ID NO 225
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 225
aaactataac aaagtatata                                      20

<210> SEQ ID NO 226
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 226
atataaaaat agttcagaaa                                      20

<210> SEQ ID NO 227
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 227
tagttcagaa gcatctaaac                                      20

<210> SEQ ID NO 228
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 228
aaactggcat atggagaaga                                      20

<210> SEQ ID NO 229
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 229
agaagaaatt atagatagga                                      20

<210> SEQ ID NO 230
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 230
ttgtagatag gaataaaaaa                                      20

<210> SEQ ID NO 231
<211> LENGTH: 20

```
<212> TYPE: DNA
<213> ORGANISM: Artificial Sequence
<220> FEATURE:
<223> OTHER INFORMATION: Synthetic Polynucleotide

<400> SEQUENCE: 231
caaagattta agtgtcaata                                                  20

<210> SEQ ID NO 232
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 232
aaaattacta atcatgaaat                                                  20

<210> SEQ ID NO 233
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 233
cataaaacta aaaaaatcgg                                                  20

<210> SEQ ID NO 234
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 234
aaactggaaa agataaaaag                                                  20

<210> SEQ ID NO 235
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 235
agttgatgtt agatataaca                                                  20

<210> SEQ ID NO 236
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 236
tgatgttaaa tataacatat                                                  20

<210> SEQ ID NO 237
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 237
```
atggaaatat acgccgtaat                                          20

<210> SEQ ID NO 238
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 238
aaatatggaa ctatacgacg                                          20

<210> SEQ ID NO 239
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 239
ttatgaagaa aagcattgga                                          20

<210> SEQ ID NO 240
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 240
cacaattaaa ctttatttat                                          20

<210> SEQ ID NO 241
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 241
tggaccaggg agtaataata                                          20

<210> SEQ ID NO 242
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 242
taagcattgg aaattagatt                                          20

<210> SEQ ID NO 243
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 243
ggattgaaaa ataggcaaaa                                          20

<210> SEQ ID NO 244
<211> LENGTH: 20
<212> TYPE: DNA
<213> ORGANISM: Artificial Sequence

```
<220> FEATURE:
<223> OTHER INFORMATION: Synthetic Polynucleotide

<400> SEQUENCE: 244
ccagacgtaa tagtacctgg                                                   20

<210> SEQ ID NO 245
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 245
aaaatggaca gaaaattaat                                                   20

<210> SEQ ID NO 246
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 246
taaaatcaga acgaggcaaa                                                   20

<210> SEQ ID NO 247
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 247
aacattaaaa tcagagcgag                                                   20

<210> SEQ ID NO 248
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 248
ataaaagata gaaatggtat                                                   20

<210> SEQ ID NO 249
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 249
gtatagagtt ggctaaaact                                                   20

<210> SEQ ID NO 250
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 250
tagctaaaac tggaaataca                                                   20
```

<210> SEQ ID NO 251
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 251
aatcggtatt gtccctaaca                                           20

<210> SEQ ID NO 252
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 252
gaaatacata cgaaatcggt                                           20

<210> SEQ ID NO 253
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 253
taaaacaccc aaaaataagt                                           20

<210> SEQ ID NO 254
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 254
cccaaagaaa aatatgatga                                           20

<210> SEQ ID NO 255
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 255
gacgatattg ctcgtggttt                                           20

<210> SEQ ID NO 256
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 256
ctcgtgactt acaaattgat                                           20

<210> SEQ ID NO 257
<211> LENGTH: 20
<212> TYPE: DNA
<213> ORGANISM: Artificial Sequence
<220> FEATURE:
<223> OTHER INFORMATION: Synthetic Polynucleotide

```
<400> SEQUENCE: 257
agctataacc aataaagtta                                              20

<210> SEQ ID NO 258
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 258
aaatgggttc agccagattc                                              20

<210> SEQ ID NO 259
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 259
aaaatgggta cagccagatt                                              20

<210> SEQ ID NO 260
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 260
taccaattaa aaagataaat                                              20

<210> SEQ ID NO 261
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 261
agatgaatat atagacaaat                                              20

<210> SEQ ID NO 262
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 262
ataaaaagac gaatctatag                                              20

<210> SEQ ID NO 263
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 263
aaatcataca atttacaaat                                              20

<210> SEQ ID NO 264
```

-continued

```
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 264
ctataaaaag ccgtgtttat                                                      20

<210> SEQ ID NO 265
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 265
aaatactgta aaaagtcgtg                                                      20

<210> SEQ ID NO 266
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 266
gaacgaagca acagtacacc                                                      20

<210> SEQ ID NO 267
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 267
tatccattga atgaagcaac                                                      20

<210> SEQ ID NO 268
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 268
ggttatgtgg gtccaattaa                                                      20

<210> SEQ ID NO 269
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 269
tatgtgggcc ccattaattc                                                      20

<210> SEQ ID NO 270
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 270
```
acgagttaaa aagtaagcaa                                              20

<210> SEQ ID NO 271
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 271
taagcaattt ggaaactata                                              20

<210> SEQ ID NO 272
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 272
aaactatagc aaaaatactg                                              20

<210> SEQ ID NO 273
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 273
ggaaaaaaag gcttagaacg                                              20

<210> SEQ ID NO 274
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 274
aaaaagggga ttagagcgcc                                              20

<210> SEQ ID NO 275
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 275
atgataaaca attgcaaaac                                              20

<210> SEQ ID NO 276
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 276
tggttttaag gtatccattg                                              20

<210> SEQ ID NO 277
<211> LENGTH: 20
<212> TYPE: DNA

```
<213> ORGANISM: Artificial Sequence
<220> FEATURE:
<223> OTHER INFORMATION: Synthetic Polynucleotide

<400> SEQUENCE: 277
tttagggtat ccattgctaa                                           20

<210> SEQ ID NO 278
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 278
acttatgaca ataaaccttt                                           20

<210> SEQ ID NO 279
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 279
acttacgata ataaatcttt                                           20

<210> SEQ ID NO 280
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 280
cattattgga gaaaaaggct                                           20

<210> SEQ ID NO 281
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 281
agaaaaaagc taaaaacgga                                           20

<210> SEQ ID NO 282
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 282
cggaaaagat cttcatttaa                                           20

<210> SEQ ID NO 283
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 283
aacaatagat gctagggtac                                           20
```

```
<210> SEQ ID NO 284
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 284
gatgctagag tacaagaaag                                              20

<210> SEQ ID NO 285
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 285
gtatttataa tcatatgaaa                                              20

<210> SEQ ID NO 286
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 286
ataaacatat gaaaaatgac                                              20

<210> SEQ ID NO 287
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 287
aaaaatgact ttggatctgg                                              20

<210> SEQ ID NO 288

<400> SEQUENCE: 288

000

<210> SEQ ID NO 289
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 289
atctggtaca gcattacaac                                              20

<210> SEQ ID NO 290
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 290
actggagaaa ttttagcttt                                              20
```

<210> SEQ ID NO 291
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 291
caacctaaaa ctggggaaat                                               20

<210> SEQ ID NO 292
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 292
gtaccccatc gtacgatgtt                                               20

<210> SEQ ID NO 293
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 293
taccccttca tatgatgttt                                               20

<210> SEQ ID NO 294
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 294
attcatgaat ggattaagca                                               20

<210> SEQ ID NO 295
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 295
tcattaatgg aattagcaat                                               20

<210> SEQ ID NO 296
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 296
aatcatgatt atcataaatt                                               20

<210> SEQ ID NO 297
<211> LENGTH: 20
<212> TYPE: DNA
<213> ORGANISM: Artificial Sequence
<220> FEATURE:

<223> OTHER INFORMATION: Synthetic Polynucleotide

<400> SEQUENCE: 297
gactaccgta aattaactaa                                          20

<210> SEQ ID NO 298
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 298
aaaaagagcc tttgctcaac                                          20

<210> SEQ ID NO 299
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 299
gagccgttac tcaataaatt                                          20

<210> SEQ ID NO 300
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 300
tcaaatcact acatcaccag                                          20

<210> SEQ ID NO 301
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 301
acccaaaaaa tattaacatc                                          20

<210> SEQ ID NO 302
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 302
ctacatcacc gggttcaacc                                          20

<210> SEQ ID NO 303
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 303
attaacgtct attattgcct                                          20

```
<210> SEQ ID NO 304
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 304
tagccttaaa agaaaataaa                                               20

<210> SEQ ID NO 305
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 305
taaactagac gacaatacta                                               20

<210> SEQ ID NO 306
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 306
caaaaatact aattttgata                                               20

<210> SEQ ID NO 307
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 307
ggtaagggtt ggcaaaaaga                                               20

<210> SEQ ID NO 308
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 308
ttatggtaaa ggatggcaaa                                               20

<210> SEQ ID NO 309
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 309
catgggggaa ttataatatc                                               20

<210> SEQ ID NO 310
<211> LENGTH: 20
<212> TYPE: DNA
<213> ORGANISM: Artificial Sequence
<220> FEATURE:
<223> OTHER INFORMATION: Synthetic Polynucleotide
```

<400> SEQUENCE: 310
gatgtatctt ggggagatta                                               20

<210> SEQ ID NO 311
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 311
atttaaagta gtagacggca                                               20

<210> SEQ ID NO 312
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 312
taacaagatt taaagtggta                                               20

<210> SEQ ID NO 313
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 313
gatttaaagc aagcaataga                                               20

<210> SEQ ID NO 314
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 314
gacggtaaga tagatttaaa                                               20

<210> SEQ ID NO 315
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 315
cagacaacat attttttgcc                                               20

<210> SEQ ID NO 316
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 316 tttttttgcac gtattgcatt                                              20

<210> SEQ ID NO 317
<211> LENGTH: 20

-continued

```
<212> TYPE: DNA
<213> ORGANISM: Artificial Sequence
<220> FEATURE:
<223> OTHER INFORMATION: Synthetic Polynucleotide

<400> SEQUENCE: 317
tgcattagca ttaggagcca                                          20

<210> SEQ ID NO 318
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 318
tagctttagg agctaaaaaa                                          20

<210> SEQ ID NO 319
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 319
tttgagcaag gtatgcaaga                                          20

<210> SEQ ID NO 320
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 320
aagatttagg tgttggtgaa                                          20

<210> SEQ ID NO 321
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 321
gaatcggtga aaatatcccg                                          20

<210> SEQ ID NO 322
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 322
tcccgagcga ttaccccttt                                          20

<210> SEQ ID NO 323
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 323
```
ttatcccttt tataaagcac                                              20

<210> SEQ ID NO 324
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 324
gcacaaattt caaatagtaa                                              20

<210> SEQ ID NO 325
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 325
tcaaatagta atttaaaaaa                                              20

<210> SEQ ID NO 326
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 326
tattattagc agattcagga                                              20

<210> SEQ ID NO 327
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 327
aaataatgac atattactag                                              20

<210> SEQ ID NO 328
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 328
ccaaggcgag atactagtaa                                              20

<210> SEQ ID NO 329
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 329
tactagtaaa tcctatacaa                                              20

<210> SEQ ID NO 330
<211> LENGTH: 20
<212> TYPE: DNA
<213> ORGANISM: Artificial Sequence

```
<220> FEATURE:
<223> OTHER INFORMATION: Synthetic Polynucleotide

<400> SEQUENCE: 330
atacaaattt tatcaatata                                               20

<210> SEQ ID NO 331
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 331
aattttgtca atctacagtg                                               20

<210> SEQ ID NO 332
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 332
ctttagaaaa taacggaaat                                               20

<210> SEQ ID NO 333
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 333
aaataacggg aatatacaaa                                               20

<210> SEQ ID NO 334
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 334
aaatcctcat gttttacgta                                               20

<210> SEQ ID NO 335
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 335
ttacgtgaaa caaagtctca                                               20

<210> SEQ ID NO 336
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 336
aaatctcaaa tatggaaaaa                                               20
```

```
<210> SEQ ID NO 337
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 337
ttggaaaaag tctattatat                                                    20

<210> SEQ ID NO 338
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 338
ttatacctaa aaaagacata                                                    20

<210> SEQ ID NO 339
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 339
attaactaat ggtatggaac                                                    20

<210> SEQ ID NO 340
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 340
acgtgtagtg actaaaacac                                                    20

<210> SEQ ID NO 341
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 341
gttaataaaa cacataggga                                                    20

<210> SEQ ID NO 342
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 342
tagagatgat atctacaaaa                                                    20

<210> SEQ ID NO 343
<211> LENGTH: 20
<212> TYPE: DNA
<213> ORGANISM: Artificial Sequence
<220> FEATURE:
<223> OTHER INFORMATION: Synthetic Polynucleotide
```

<400> SEQUENCE: 343
tatacaaaaa ttatgcccga                                           20

<210> SEQ ID NO 344
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 344
cccgaattat aggtaaatct                                           20

<210> SEQ ID NO 345
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 345
tggtaaatct ggcacagcag                                           20

<210> SEQ ID NO 346
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 346
aaaatgaatc aagggggaaac                                          20

<210> SEQ ID NO 347
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 347
tgaaacaagg tgaaaccgga                                           20

<210> SEQ ID NO 348
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 348
gacaaatagg ttggtttgtt                                           20

<210> SEQ ID NO 349
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 349
taataaaaat aatcctaata                                           20

<210> SEQ ID NO 350

```
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 350
atgataaaca taacccaat                                              20

<210> SEQ ID NO 351
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 351
atggcgatta atgttaaaga                                             20

<210> SEQ ID NO 352
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 352
tatgctaatg gcaattaatg                                             20

<210> SEQ ID NO 353
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 353
aaaataaagg gatggccagc                                             20

<210> SEQ ID NO 354
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 354
ggctagctat aatgctgcta                                             20

<210> SEQ ID NO 355
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 355
tgctactata tctggaaaag                                             20

<210> SEQ ID NO 356
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 356
```
gatgatttgt atgataatgg 20

<210> SEQ ID NO 357
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 357
atgatttata tgattatgga 20

<210> SEQ ID NO 358
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 358
ctcaatttga tatagatcag 20

<210> SEQ ID NO 359
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 359
ctaaatttga catagatgag 20

<210> SEQ ID NO 360
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 360
gaagcaatag aatcatcaga 20

<210> SEQ ID NO 361
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 361
aatgaaatat tattagcaga 20

<210> SEQ ID NO 362
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 362
atcaccaggt tcaacccaaa 20

<210> SEQ ID NO 363
<211> LENGTH: 20
<212> TYPE: DNA

```
<213> ORGANISM: Artificial Sequence
<220> FEATURE:
<223> OTHER INFORMATION: Synthetic Polynucleotide

<400> SEQUENCE: 363
attttacgat cctgaatgtt                                              20

<210> SEQ ID NO 364
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 364
ctttaacgcc taaactatta                                              20

<210> SEQ ID NO 365
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 365
ttttatcgga cgttcagtca                                              20

<210> SEQ ID NO 366
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 366
acttcaccat tatcgctttt                                              20

<210> SEQ ID NO 367
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 367
tataactgct atctttataa                                              20

<210> SEQ ID NO 368
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 368
tttgaaattt ttatcttcaa                                              20

<210> SEQ ID NO 369
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 369
tcaatagtat tattaatttc                                              20
```

```
<210> SEQ ID NO 370
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 370
cttttgaagc ataaaaatat                                              20

<210> SEQ ID NO 371
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 371
aaacccgaca actacaacta                                              20

<210> SEQ ID NO 372
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 372
ataagtggaa caatttttat                                              20

<210> SEQ ID NO 373
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 373
atgaatagaa taaagttgc                                               20

<210> SEQ ID NO 374
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 374
tgtttggggg ttgctcagag                                              20

<210> SEQ ID NO 375
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 375
tgacgtatcg gtaaaatctg                                              20

<210> SEQ ID NO 376
<211> LENGTH: 20
<212> TYPE: DNA
<213> ORGANISM: Artificial Sequence
<220> FEATURE:
```

<223> OTHER INFORMATION: Synthetic Polynucleotide

<400> SEQUENCE: 376
gagatagccg ctaacattaa                                              20

<210> SEQ ID NO 377
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 377
aaaaatacga gccgttatac                                              20

<210> SEQ ID NO 378
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 378
aattacgaaa tctggtgtat                                              20

<210> SEQ ID NO 379
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 379
atgtgcgaaa aaccttgcgc                                              20

<210> SEQ ID NO 380
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 380
gggaaaacga caattgctat                                              20

<210> SEQ ID NO 381
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 381
tgtactctcg ccggataaaa                                              20

<210> SEQ ID NO 382
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 382
cacggattac ttgttaaaaa                                              20

```
<210> SEQ ID NO 383
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 383
atgaatatga aatcaaccat                                               20

<210> SEQ ID NO 384
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 384
tgtagcattt tcagctttgc                                               20

<210> SEQ ID NO 385
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 385
aagtcaggtg aagatggatc                                               20

<210> SEQ ID NO 386
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 386
aaggtctgtt tgaattgtcc                                               20

<210> SEQ ID NO 387
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 387 ccctttgta ggctgcgata                                                20

<210> SEQ ID NO 388
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 388
agctcagcaa tttgtatgga                                               20

<210> SEQ ID NO 389
<211> LENGTH: 20
<212> TYPE: DNA
<213> ORGANISM: Artificial Sequence
<220> FEATURE:
<223> OTHER INFORMATION: Synthetic Polynucleotide
```

<400> SEQUENCE: 389
cgttgacata catcgttgcg					20

<210> SEQ ID NO 390
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 390
tgctgggata gctactcccg					20

<210> SEQ ID NO 391
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 391
tgggttatta ataaagatga					20

<210> SEQ ID NO 392
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 392
tgtttttgtt aagccggcgc					20

<210> SEQ ID NO 393
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 393
ggctcatcct tcggtgtgaa					20

<210> SEQ ID NO 394
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 394
tcaatagcgc ggacgaattg					20

<210> SEQ ID NO 395
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 395
cgcaattgaa tcggcaagac					20

<210> SEQ ID NO 396
<211> LENGTH: 20

```
<212> TYPE: DNA
<213> ORGANISM: Artificial Sequence
<220> FEATURE:
<223> OTHER INFORMATION: Synthetic Polynucleotide

<400> SEQUENCE: 396
gacagcaaaa tcttaattga                                            20

<210> SEQ ID NO 397
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 397
ctgtttcggg ctgtgaggtc                                            20

<210> SEQ ID NO 398
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 398
tgcggtattg ggaaacagtg                                            20

<210> SEQ ID NO 399
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 399
ttagctgttg gcgaggtgga                                            20

<210> SEQ ID NO 400
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 400
tcaggctgca gtacggaatc                                            20

<210> SEQ ID NO 401
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 401
tattcatcag gaagtcgagc                                            20

<210> SEQ ID NO 402
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 402
```
aaaggctctg aaaacgcagt                                               20

<210> SEQ ID NO 403
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 403
ccgttcccgc agacctttca                                               20

<210> SEQ ID NO 404
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 404
ggagcgagga cggatacagg                                               20

<210> SEQ ID NO 405
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 405
gcaaaaaaaa tatataaagc                                               20

<210> SEQ ID NO 406
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 406
gctgtagagg tctagcccgt                                               20

<210> SEQ ID NO 407
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 407 tatgtttttta caagataacg                                              20

<210> SEQ ID NO 408
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 408
attgtactga acgaagtcaa                                               20

<210> SEQ ID NO 409
<211> LENGTH: 20
<212> TYPE: DNA
<213> ORGANISM: Artificial Sequence

```
<220> FEATURE:
<223> OTHER INFORMATION: Synthetic Polynucleotide

<400> SEQUENCE: 409
tgcccggttt cacgtcatac                                           20

<210> SEQ ID NO 410
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 410
ttatccccgt atgatggccg                                           20

<210> SEQ ID NO 411
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 411
ggtattgcac ttcccgaact                                           20

<210> SEQ ID NO 412
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 412
accgcttgat cgtattagcg                                           20

<210> SEQ ID NO 413
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 413
ggctgtgata ttcaaagctc                                           20

<210> SEQ ID NO 414
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 414
ggctgcgata ttcaaagctc                                           20

<210> SEQ ID NO 415
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 415
aaaaatctta attgagcaag                                           20
```

```
<210> SEQ ID NO 416
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 416
tgattacatt ggcgttaaag                                                   20

<210> SEQ ID NO 417
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 417
tgattacatt ggcgataaag                                                   20

<210> SEQ ID NO 418
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 418
atttcggtct gtgaggtcgg                                                   20

<210> SEQ ID NO 419
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 419
cgagccggaa aaggctctg                                                    20

<210> SEQ ID NO 420
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 420
atgaatagaa taaaagtcgc                                                   20

<210> SEQ ID NO 421
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 421
atgaataaaa taaaagtcgc                                                   20

<210> SEQ ID NO 422
<211> LENGTH: 20
<212> TYPE: DNA
<213> ORGANISM: Artificial Sequence
<220> FEATURE:
<223> OTHER INFORMATION: Synthetic Polynucleotide
```

```
<400> SEQUENCE: 422
gtcgcaatca tcttcggcgg                                           20

<210> SEQ ID NO 423
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 423
gtcgcaatta tcttcggcgg                                           20

<210> SEQ ID NO 424
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 424
gtcgcaacta tcttcggcgg                                           20

<210> SEQ ID NO 425
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 425
tcttcggcgg ttgctcggag                                           20

<210> SEQ ID NO 426
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 426
tgatgtgtcg gtaaaatccg                                           20

<210> SEQ ID NO 427
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 427
gaaattgctg cgaacattga                                           20

<210> SEQ ID NO 428
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 428
gaacattgat acggaaaaat                                           20

<210> SEQ ID NO 429
```

-continued

```
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 429
gaacattaat actgaaaaat                                           20

<210> SEQ ID NO 430
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 430
aaaaattcga tccgcactac                                           20

<210> SEQ ID NO 431
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 431
aattacaaaa aacggtgtat                                           20

<210> SEQ ID NO 432
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 432
aattacaaaa aacggcgtat                                           20

<210> SEQ ID NO 433
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 433
ctatgcaaga agccatgtac                                           20

<210> SEQ ID NO 434
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 434
gggaagccga cagtctcccc                                           20

<210> SEQ ID NO 435
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 435
```
gggaagccga tagtctcccc                                              20

<210> SEQ ID NO 436
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 436
atactctccc cggataggaa                                              20

<210> SEQ ID NO 437
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 437
atattctccc cggataggaa                                              20

<210> SEQ ID NO 438
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 438
gcatgggctg cttgtcatga                                              20

<210> SEQ ID NO 439
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 439
gcatggtctg cttgtcatga                                              20

<210> SEQ ID NO 440
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 440
aaagcgaata cgaaacacgg                                              20

<210> SEQ ID NO 441
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 441
aaagagaata cgaaactcgg                                              20

<210> SEQ ID NO 442
<211> LENGTH: 20
<212> TYPE: DNA

<213> ORGANISM: Artificial Sequence
<220> FEATURE:
<223> OTHER INFORMATION: Synthetic Polynucleotide

<400> SEQUENCE: 442
gcgtattgat gtggctttcc                                        20

<210> SEQ ID NO 443
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 443
gcgtattgac gtggctttcc                                        20

<210> SEQ ID NO 444
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 444
ggctttcccg gttttgcatg                                        20

<210> SEQ ID NO 445
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 445
aaatgcgggg aggatggtgc                                        20

<210> SEQ ID NO 446
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 446
aggggctgtt tgtattgtct                                        20

<210> SEQ ID NO 447
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 447
agggtctgtt tgaattgtct                                        20

<210> SEQ ID NO 448
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 448
ctatgtgggc tgtgatattc                                        20

<210> SEQ ID NO 449
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 449
ctatgtaggc tgcgatattc                                               20

<210> SEQ ID NO 450
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 450
tccgcagctt gcatggacaa                                               20

<210> SEQ ID NO 451
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 451
tggcctacat tcttacaaaa                                               20

<210> SEQ ID NO 452
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 452
gggcatcgcc gttcccgaat                                               20

<210> SEQ ID NO 453
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 453
gggcatcgcc gtccccgaat                                               20

<210> SEQ ID NO 454
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 454
ttcaaatgat tgataaaggt                                               20

<210> SEQ ID NO 455
<211> LENGTH: 20
<212> TYPE: DNA
<213> ORGANISM: Artificial Sequence
<220> FEATURE:

<223> OTHER INFORMATION: Synthetic Polynucleotide

<400> SEQUENCE: 455
ttcaaattat tgataaaggt                                           20

<210> SEQ ID NO 456
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 456
ttcaaatgat tgaaaaggt                                            20

<210> SEQ ID NO 457
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 457
caagccggag gcgggtgcgc                                           20

<210> SEQ ID NO 458
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 458
caaaccggag gcgaggacgc                                           20

<210> SEQ ID NO 459
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 459
aggcgggtgc gcttacctac                                           20

<210> SEQ ID NO 460
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 460
ctttgtgaag ccggcacggt                                           20

<210> SEQ ID NO 461
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 461
tcgtcctttg gcgtaaccaa                                           20

```
<210> SEQ ID NO 462
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 462
gatagaagcg gcaggacaat                                               20

<210> SEQ ID NO 463
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 463
gatagaagca gcaggacaat                                               20

<210> SEQ ID NO 464
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 464
gaaaaatctt aattgagcaa                                               20

<210> SEQ ID NO 465
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 465
ctgtgaggtc gggtgtgcgg                                               20

<210> SEQ ID NO 466
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 466
ctgtgaggtc ggctgcgcgg                                               20

<210> SEQ ID NO 467
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 467
ggtcatggga aacgaggatg                                               20

<210> SEQ ID NO 468
<211> LENGTH: 20
<212> TYPE: DNA
<213> ORGANISM: Artificial Sequence
<220> FEATURE:
<223> OTHER INFORMATION: Synthetic Polynucleotide
```

```
<400> SEQUENCE: 468
ggtcatgggg aacgaggatg                                               20

<210> SEQ ID NO 469
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 469
attgtcggcg aagtggatca                                               20

<210> SEQ ID NO 470
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 470
ccggctgagc cacggtatct                                               20

<210> SEQ ID NO 471
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 471
ccggttgagc cacggtatct                                               20

<210> SEQ ID NO 472
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 472
ccatcaggaa aacgagccgg                                               20

<210> SEQ ID NO 473
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 473
ggctcagaaa atgcgatgat                                               20

<210> SEQ ID NO 474
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 474
ggctcagaga atgcgatgat                                               20

<210> SEQ ID NO 475
<211> LENGTH: 20
```

```
<212> TYPE: DNA
<213> ORGANISM: Artificial Sequence
<220> FEATURE:
<223> OTHER INFORMATION: Synthetic Polynucleotide

<400> SEQUENCE: 475
attacagttc ccgcagacat                                              20

<210> SEQ ID NO 476
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 476
attatcgttc cagcagacat                                              20

<210> SEQ ID NO 477
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 477
atcacgcttc ctgcactgat                                              20

<210> SEQ ID NO 478
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 478
atcacgcttc ccgcactaat                                              20

<210> SEQ ID NO 479
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 479
acattccggt cgaggaacga                                              20

<210> SEQ ID NO 480
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 480
atcgggtgca agagacggca                                              20

<210> SEQ ID NO 481
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 481
```
atcgggtgca agaaacggca                                              20

<210> SEQ ID NO 482
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 482
atcgggtgca ggaaacggca                                              20

<210> SEQ ID NO 483
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 483
aagaaagtat atcgggtgct                                              20

<210> SEQ ID NO 484
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 484
gcagagggct tgcccgtgtt                                              20

<210> SEQ ID NO 485
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 485
gcagagggct tgctcgtgtt                                              20

<210> SEQ ID NO 486
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 486 tttttgcag gaggatggcg                                               20

<210> SEQ ID NO 487
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 487
gttctaaatg aggtcaatac                                              20

<210> SEQ ID NO 488
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 488
gttctaaacg aggtcaatac                                         20

<210> SEQ ID NO 489
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 489
caataccatg cccggtttta                                         20

<210> SEQ ID NO 490
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 490
caataccatg ccaggtttta                                         20

<210> SEQ ID NO 491
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 491
tacccacgta tggtggccgc                                         20

<210> SEQ ID NO 492
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 492
tatccacgca tggcggctgc                                         20

<210> SEQ ID NO 493
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 493
tacccacgta tgatggccgc                                         20

<210> SEQ ID NO 494
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 494
ggtatcagta ttcagtagtc                                         20

<210> SEQ ID NO 495
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 495
agtattcagt agtcagaggt                                               20

<210> SEQ ID NO 496
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 496
cagtagtcag aggtgaaatt                                               20

<210> SEQ ID NO 497
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 497
cagaatgaaa agtgcttaac                                               20

<210> SEQ ID NO 498
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 498
tgcatttttt cttacacatg                                               20

<210> SEQ ID NO 499
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 499
ggtaggcctt ctatatgggg                                               20

<210> SEQ ID NO 500
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 500
taatgtcaac cgattattta                                               20

<210> SEQ ID NO 501
<211> LENGTH: 20
<212> TYPE: DNA
<213> ORGANISM: Artificial Sequence
<220> FEATURE:
<223> OTHER INFORMATION: Synthetic Polynucleotide

```
<400> SEQUENCE: 501
ggccggtcca tctttctgat                                               20

<210> SEQ ID NO 502
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 502
tccatctttc tgatgcgtac                                               20

<210> SEQ ID NO 503
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 503
tttctgatgc gtactggacc                                               20

<210> SEQ ID NO 504
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 504
ctgatttgct taattgcacc                                               20

<210> SEQ ID NO 505
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 505
acatgtgttt tttattgaac                                               20

<210> SEQ ID NO 506
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 506
aaatttcttt ggtggcggga                                               20

<210> SEQ ID NO 507
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 507
gcaatcctac cgccagaggt                                               20

<210> SEQ ID NO 508
```

```
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 508
tataactaaa ccaaactttt                                          20

<210> SEQ ID NO 509
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 509
tatttacagt caaacttgat                                          20

<210> SEQ ID NO 510
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 510
ttattattac aatagtcaaa                                          20

<210> SEQ ID NO 511
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 511
gggttttgga gggaggtcca                                          20

<210> SEQ ID NO 512
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 512
gggaggtcca cctcacggtg                                          20

<210> SEQ ID NO 513
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 513
cctcacggtg agtacttcca                                          20

<210> SEQ ID NO 514
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 514
```

```
gtacttccat atccaagacc                                         20

<210> SEQ ID NO 515
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 515
tatccaagac ctttcctctg                                         20

<210> SEQ ID NO 516
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 516
ctttcctctg cttcctcgca                                         20

<210> SEQ ID NO 517
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 517
tgatattttg catacacact                                         20

<210> SEQ ID NO 518
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 518
tgatttggat tttaaaacta                                         20

<210> SEQ ID NO 519
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 519
aacccaacgt taagttcaac                                         20

<210> SEQ ID NO 520
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 520
ctaaaacaaa aacataaaac                                         20

<210> SEQ ID NO 521
<211> LENGTH: 20
<212> TYPE: DNA
```

```
<213> ORGANISM: Artificial Sequence
<220> FEATURE:
<223> OTHER INFORMATION: Synthetic Polynucleotide

<400> SEQUENCE: 521
tcctcctcct cttagcaata                                               20

<210> SEQ ID NO 522
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 522
cttagcaata agaggaggac                                               20

<210> SEQ ID NO 523
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 523
agaggaggac tgttactttg                                               20

<210> SEQ ID NO 524
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 524
aaaaatacat tacacattgt                                               20

<210> SEQ ID NO 525
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 525 tgttttgcg aacaaaaaaa                                                20

<210> SEQ ID NO 526
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 526
aaataaattt ttttattcga                                               20

<210> SEQ ID NO 527
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 527 ttcgaattc ttaatatcaa                                                20
```

<210> SEQ ID NO 528
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 528
ctttgggtct ggttggccgg                                       20

<210> SEQ ID NO 529
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 529
ccggtccgat tttatgtcgc                                       20

<210> SEQ ID NO 530
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 530
tcgcgcactg gttttcaacc                                       20

<210> SEQ ID NO 531
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 531
aaccggatct ttccttctgg                                       20

<210> SEQ ID NO 532
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 532
ctggctaacc tgtactcctt                                       20

<210> SEQ ID NO 533
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 533
ccttgtgggt gcaggcgaac                                       20

<210> SEQ ID NO 534
<211> LENGTH: 20
<212> TYPE: DNA
<213> ORGANISM: Artificial Sequence
<220> FEATURE:

<223> OTHER INFORMATION: Synthetic Polynucleotide

<400> SEQUENCE: 534
agcaggcgaa agctcgaata                    20

<210> SEQ ID NO 535
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 535
gatcgtctga acaaggcctg                    20

<210> SEQ ID NO 536
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 536
gccagttctt gattctctgc                    20

<210> SEQ ID NO 537
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 537
agttttctat ttctcatcct                    20

<210> SEQ ID NO 538
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 538
aacaatattt tgtattatga                    20

<210> SEQ ID NO 539
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 539
ctattatact ataaaattta                    20

<210> SEQ ID NO 540
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 540
tggctaacca ttcgcccttg                    20

```
<210> SEQ ID NO 541
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 541
gaaattctta gatttactga                                               20

<210> SEQ ID NO 542
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 542
ttaattattt ttacagttag                                               20

<210> SEQ ID NO 543
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 543
atttttacag ttagtcaaat                                               20

<210> SEQ ID NO 544
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 544
acagttagtc aaattttgaa                                               20

<210> SEQ ID NO 545
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 545
ttcgacgcat ctgaggggtc                                               20

<210> SEQ ID NO 546
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 546
ggtgcgtact ctgagggtgc                                               20

<210> SEQ ID NO 547
<211> LENGTH: 20
<212> TYPE: DNA
<213> ORGANISM: Artificial Sequence
<220> FEATURE:
<223> OTHER INFORMATION: Synthetic Polynucleotide
```

```
<400> SEQUENCE: 547
gcgccttgcg gcaagccaga                                               20

<210> SEQ ID NO 548
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 548
aacaacaata caactttgtg                                               20

<210> SEQ ID NO 549
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 549
tgtgtctgaa caataacttc                                               20

<210> SEQ ID NO 550
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 550
cttcaagtac cgatcatcaa                                               20

<210> SEQ ID NO 551
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 551
catcaaattg ttaaaacaaa                                               20

<210> SEQ ID NO 552
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 552
agtattcttt ttgccagcgc                                               20

<210> SEQ ID NO 553
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 553
ttaattgcgc ggcgaaaaaa                                               20

<210> SEQ ID NO 554
<211> LENGTH: 20
```

```
<212> TYPE: DNA
<213> ORGANISM: Artificial Sequence
<220> FEATURE:
<223> OTHER INFORMATION: Synthetic Polynucleotide

<400> SEQUENCE: 554
ccttacacac agtgtttttt                                               20

<210> SEQ ID NO 555
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 555
gttattacaa gaactttttgc                                              20

<210> SEQ ID NO 556
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 556
tttggtctgg actagaaata                                               20

<210> SEQ ID NO 557
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 557
gtttgggcca gaggtttact                                               20

<210> SEQ ID NO 558
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 558
gaactaaact tcaatattta                                               20

<210> SEQ ID NO 559
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 559
tattgaattg ttacttattt                                               20

<210> SEQ ID NO 560
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 560
```
aattgtcaat ttgttgatta                                                20

<210> SEQ ID NO 561
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 561
aattcaaaaa atcttcaaaa                                                20

<210> SEQ ID NO 562
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 562
ctgtgattta aacttctttc                                                20

<210> SEQ ID NO 563
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 563
ttacaccgcg tgagcgcaca                                                20

<210> SEQ ID NO 564
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 564
acaacaccta aacacgaata                                                20

<210> SEQ ID NO 565
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 565
accatgtcac ccagagaaaa                                                20

<210> SEQ ID NO 566
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 566
aaatctcaaa cgagaagaaa                                                20

<210> SEQ ID NO 567
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 567
tgtgatttta acatctttac                                                   20

<210> SEQ ID NO 568
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 568
acactgcgtg agcgcacaac                                                   20

<210> SEQ ID NO 569
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 569
acaacaccta aacatgaata                                                   20

<210> SEQ ID NO 570
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 570
tacttactag tcactaagaa                                                   20

<210> SEQ ID NO 571
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 571
gaaaaatcta aagaaataa                                                    20

<210> SEQ ID NO 572
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 572
cccccccctc agttatcgtt tatttgatag tacc                                   34

<210> SEQ ID NO 573
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 573
cccccccctc agttatcgtt tatttgatag ttcc                                   34

<210> SEQ ID NO 574
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 574
cccttcccag agtttgatca tggctcag        28

<210> SEQ ID NO 575
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 575
cccttccaga gtttgatcct ggctcag        27

<210> SEQ ID NO 576
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 576 cccccggtt accttgttac gactt        25

<210> SEQ ID NO 577
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 577
cccccggcta ccttgttacg actt        24

<210> SEQ ID NO 578
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 578
cccttccctg atgactcgtg cctacta        27

<210> SEQ ID NO 579
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 579
ccctctccct gatgacttgc gcttacta        28

<210> SEQ ID NO 580
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 580
tgttgcaaga atacggactc a                                             21

<210> SEQ ID NO 581
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 581
cttcacagag ccaccgta                                                 18

<210> SEQ ID NO 582
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 582
cggctacctt gttacgactt                                               20

<210> SEQ ID NO 583
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 583
gagtttgatc ctggctcag                                                19

<210> SEQ ID NO 584
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 584
ggctgcgata ttcaaagctc                                               20

<210> SEQ ID NO 585
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 585
ggctgtgata ttcaaagctc                                               20

<210> SEQ ID NO 586
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 586 gccttttttcc ggctcg                                                  16

<210> SEQ ID NO 587

```
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 587
acttgttgag cagaggttct                                              20

<210> SEQ ID NO 588
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 588
gtaacattga tcgcaacgtt c                                            21
```